(12) United States Patent
Xia et al.

(10) Patent No.: US 12,151,999 B2
(45) Date of Patent: Nov. 26, 2024

(54) SMALL MOLECULE COMPOUNDS HAVING NAPHTHYLAMINE STRUCTURE AND APPLICATION THEREOF

(71) Applicant: Hangzhou PhecdaMed Co., Ltd., Hangzhou (CN)

(72) Inventors: Hongguang Xia, Hangzhou (CN); Mengyang Fan, Hangzhou (CN); Xufeng Cen, Hangzhou (CN); Xiaoyan Xu, Hangzhou (CN); Ronghai Wu, Hangzhou (CN); Dong Liu, Hangzhou (CN); Zhen Tian, Hangzhou (CN)

(73) Assignee: Hangzhou PhecdaMed Co., Ltd., Hangzhou (CN)

( * ) Notice: Subject to any disclaimer, the term of this patent is extended or adjusted under 35 U.S.C. 154(b) by 0 days.

(21) Appl. No.: 18/606,722

(22) Filed: Mar. 15, 2024

(65) Prior Publication Data
US 2024/0254078 A1   Aug. 1, 2024

Related U.S. Application Data

(63) Continuation of application No. 18/692,114, filed as application No. PCT/CN2022/119825 on Sep. 20, 2022.

(30) Foreign Application Priority Data

Sep. 22, 2021   (CN) .......................... 202111108417.6

(51) Int. Cl.

| | | |
|---|---|---|
| C07C 311/21 | (2006.01) | |
| A61K 31/18 | (2006.01) | |
| A61K 31/337 | (2006.01) | |
| A61K 31/381 | (2006.01) | |
| A61K 31/402 | (2006.01) | |
| A61K 31/41 | (2006.01) | |
| A61K 31/415 | (2006.01) | |
| A61K 31/4192 | (2006.01) | |
| A61K 31/4196 | (2006.01) | |
| A61K 31/42 | (2006.01) | |
| A61K 31/433 | (2006.01) | |
| A61K 31/44 | (2006.01) | |
| C07D 207/06 | (2006.01) | |
| C07D 231/18 | (2006.01) | |
| C07D 249/04 | (2006.01) | |

(Continued)

(52) U.S. Cl.
CPC ........... C07C 311/21 (2013.01); A61K 31/18 (2013.01); A61K 31/337 (2013.01); A61K 31/381 (2013.01); A61K 31/402 (2013.01); A61K 31/41 (2013.01); A61K 31/415 (2013.01); A61K 31/4192 (2013.01); A61K 31/4196 (2013.01); A61K 31/42 (2013.01); A61K 31/433 (2013.01); A61K 31/44 (2013.01); C07D 207/06 (2013.01); C07D 231/18 (2013.01); C07D 249/04 (2013.01); C07D 249/12 (2013.01); C07D 257/04 (2013.01); C07D 261/10 (2013.01); C07D 285/06 (2013.01); C07D 305/08 (2013.01); C07D 333/34 (2013.01); C07D 333/62 (2013.01)

(58) Field of Classification Search
None
See application file for complete search history.

(56) References Cited

U.S. PATENT DOCUMENTS

| | | |
|---|---|---|
| 2018/0170895 A1 | 6/2018 | Wipf et al. |
| 2020/0131121 A1 | 4/2020 | Kluge et al. |

FOREIGN PATENT DOCUMENTS

| | | |
|---|---|---|
| CN | 106565596 A | 4/2017 |
| CN | 107952073 A | 4/2018 |

(Continued)

OTHER PUBLICATIONS

Ge et al., "Discovery and Synthesis of Hydronaphthoquinones as Novel Protease Inhibitors", J. Med. Chem., Mar. 8, 2012 (Year: 2012).*

(Continued)

*Primary Examiner* — Andrew D Kosar
*Assistant Examiner* — Gillian A Hutter
(74) *Attorney, Agent, or Firm* — Cooley LLP

(57) ABSTRACT

The present application discloses small molecule compounds having a naphthylamine structure and an application thereof. In the present application, the structure of a compound having a structure as shown in general formula (I) is as shown in the drawing. The compound and the pharmaceutically acceptable salt, stereoisomer, solvate or prodrug thereof that are provided by the present application or the pharmaceutical composition provided by the present application can selectively induce autophagy in damaged mitochondria without affecting or only weakly affecting normal mitochondria, and further have superior metabolic stability and pharmacokinetic properties, lower toxicity, and better druggability.

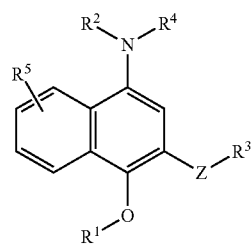

13 Claims, 8 Drawing Sheets

(51) Int. Cl.
  *C07D 249/12* (2006.01)
  *C07D 257/04* (2006.01)
  *C07D 261/10* (2006.01)
  *C07D 285/06* (2006.01)
  *C07D 305/08* (2006.01)
  *C07D 333/34* (2006.01)
  *C07D 333/62* (2006.01)

(56) References Cited

FOREIGN PATENT DOCUMENTS

| CN | 109293698 A | 2/2019 |
|---|---|---|
| CN | 111904958 A | 11/2020 |
| CN | 113476441 A | 10/2021 |
| WO | WO-2010005534 A2 | 1/2010 |
| WO | WO-2010102286 A2 | 9/2010 |
| WO | WO-2018130863 A1 | 7/2018 |
| WO | WO-2020231808 A1 | 11/2020 |
| WO | WO-2023045909 A1 | 3/2023 |

OTHER PUBLICATIONS

American Chemical Society, Chemical Abstract Service, RN: 858496-99-8, First made available to the public Aug. 5, 2005 (Year : 2005).*
Abulwerdi et al., "3-Substituted-N-(4-hydroxynaphthalen-1-yl) arylsulfonamides as a novel class of selective Mcl-1 inhibitors: structure-based design, synthesis, SAR, and biological evaluation". Journal of medicinal chemistry. May 22, 2014; 57(10): 4111-33.
Ge et al., "Discovery and synthesis of hydronaphthoquinones as novel proteasome inhibitors". Journal of medicinal chemistry. Mar. 8, 2012; 55(5): 1978-98.
International Preliminary Report on Patentability for International Application No. PCT/CN2022/119825 mailed on Apr. 4, 2024, 14 Pages.
International Search Report and Written Opinion for International Application No. PCT/CN2022/119825 dated Dec. 13, 2022, 18 pages.
Co-pending U.S. Appl. No. 18/692,114, inventor Xia; Hongguang , filed Mar. 14, 2024.

* cited by examiner

SMALL MOLECULE COMPOUNDS HAVING NAPHTHYLAMINE STRUCTURE AND APPLICATION THEREOF

CROSS-REFERENCES TO RELATED APPLICATIONS

This application is a continuation application of application Ser. No. 18/692,114, filed Mar. 14, 2024, which is a U.S. National Stage of International Application No. PCT/CN2022/119825, filed on Sep. 20, 2022, which claims priority to Chinese patent application No. 2021111084176, filed on Sep. 22, 2021, the entire contents of each of which is incorporated herein by reference in its entirety.

TECHNICAL FIELD

The current invention relates to the field of chemical drugs, and particularly to a class of small molecule compounds featuring a naphthylamine structure and their applications.

BACKGROUND

Mitophagy, a form of cellular target-specific autophagy, has the primary objective of identifying and eliminating dysfunctional mitochondria. Given the fundamental role mitochondria perform in energy provision via oxidative phosphorylation, their roles in energy metabolism, amino acid production, lipid synthesis, and ion homeostasis are equally crucial. Essential for maintaining function in cell types dependent on aerobic metabolism such as neuronal cells, muscle cells, and hepatocytes, etc. Homeostatic regulation of mitochondrial production and autophagy plays an integral role in preserving cellular function. Dysfunctional mitophagy will result in the accumulation of damaged mitochondria, a diminished ability to synthesize ATP+, and the production of substantial quantities of peroxides, leading to alterations in cellular intermediary metabolites, initiating a cascade of pathological consequence. If senescent or dysfunctional mitochondria are eliminated by enhancing mitophagy, mitophagy would undertake a protective role for the cell.

In the prior art, Chinese patent application No. 201910386493.X documents the compound UMI-77 as a mitophagy inducer. However, the researchers discovered in their study that UMI-77 as an mitophagy activator does not selectively induce autophagy in damaged mitochondria, and thus, it also triggers autophagy in healthy mitochondria during treatment, leading to adverse reactions. Furthermore, UMI-77 possess poor metabolic stability and is rapidly eliminated in in vitro metabolic stability experiments and PK experiments in mice, impacting significantly on druggability. Thus, developing a mitophagy activator that can effectively activate autophagy in damaged mitochondria, especially selectively induce autophagy in damaged mitochondria, and possesses desirable metabolic stability is pivotal for suppressing or mitigating many acute chronic diseases triggered by mitophagy dysfunction.

SUMMARY OF THE INVENTION

In order to solve the above problems, a goal of our current invention is to provide a class of small molecule compounds featuring the structure of naphthylamine and their applications, functioning as mitophagy inducers and capable of selectively activating autophagy in damaged mitochondria without influencing the healthy mitochondria, along with improved metabolic stability and higher bioavailability.

In a first aspect of the present invention, it provides a compound having a structure represented by Formula (I) and a pharmaceutically acceptable salt, stereoisomer, solvate or prodrug thereof,

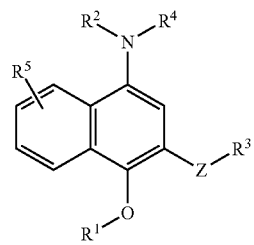

wherein Z is

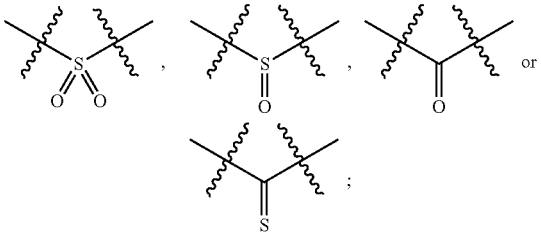

$R^1$ is hydrogen or $C_{1\sim6}$ alkyl;
$R^2$ is hydrogen, $C_{1\sim6}$ alkyl, three to six-membered cycloalkyl, three to six-membered epoxyalkyl, phenyl or $C_{1\sim6}$ alkyl substituted phenyl;
$R^3$ is

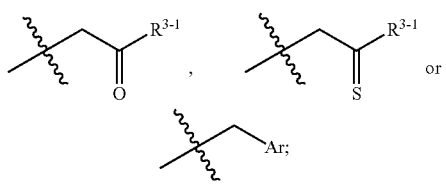

wherein $R^{3-1}$ is hydrogen, hydroxyl, $C_{1\sim6}$ alkyl, $C_{1\sim6}$ alkoxy, three to six-membered cycloalkyl, three to six-membered epoxyalkyl, amino, $C_{1\sim6}$ amido, —$CH_2C(O)R^{3-2}$, —$CH_2C(O)OR^{3-2}$ or —$CH_2C(O)N(R^{3-2}R^{3-2a})$,
$R^{3-2}$ and $R^{3-2a}$ are independently hydrogen, $C_{1\sim6}$ alkyl or three to six-membered cycloalkyl,
Ar is phenyl, naphthyl, 5- or 6-membered monocyclic heteroaryl, 8 to 10-membered fused bicyclic heteroaryl, 5- or 6-membered monocyclic heteroaryl in with at least one hydrogen atom substituted by $R^{3-3}$, 8 to 10-membered fused bicyclic heteroaryl with at least one hydrogen atom substituted by $R^{3-3}$, $R^{3-3}$ is hydrogen, halogen, $C_{1\sim6}$ alkyl, three to six-membered cycloalkyl, hydroxyl, $C_{1\sim6}$ alkoxy, three to six-membered epoxyalkyl, $C_{1\sim6}$ haloalkyl, $C_{2\sim6}$ alkenyl, $C_{2\sim6}$ alkynyl, —$N(R^{3-3a}R^{3-3b})$ or phenyl,
$R^{3-3a}$ and $R^{3-3b}$ are each independently hydrogen, $C_{1\sim6}$ alkyl or three to six-membered cycloalkyl;

$R^4$ is

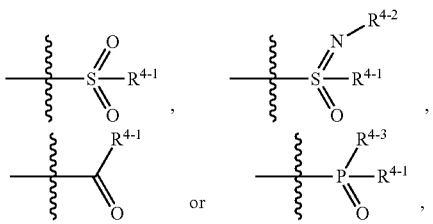

wherein $R^{4-1}$ is phenyl, naphthyl, phenyl with at least one hydrogen atom substituted by $R^{4-11}$, 5- or 6-membered monocyclic heteroaryl, 5- or 6-membered monocyclic heteroaryl with at least one hydrogen atom substituted by $R^{4-11}$ or 8 to 10-membered fused bicyclic heteroaryl, or 8 to 10-membered fused bicyclic heteroaryl with at least one hydrogen atom substituted by $R^{4-11}$, and the $R^{4-11}$ is hydrogen, halogen, nitro, nitrile group, hydroxyl, $C_{1\sim6}$ alkyl, three to six-membered cycloalkyl, $C_{1\sim6}$ alkoxy, —N($R^{4-1a}R^{4-1b}$), phenyl, $C_{1\sim6}$ haloalkyl, $C_{1\sim6}$ haloalkoxy, —C(O)O$R^{4-12}$, —C(O)$R^{4-12}$, —C(O)N($R^{4-1a}R^{4-1b}$), —S(O)$_2R^{4-12}$, —S(O)$R^{4-12}$, —OC(O)$R^{4-12}$, —OC(O)O$R^{4-12}$ or

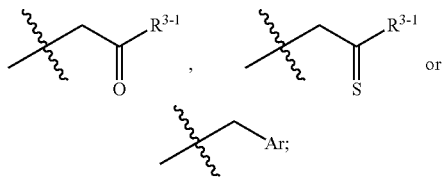

$R^{4-12}$, $R^{4-1a}$ and $R^{4-1b}$ are each independently hydrogen, $C_{1\sim6}$ alkyl, three to six-membered cycloalkyl, $C_{2\sim6}$ alkenyl, $C_{2\sim6}$ alkynyl, $C_{1\sim6}$ alkyl with at least one hydrogen substituted by halogen, $C_{2\sim6}$ alkenyl with at least one hydrogen substituted by halogen, three to six-membered cycloalkyl with at least one hydrogen substituted by halogen, or $C_{2\sim6}$ alkynyl with at least one hydrogen substituted by halogen, and $R^{4-1a}$ and $R^{4-1b}$ can bond with each other to form a ring, $R^{4-2}$ is hydrogen, $C_{1\sim6}$ alkyl or three to six-membered cycloalkyl, or when $R^2$ is $C_{1\sim6}$ alkyl, $R^{4-2}$ and $R^2$ are bonded to form a 4~8 membered (for example, 5~6 membered) ring, $R_{4-3}$ is hydrogen, $C_{1\sim6}$ alkyl or $C_{1\sim6}$ alkoxy;

In each Formula and context of this specification, unless explicitly stated, $R^5$ may not exist (that is, it is 0), or in the case of the valence bond rules allowing, one or more may exist at the same time, so the number of $R^5$ may be, for example, 0~5, preferably 0~4, more preferably 0~2 or 0~1. When the number of $R^5$ is not 0, each is independently selected from halogen, nitro, nitrile, —N$^+(R^{5-1})_3$, $C_{1\sim6}$ haloalkyl, —C(O)O$R^{5-1}$, —C(O)$R^{5-1}$, —C(O)N($R^{5-1}R^{5-1a}$), —S(O)$_2R^{5-1}$, —S(O)$R^{5-1}$, —S(O)$_2$N($R^{5-1}R^{5-1a}$), —S(O)N($R^{5-1}R^{5-1a}$), —N=C($R^{5-1}R^{5-1a}$), hydroxyl, $C_{1\sim6}$ alkyl, phenyl, phenyl with at least one hydrogen substituted by $R^{5-1}$, $C_{1\sim6}$ alkoxy, —N($R^{5-1}R^{5-1a}$), —N($R^{5-1}$) C(O)$R^{5-1a}$, —N($R^{5-1}$)C(O)O$R^{5-1a}$, —N($R^{5-1}$)C(O)N($R^{5-1a}$  $R^{5-1b}$), —OC(O)$R^{5-1}$, —OC(O)O$R^{5-1}$, —OC(O)N($R^{5-1}R^{5-1a}$) or —S$R^{5-1}$, where $R^{5-1}$, $R^{5-1a}$ and $R^{5-1b}$ are each independently hydrogen, $C_{1\sim6}$ alkyl, $C_{2\sim6}$ alkenyl, $C_{2\sim6}$ alkynyl, $C_{1\sim6}$ alkyl with at least one hydrogen substituted by halogen, $C_{2\sim6}$ alkenyl with at least one hydrogen substituted by halogen and $C_{2\sim6}$ alkynyl with at least one hydrogen substituted by halogen.

In some preferred embodiments, the Z is

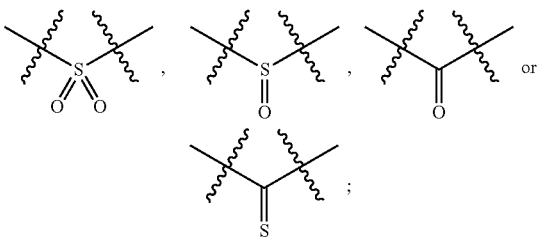

$R^1$ is hydrogen or $C_{1\sim4}$ alkyl;

$R^2$ is hydrogen, $C_{1\sim4}$ alkyl, three to six-membered cycloalkyl or four to six-membered epoxyalkyl;

$R^3$ is

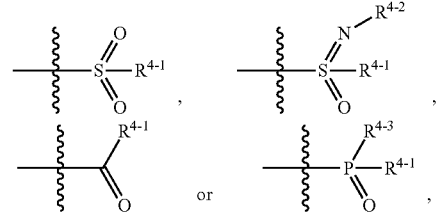

where $R^{3-1}$ is hydrogen, hydroxyl, $C_{1\sim4}$ alkyl, $C_{1\sim4}$ alkoxy, three to six-membered cycloalkyl, three to six-membered epoxyalkyl, —N($R^{3-2}R^{3-2a}$), —CH$_2$C(O)$R^{3-2}$, —CH$_2$C(O)O$R^{3-2}$ or —CH$_2$C(O)N$R^{3-2}R^{3-2a}$, $R^{3-2}$ and $R^{3-2a}$ are each independently hydrogen, $C_{1\sim4}$ alkyl or three to six-membered cycloalkyl, Ar is phenyl, a 5- or 6-membered monocyclic heteroaryl, a 5- or 6-membered monocyclic heteroaryl with at least one hydrogen atom substituted by $R^{3-3}$, and the $R^{3-3}$ is hydrogen, halogen, $C_{1\sim4}$ alkyl, three to six-membered cycloalkyl, hydroxyl, $C_{1\sim4}$ alkoxy, three to six-membered epoxyalkyl, $C_{1\sim4}$ haloalkyl, $C_{2\sim4}$ alkenyl, $C_{2\sim4}$ alkyne, —N($R^{3-3a}R^{3-3b}$) or phenyl, $R^{3-3a}$ and $R^{3-3b}$ are each independently hydrogen, $C_{1\sim4}$ alkyl or three to six-membered cycloalkyl;

$R^4$ is

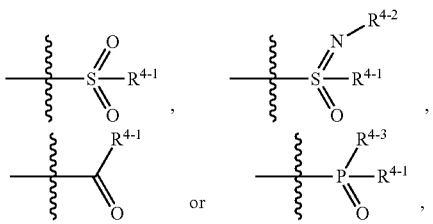

where $R^{4-1}$ is phenyl, phenyl with at least one hydrogen atom substituted by $R^{4-11}$, 5- or 6-membered monocyclic heteroaryl, and 5- or 6-membered monocyclic heteroaryl with at least one hydrogen atom substituted by $R^{4-11}$, 8- to 10-membered fused bicyclic heteroaryl, or 8- to 10-membered fused bicyclic heteroaryl with at least one hydrogen atom substituted by $R^{4-11}$, the $R^{4-11}$ is hydrogen, halogen, nitro, $C_{1\sim4}$ alkyl, three to six-membered cycloalkyl, $C_{1\sim4}$ alkoxy, —N($R^{4-1a}R^{4-1b}$), phenyl, $C_{1\sim4}$ haloalkyl, $C_{1\sim4}$ haloalkoxy or

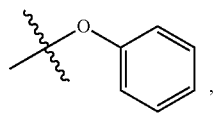 [SMILES: *Oc1ccccc1], $R^{4-1a}$ and $R^{4-1b}$ are each independently hydrogen, $C_{1-4}$ alkyl or three to six-membered cycloalkyl, and $R^{4-1a}$ and $R^{4-1b}$ can bond to each other to form a ring, $R^{4-2}$ is $C_{1-4}$ alkyl or three- to six-membered cycloalkyl, or when $R^2$ is $C_{1-4}$ alkyl, $R^{4-2}$ and $R^2$ are bonded to each other to form a 4~8 membered ring, $R^{4-3}$ is $C_{1-4}$ alkyl or $C_{1-4}$ alkoxy;

when the number of $R^5$ is not 0, each is independently halogen, nitro, nitrile, $-N^+(R^{5-1})_3$, $C_{1-4}$ haloalkyl, $-C(O)OR^{5-1}$, $-C(O)R^{5-1}$, $-C(O)N(R^{5-1}R^{5-1a})$, $-S(O)_2R^{5-1}$, $-S(O)R^{5-1}$, $-N=C(R^{5-1}R^{5-1a})$, hydroxyl, $C_{1-4}$ alkyl, phenyl, phenyl with at least one hydrogen substituted by $R^{5-1}$, $C_{1-4}$ alkoxy, $-N(R^{5-1}R^{5-1a})$, $-N(R^{5-1})C(O)R^{5-1a}$, $-OC(O)R^{5-1}$, $-OC(O)N(R^{5-1}R^{5-1a})$ or $-SR^{5-1}$, wherein $R^{5-1}$, $R^{5-1a}$ and $R^{5-1b}$ are each independently hydrogen, $C_{1-4}$ alkyl, $C_{2-4}$ alkenyl, $C_{2-4}$ alkynyl, $C_{1-4}$ alkyl with at least one hydrogen is substituted by halogen, $C_{2-4}$ alkenyl with at least one hydrogen is substituted by halogen, or $C_{2-4}$ alkynyl with at least one hydrogen substituted by halogen.

In some preferred embodiments, the Z is

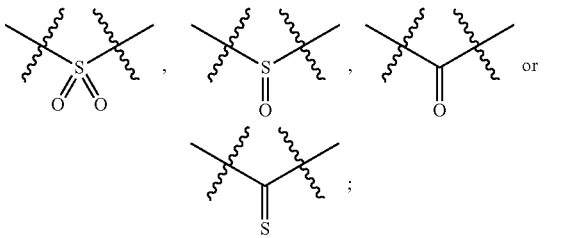

$R^1$ is hydrogen or $C_{1-4}$ alkyl;
$R^2$ is hydrogen, $C_{1-4}$ alkyl, three to six-membered cycloalkyl or four to six-membered epoxyalkyl;
$R^3$ is

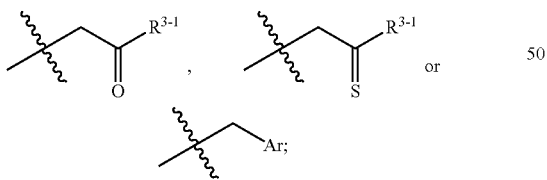

wherein, $R^{3-1}$ is hydrogen, hydroxyl, $C_{1-4}$ alkyl, $C_{1-4}$ alkoxy or $-N(R^{3-2}R^{3-2a})$,
$R^{3-2}$ and $R^{3-2a}$ are each independently hydrogen or $C_{1-4}$ alkyl,
Ar is phenyl, 5- or 6-membered monocyclic heteroaryl, 5- or 6-membered monocyclic heteroaryl with at least one hydrogen atom substituted by $R^{3-3}$, and the $R^{3-3}$ is hydrogen, halogen, $C_{1-4}$ alkyl, hydroxyl, $C_{1-4}$ alkoxy, $C_{1-4}$ haloalkyl or $-N(R^{3-3a}R^{3-3b})$,
$R^{3-3a}$ and $R^{3-3b}$ are each independently hydrogen or $C_{1-4}$ alkyl;

$R^4$ is

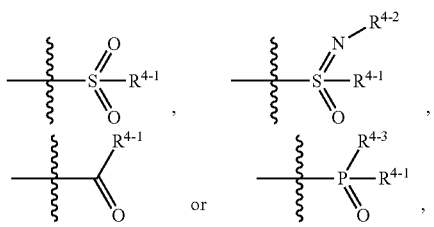

where $R^{4-1}$ is phenyl, phenyl with at least one hydrogen atom substituted by $R^{4-11}$, 5- or 6-membered monocyclic heteroaryl, and 5- or 6-membered monocyclic heteroaryl with at least one hydrogen atom substituted by $R^{4-11}$, the $R^{4-11}$ is hydrogen, halogen, nitro, $C_{1-4}$ alkyl, three to six-membered cycloalkyl, $C_{1-4}$ alkoxy, $-N(R^{4-1a}R^{4-1b})$, phenyl, $C_{1-4}$ haloalkyl, $C_{1-4}$ haloalkoxy or

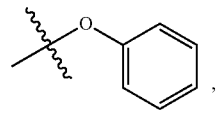 [SMILES: *Oc1ccccc1], $R^{4-1a}$ and $R^{4-1b}$ are independently hydrogen, $C_{1-4}$ alkyl or three- to six-membered cycloalkyl, and $R^{4-1a}$ and $R^{4-1b}$ can be bonded to each other to form a ring, $R^{4-2}$ is $C_{1-4}$ alkyl or three- to six-membered cycloalkyl, or when $R^2$ is $C_{1-4}$ alkyl, $R^{4-2}$ and $R^2$ are bonded to form a 4 to 8-membered ring, $R_{4-3}$ is $C_{1-4}$ alkyl or $C_{1-4}$ alkoxy;

when the number of $R^5$ is not 0, each is independently halogen, nitro, nitrile, $-N^+(R^{5-1})_3$, $C_{1-4}$ haloalkyl, $-C(O)OR^{5-1}$, $-C(O)R^{5-1}$, $-C(O)N(R^{5-1}R^{5-1a})$, $-S(O)_2R^{5-1}$, $-S(O)R^{5-1}$, $-N=C(R^{5-1}R^{5-1a})$, hydroxyl, $C_{1-4}$ alkyl, phenyl, phenyl with at least one hydrogen substituted by $R^{5-1}$, $C_{1-4}$ alkoxy, $-N(R^{5-1}R^{5-1a})$, $-N(R^{5-1})C(O)R^{5-1a}$ or $-OC(O)R^{5-1}$, wherein, $R^{5-1}$, $R^{5-1a}$ and $R^{5-1b}$ are each independently hydrogen, $C_{1-4}$ alkyl or $C_{1-4}$ alkyl with at least one hydrogen substituted by halogen.

In some preferred solutions, the Z is

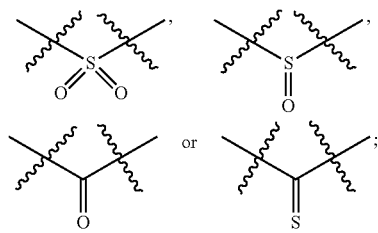

$R^1$ is hydrogen;
$R^2$ is hydrogen, methyl, ethyl, n-propyl, isopropyl,

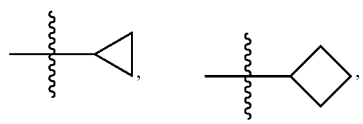

-continued

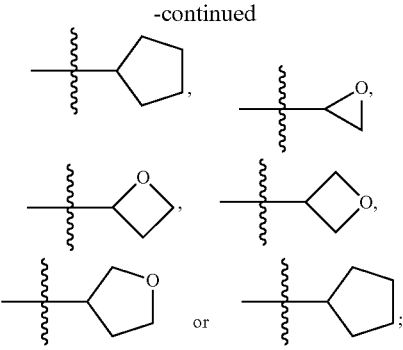

R³ is

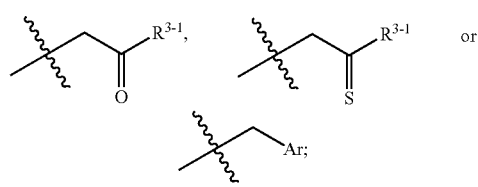

where R³⁻¹ is hydrogen, hydroxyl, methyl, ethyl, n-propyl, isopropyl, methoxy, ethoxy, n-propoxy, isopropoxy, n-butoxy, tert-butoxy, sec-butoxy or isobutoxy, Ar is phenyl, 5- or 6-membered nitrogen-containing monocyclic heteroaryl;

R⁴ is

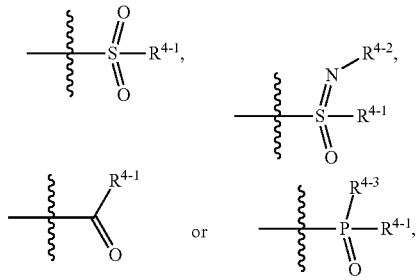

where R⁴⁻¹ is phenyl, phenyl with at least one hydrogen atom substituted by R⁴⁻¹¹, 5- or 6-membered monocyclic heteroaryl, and 5- or 6-membered monocyclic heteroaryl with at least one hydrogen atom substituted by R⁴⁻¹¹, 8 to 10-membered fused bicyclic heteroaryl, or 8 to 10-membered fused bicyclic heteroaryl with at least one hydrogen atom substituted with R⁴⁻¹¹, wherein R⁴⁻¹¹ is hydrogen, halogen, nitro, methyl, ethyl, n-propyl, isopropyl,

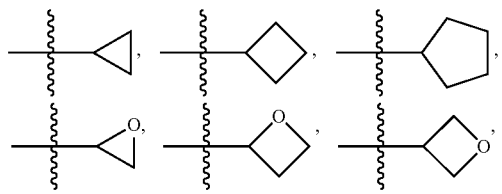

-continued

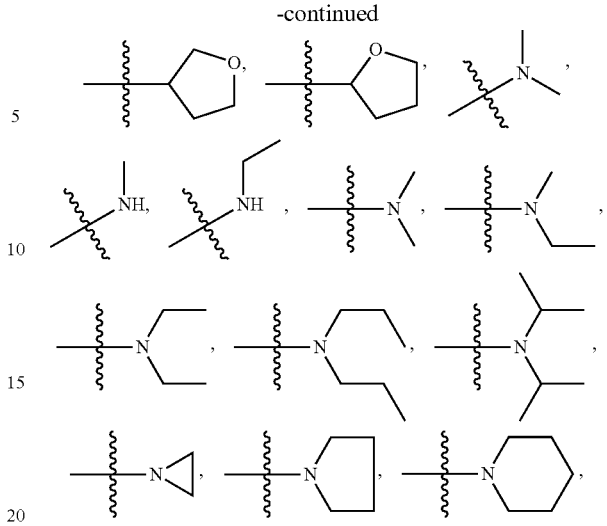

fluoromethyl, fluoroethyl, fluoro-n-propyl, fluoroisopropyl, chloromethyl, chloroethyl, chloro-n-propyl, chloroisopropyl, bromomethyl, bromoethyl, bromo-n-propyl, bromoisopropyl, iodomethyl, iodoethyl, iodo-n-propyl, iodoisopropyl, fluoromethoxy, fluoroethoxy, fluoro-n-propoxy, fluoroisopropoxy, chloromethoxy, chloroethoxy, chloro-n-propoxy, chloroisopropoxy, bromomethoxy, bromoethoxy, bromo-n-propoxy, bromoisopropoxy, iodooxymethyl, iodoethoxy, iodo-n-propoxy, iodoisopropoxy or

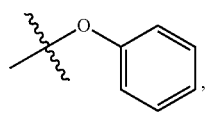 [SMILES: *Oc1ccccc1]

R⁴⁻² is methyl, ethyl, n-propyl or isopropyl, or when R² is methyl, ethyl or n-propyl, R⁴⁻² and R² are bonded to form a 4-8 membered ring, R₄₋₃ is methyl, ethyl, n-propyl, isopropyl, methoxy, ethoxy, n-propoxy or isopropoxy;

when the number of R⁵ is not 0, each is independently selected from halogen, nitro, nitrile, —N⁺(R⁵⁻¹)₃, fluoromethyl, fluoroethyl, fluoro-n-propyl, fluoroisopropyl, methchloroyl, chloroethyl, chloro-n-propyl, chloroisopropyl, bromomethyl, bromoethyl, bromo-n-propyl, bromoisopropyl, —C(O)OR⁵⁻¹, —C(O)R⁵⁻¹, —C(O)N(R⁵⁻¹R⁵⁻¹ᵃ), —S(O)₂R⁵⁻¹, —S(O)R⁵⁻¹, —N=C(R⁵⁻¹R⁵⁻¹ᵃ), hydroxyl, methyl, ethyl, n-propyl, isopropyl, phenyl, phenyl with at least one hydrogen substituted by R⁵⁻¹, methoxy, ethoxy, n-propoxy, isopropoxy, —N(R⁵⁻¹R⁵⁻¹ᵃ), —N(R⁵⁻¹)C(O)R⁵⁻¹ᵃ, —OC(O)R⁵⁻¹, wherein R⁵⁻¹, R⁵⁻¹ᵃ and R⁵⁻¹ᵇ are each independently hydrogen, methyl, ethyl, n-propyl, isopropyl and fluoromethyl, fluoroethyl, fluoro-n-propyl, fluoroisopropyl, chloromethyl, chloroethyl, chloro-n-propyl, chloroisopropyl, bromomethyl, bromoethyl, bromo-n-propyl and bromoisopropyl.

In some more preferred embodiments, the compound with the structure represented by the Formula (I) is selected from any one of the following compounds:

I-1
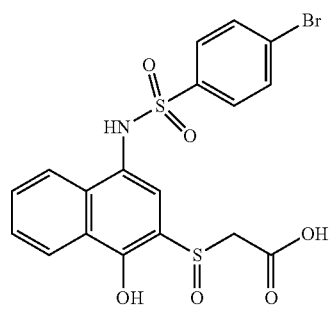
I-2
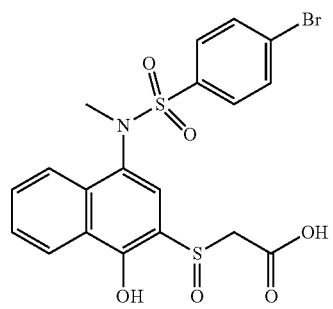
I-3
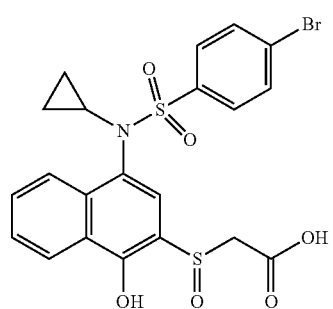
I-4
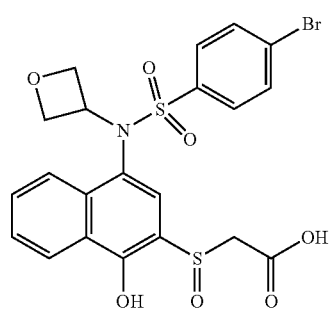
I-5
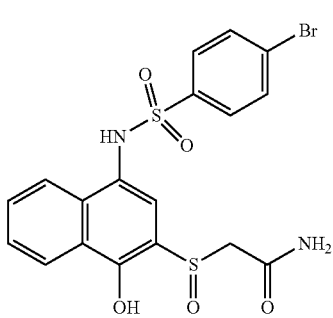
I-6
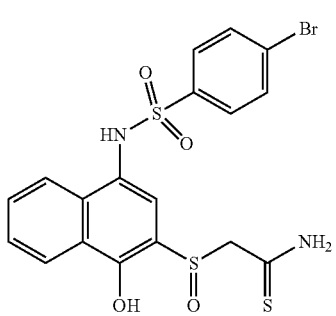
I-7-1
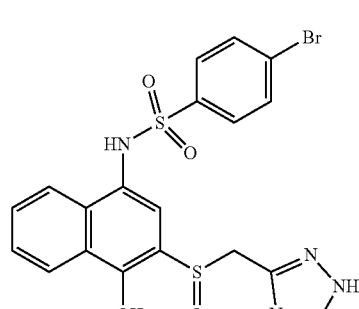
I-8
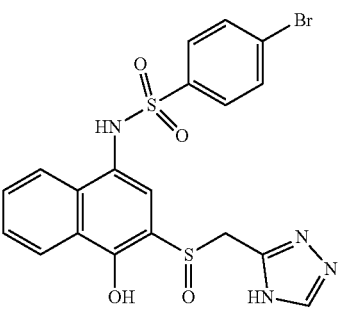
I-9-1
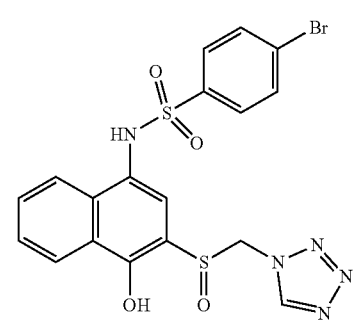
I-9-2
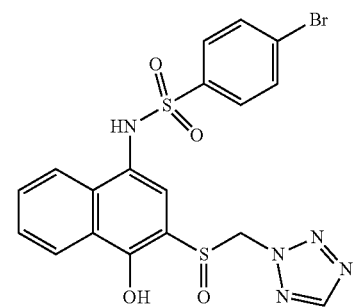

-continued
I-10
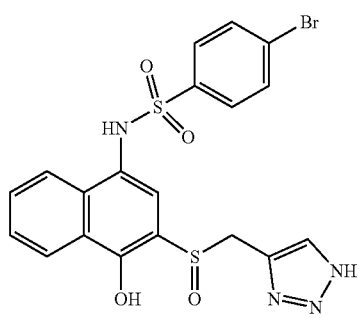
I-11-1
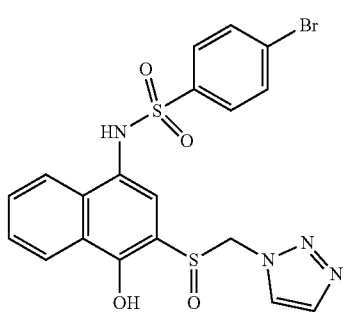
I-11-2
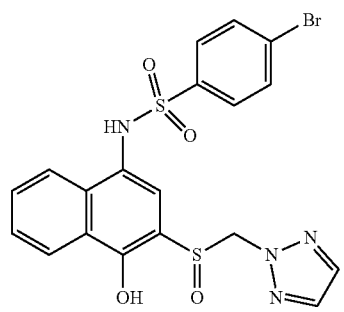
I-12
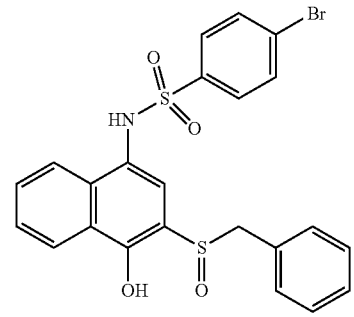
I-13-1
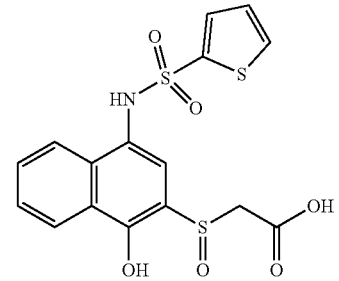
-continued
I-14-1
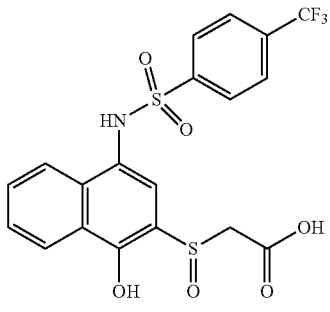
I-15-1
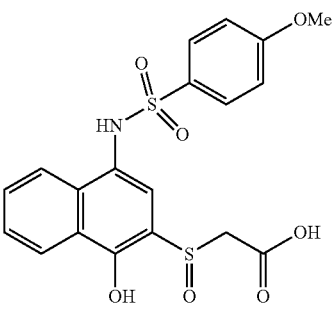
I-16-1
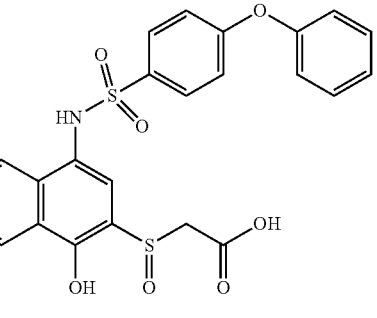
I-17-1
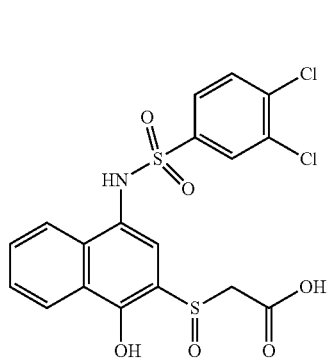
I-18-1
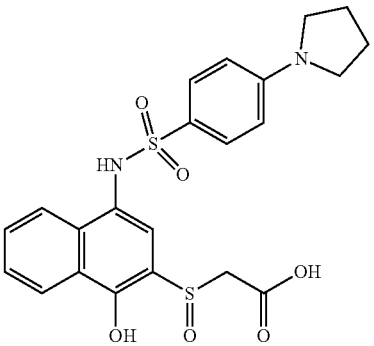

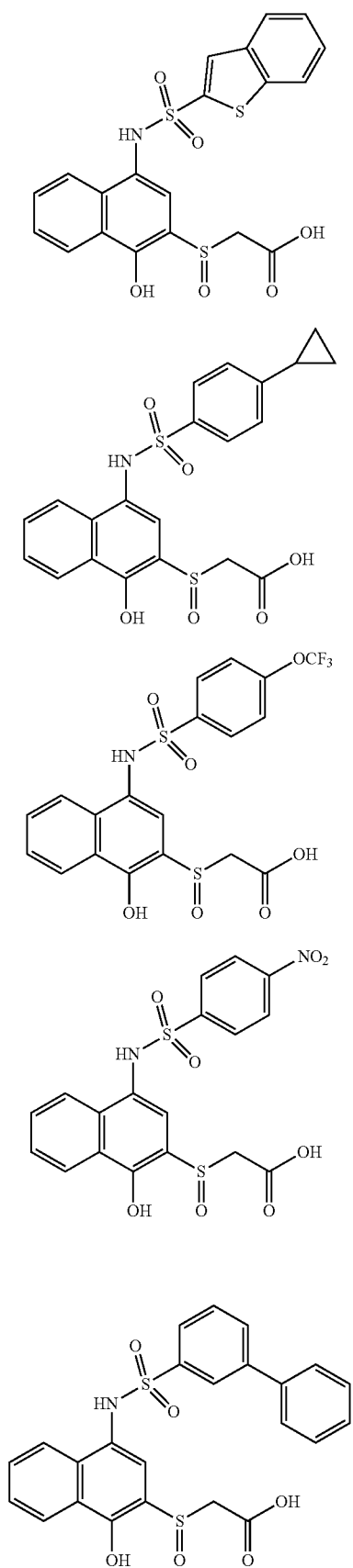
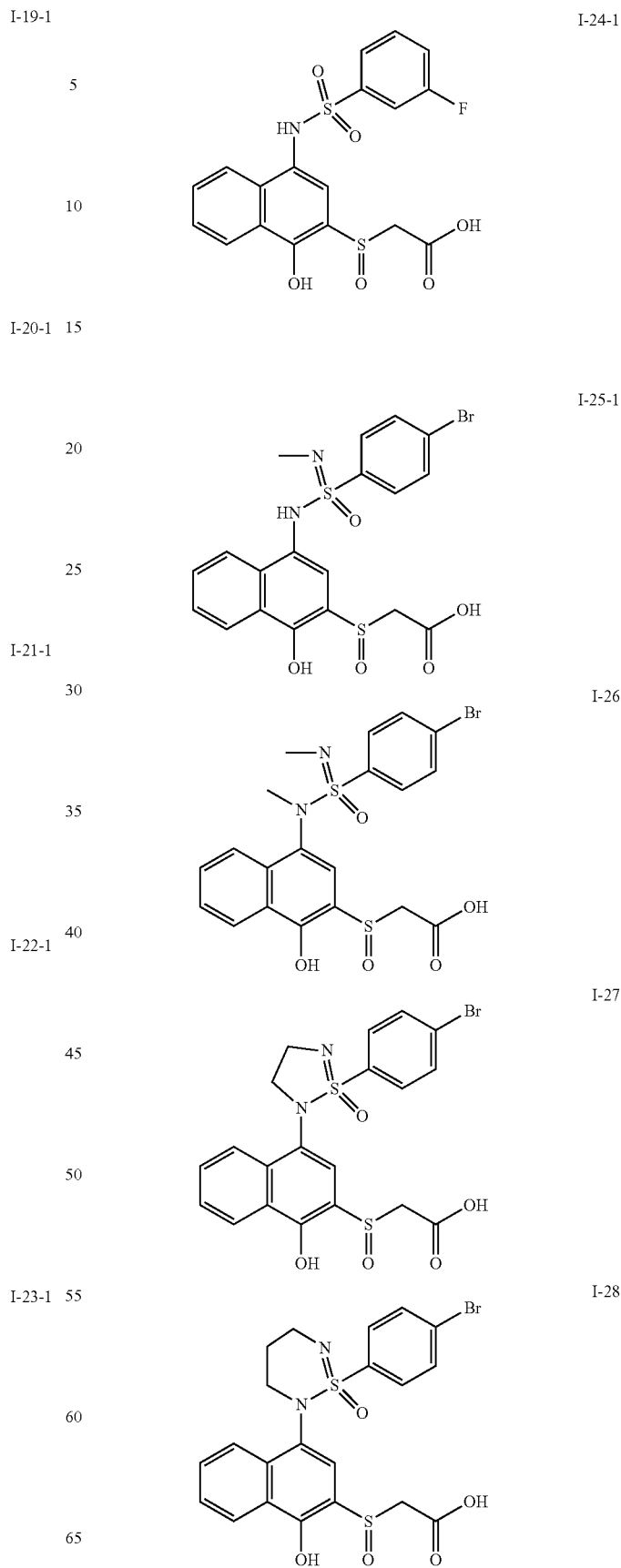

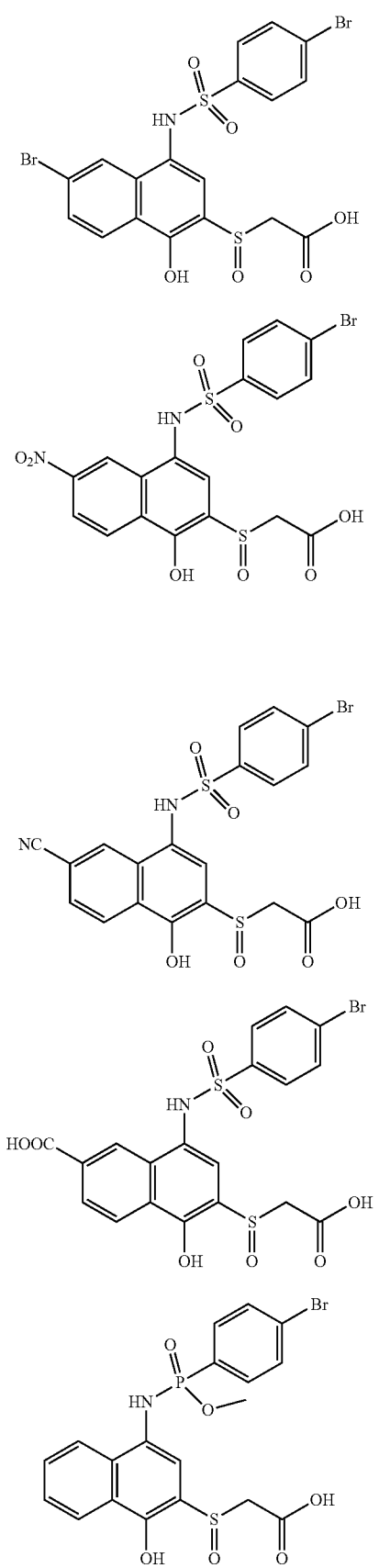
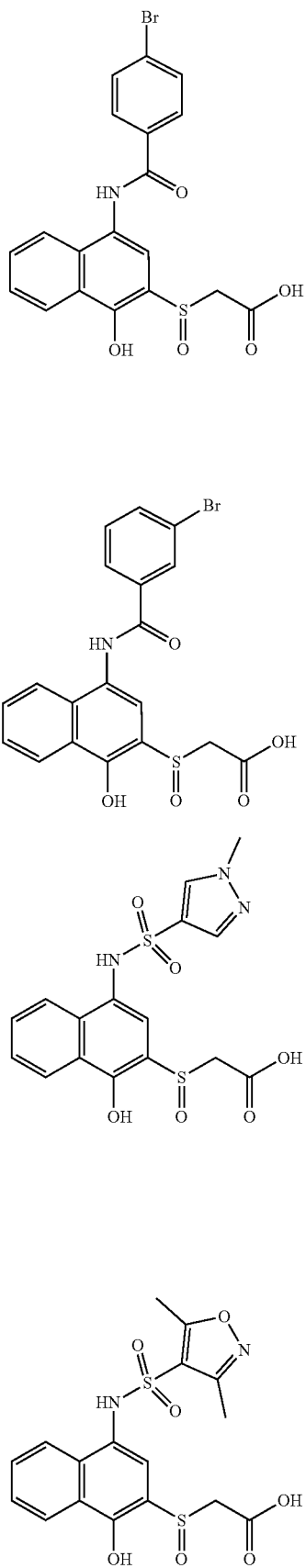

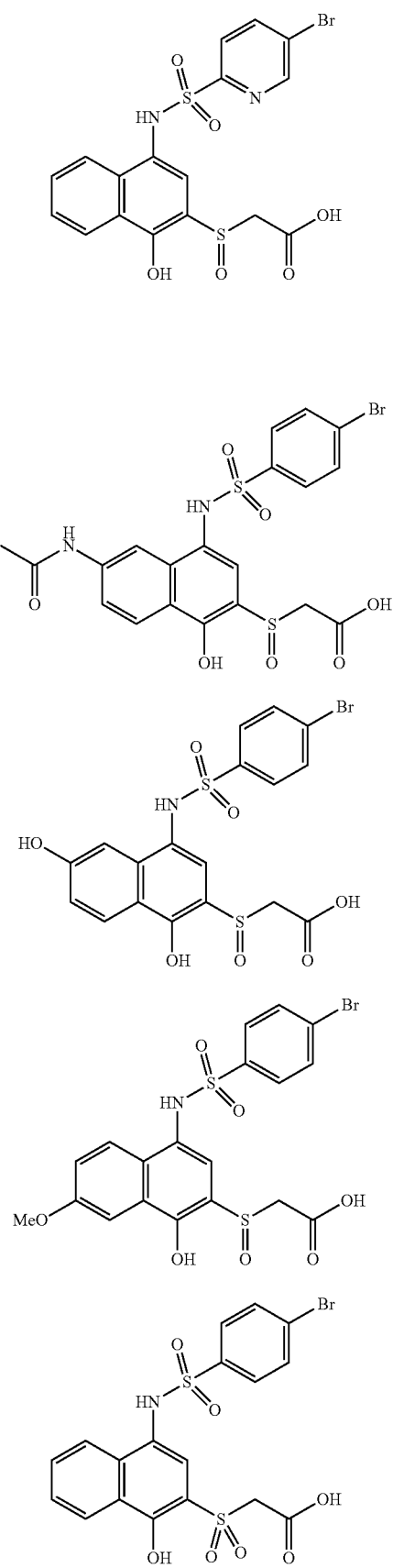
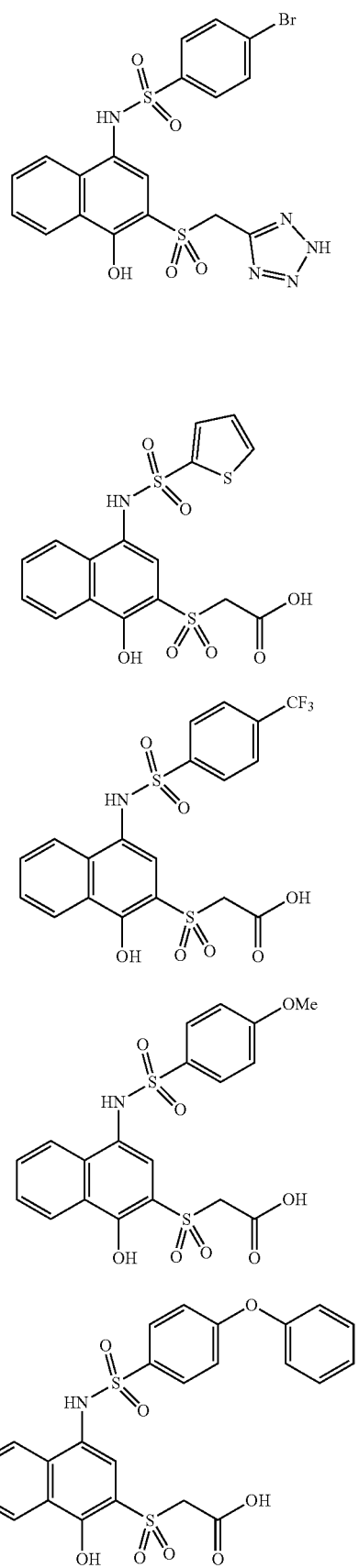

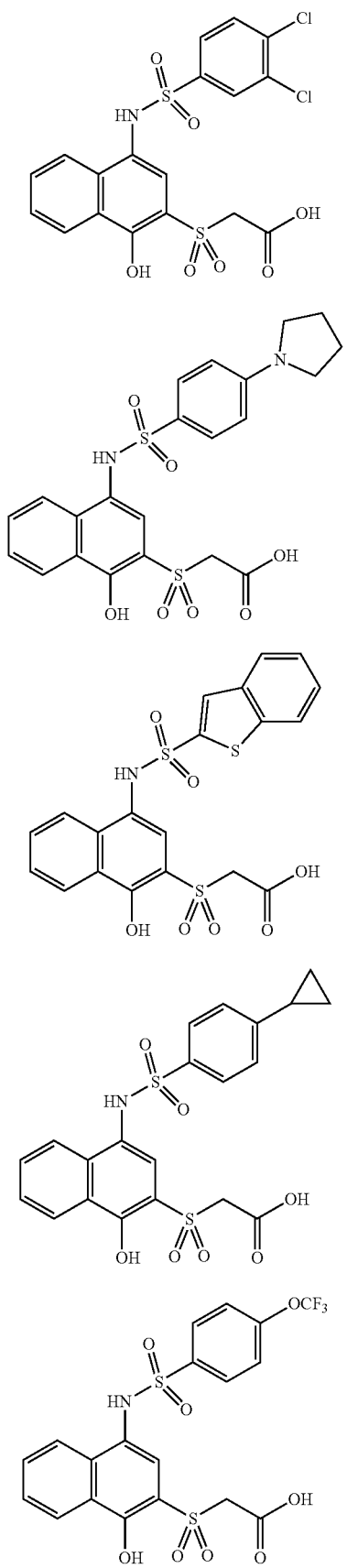
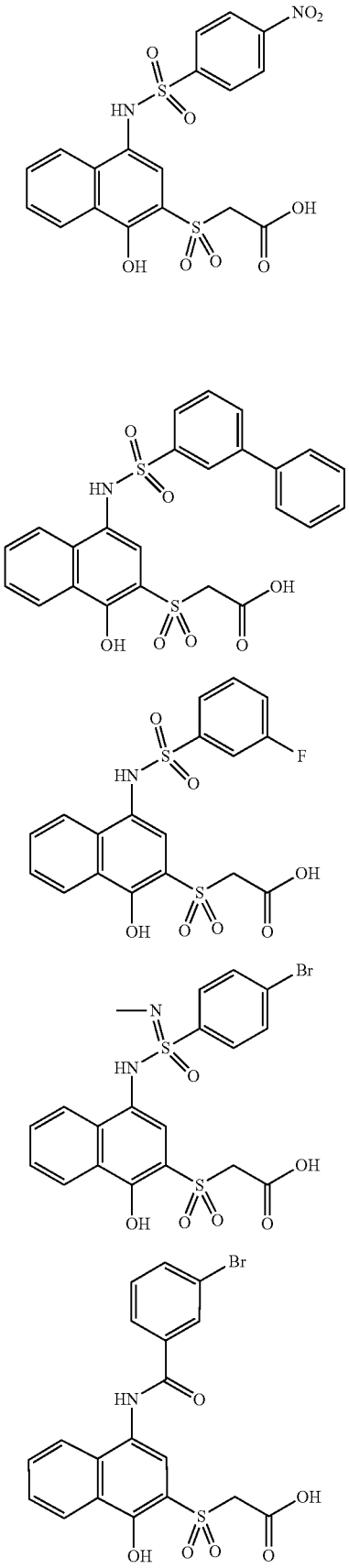

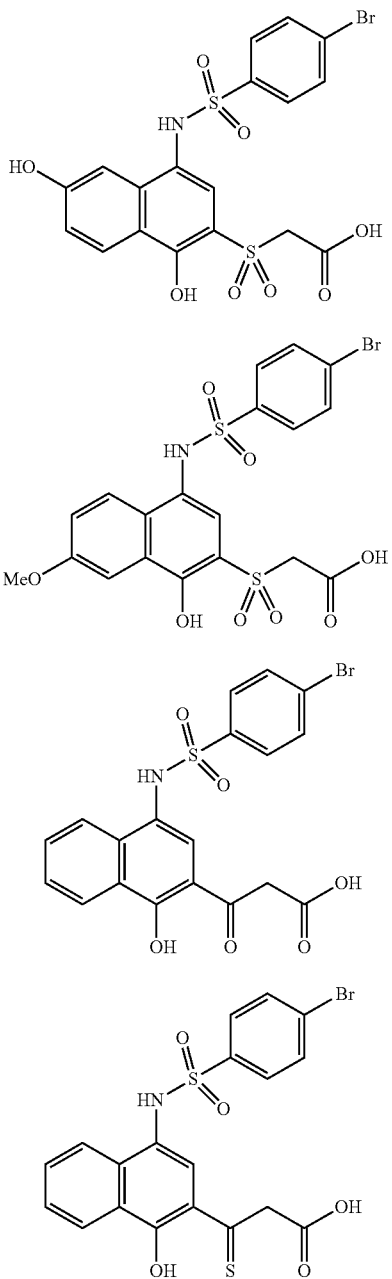

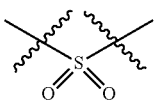 and 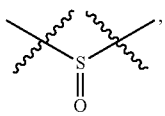, for example, Z is

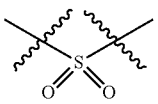 or 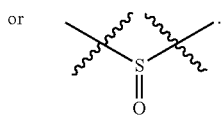.

In some preferred embodiments, Z is

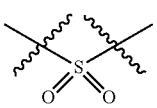 or 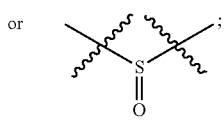;

$R^1$ is hydrogen or $C_{1\sim6}$ alkyl;

$R^2$ is hydrogen, $C_{1\sim6}$ alkyl, three to six-membered cycloalkyl, three to six-membered epoxyalkyl, phenyl or $C_{1\sim6}$ alkyl substituted phenyl;

$R^3$ is

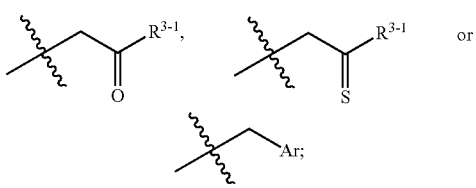

where $R^{3-1}$ is hydrogen, hydroxyl, $C_{1\sim6}$ alkyl, $C_{1\sim6}$ alkoxy, three to six-membered cycloalkyl, three to six-membered epoxyalkyl, amino, $C_{1\sim6}$ amido, —$CH_2C(O)R^{3-2}$, —$CH_2C(O)OR^{3-2}$ or —$CH_2C(O)N(R^{3-2}R^{3-2a})$, $R^{3-2}$ and $R^{3-2a}$ are independently hydrogen, $C_{1\sim6}$ alkyl or three to six-membered cycloalkyl, Ar is phenyl, naphthyl, 5- or 6-membered monocyclic heteroaryl, 8 to 10-membered fused bicyclic heteroaryl, phenyl with at least one hydrogen atom substituted by $R^{3-3}$, naphthyl with at least one hydrogen atom substituted by $R^{3-3}$, 5- or 6-membered monocyclic heteroaryl with at least one hydrogen atom substituted by $R^{3-3}$, 8 to 10-membered fused bicyclic heteroaryl with at least one hydrogen atom substituted by $R^{3-3}$, and the $R^{3-3}$ is hydrogen, halogen, $C_{1\sim6}$ alkyl, three to six-membered cycloalkyl, hydroxyl, $C_{1\sim6}$ alkoxy, three to six-membered epoxyalkyl, $C_{1\sim6}$ haloalkyl, $C_{2\sim6}$ alkenyl, $C_{2\sim6}$ alkynyl, —$N(R^{3-3a}R^{3-3b})$ or phenyl, $R^{3-3a}$ and $R^{3-3b}$ are each independently hydrogen, $C_{1\sim6}$ alkyl or three to six-membered cycloalkyl;

The inventor of the present invention has surprisingly found that when Z is

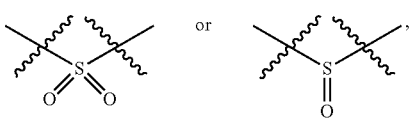

the selectivity of inducing autophagy in damaged mitochondria can be significantly improved, while the metabolic stability can be significantly improved. Therefore, in some more preferred embodiments of the present invention, Z is selected from $R^4$ is

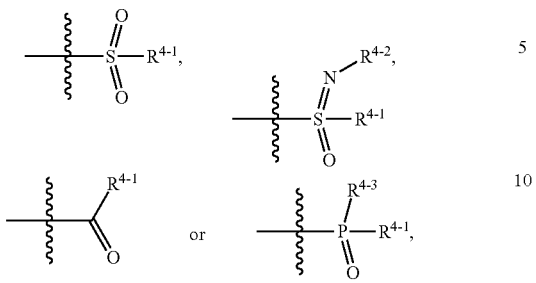

where $R^{4-1}$ is phenyl, naphthyl, phenyl with at least one hydrogen atom substituted by $R^{4-11}$, 5- or 6-membered monocyclic heteroaryl, 5- or 6-membered monocyclic heteroaryl with at least one hydrogen atom substituted by $R^{4-11}$ or 8 to 10-membered fused bicyclic heteroaryl, or 8 to 10-membered fused bicyclic heteroaryl with at least one hydrogen atom is substituted by $R^{4-11}$, and the $R^{4-11}$ is hydrogen, halogen, nitro, nitrile group, hydroxyl, $C_{1\sim6}$ alkyl, three to six-membered cycloalkyl, $C_{1\sim6}$ alkoxy, —N($R^{4-1a}R^{4-1b}$), phenyl, $C_{1\sim6}$ haloalkyl, $C_{1\sim6}$ haloalkoxy, —C(O)O$R^{4-12}$, —C(O)$R^{4-12}$, —C(O)N($R^{4-1a}R^{4-1b}$), —S(O)$_2R^{4-12}$, —S(O)$R^{4-12}$, —OC(O)$R^{4-12}$, —OC(O)O$R^{4-12}$ or

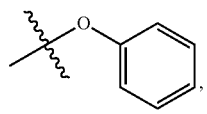

$R^{4-12}$, $R^{4-1a}$ and $R^{4-1b}$ are each independently hydrogen, $C_{1\sim6}$ alkyl, three to six-membered cycloalkyl, $C_{2\sim6}$ alkenyl, $C_{2\sim6}$ alkynyl, $C_{1\sim6}$ alkyl with at least one hydrogen substituted by halogen, $C_{2\sim6}$ alkenyl with at least one hydrogen substituted by halogen, three to six-membered cycloalkyl with at least one hydrogen substituted by halogen, or $C_{2\sim6}$ alkynyl with at least one hydrogen substituted by halogen, and $R^{4-1a}$ and $R^{4-1b}$ can be bonded to each other to form a ring, $R^{4-2}$ is $C_{1\sim6}$ alkyl or three to six-membered cycloalkyl, or when $R^2$ is $C_{1\sim6}$ alkyl, $R^{4-2}$ and $R^2$ are bonded to form a 4 to 8-membered ring, $R_{4-3}$ is $C_{1\sim6}$ alkyl or $C_{1\sim6}$ alkoxy;

when the number of $R^5$ is not 0, each is independently selected from halogen, nitro, nitrile group, —N$^+$($R^{5-1}$)$_3$, $C_{1\sim6}$ haloalkyl, —C(O)O$R^{5-1}$, —C(O)$R^{5-1}$, —C(O)N($R^{5-1}R^{5-1a}$), —S(O)$_2R^{5-1}$, —S(O)$R^{5-1}$, —S(O)$_2$N($R^{5-1}R^{5-1a}$), —S(O)N($R^{5-1}R^{5-1a}$), —N=C($R^{5-1}R^{5-1a}$), hydroxyl, $C_{1\sim6}$ alkyl, phenyl, phenyl with at least one hydrogen substituted by $R^{5-1}$, $C_{1\sim6}$ alkoxy, —N($R^{5-1}R^{5-1a}$), —N($R^{5-1}$)C(O)$R^{5-1a}$, —N($R^{5-1}$)C(O)O$R^{5-1a}$, —N($R^{5-1}$)C(O)N($R^{5-1a} R^{5-1b}$), —OC(O)$R^{5-1}$, —OC(O)O$R^{5-1}$, —OC(O)N($R^{5-1}R^{5-1a}$) and —S$R^{5-1}$, wherein $R^{5-1}$, $R^{5-1a}$ and $R^{5-1b}$ are each independently hydrogen, $C_{1\sim6}$ alkyl, $C_{2\sim6}$ alkenyl, $C_{2\sim6}$ alkynyl, $C_{1\sim6}$ alkyl with at least one hydrogen substituted by halogen, $C_{2\sim6}$ alkenyl with at least one hydrogen substituted by halogen, or $C_{2\sim6}$ alkynyl with at least one hydrogen substituted by halogen.

Based on the favourable effect on the compounds with enhanced medicinal effects, in some preferred embodiments, the compound has a structure represented by formula (II);

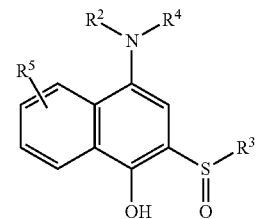

wherein $R^2$ is hydrogen, $C_{1\sim4}$ alkyl, three to six-membered cycloalkyl or four to six-membered epoxyalkyl;

$R^3$ is

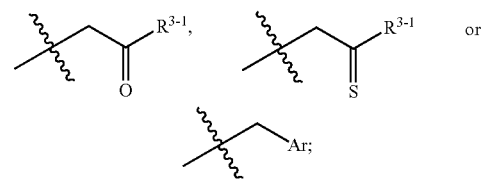

where $R^{3-1}$ is hydrogen, hydroxyl, $C_{1\sim4}$ alkyl, $C_{1\sim4}$ alkoxy, three to six-membered cycloalkyl, three to six-membered epoxyalkyl, —N($R^{3-2}R^{3-2a}$), —CH$_2$C(O)$R^{3-2}$, —CH$_2$C(O)O$R^{3-2}$ or —CH$_2$C(O)N$R^{3-2}R^{3-2a}$, $R^{3-2}$ and $R^{3-2a}$ are each independently hydrogen, $C_{1\sim4}$ alkyl or three to six-membered cycloalkyl, Ar is phenyl, 5- or 6-membered monocyclic heteroaryl, 5- or 6-membered monocyclic heteroaryl with at least one hydrogen atom substituted by $R^{3-3}$, and the $R^{3-3}$ is hydrogen, halogen, $C_{1\sim4}$ alkyl, three to six-membered cycloalkyl, hydroxyl, $C_{1\sim4}$ alkoxy, three to six-membered epoxyalkyl, $C_{1\sim4}$ haloalkyl, $C_{2\sim4}$ alkenyl, $C_{2\sim4}$ alkyne, —N($R^{3-3a}R^{3-3b}$) or phenyl, $R^{3-3a}$ and $R^{3-3b}$ are independently hydrogen, $C_{1\sim4}$ alkyl or three to six-membered cycloalkyl;

$R^4$ is

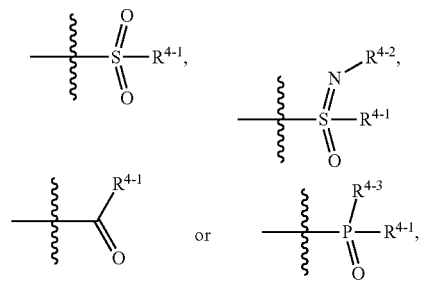

among them, $R^{4-1}$ is phenyl, phenyl in which at least one hydrogen atom is substituted by $R^{4-11}$, 5- or 6-membered monocyclic heteroaryl, and 5- or 6-membered monocyclic heteroaryl with at least one hydrogen atom substituted by $R^{4-11}$, 8 to 10-membered fused bicyclic heteroaryl, 8 to 10-membered fused bicyclic heteroaryl with at least one hydrogen atom substituted by $R^{4-11}$, and the $R^{4-11}$ is hydrogen, halogen, nitro, $C_{1\sim4}$ alkyl, three to six-membered cycloalkyl, $C_{1\sim4}$ alkoxy, —N($R^{4-1a}R^{4-1b}$), phenyl, $C_{1\sim4}$ haloalkyl, $C_{1\sim4}$ haloalkoxy or

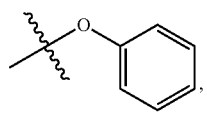

$R^{4-1a}$ and $R^{4-1b}$ are each independently hydrogen, $C_{1\text{~}4}$ alkyl or three to six-membered cycloalkyl, and $R^{4-1a}$ and $R^{4-1b}$ can be bonded to each other to form a ring, $R^{4-2}$ is $C_{1\text{~}4}$ alkyl, three to six-membered cycloalkyl, or when $R^2$ is $C_{1\text{~}4}$ alkyl, $R^{4-2}$ and $R^2$ are bonded to form a 4 to 8-membered ring, $R_{4\text{-}3}$ is $C_{1\text{~}4}$ alkyl or $C_{1\text{~}4}$ alkoxy;

when the number of $R^5$ is not 0, each is independently selected from halogen, nitro, nitrile group, —N$^+$($R^{5-1}$)$_3$, $C_{1\text{~}4}$ haloalkyl, —C(O)OR$^{5-1}$, —C(O)R$^{5-1}$, —C(O)N(R$^{5-1}$R$^{5-1a}$), —S(O)$_2$R$^{5-1}$, —S(O)R$^{5-1}$, —N=C(R$^{5-1}$R$^{5-1a}$), hydroxyl, $C_{1\text{~}4}$ alkyl, phenyl, phenyl with at least one hydrogen substituted by R$^{5-1}$, $C_{1\text{~}4}$ alkoxy, —N(R$^{5-1}$R$^{5-1a}$), —N(R$^{5-1}$)C(O)R$^{5-1a}$, —OC(O)R$^{5-1}$, —OC(O)N(R$^{5-1}$R$^{5-1a}$) or —SR$^{5-1}$, wherein R$^{5-1}$, R$^{5-1a}$ and R$^{5-1b}$ are independently hydrogen, $C_{1\text{~}4}$ alkyl, $C_{2\text{~}4}$ alkenyl, $C_{2\text{~}4}$ alkynyl, $C_{1\text{~}4}$ alkyl with at least one hydrogen substituted by halogen, $C_{2\text{~}4}$ alkenyl with at least one hydrogen substituted by halogen, or $C_{2\text{~}4}$ alkynyl with at least one hydrogen substituted by halogen.

In some more preferred embodiments, the compound has a structure represented by formula (II);

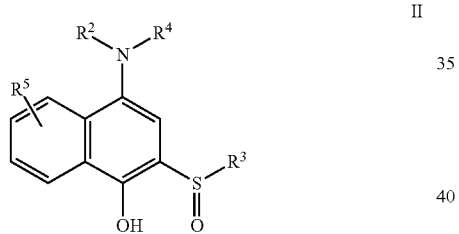

II wherein $R^2$ is hydrogen, $C_{1\text{~}4}$ alkyl, three to six-membered cycloalkyl or four to six-membered epoxyalkyl;

$R^3$ is

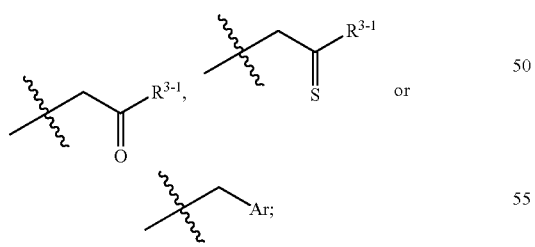

where $R^{3-1}$ is hydrogen, hydroxyl, $C_{1\text{~}4}$ alkyl, $C_{1\text{~}4}$ alkoxy, three to six-membered cycloalkyl, three to six-membered epoxyalkyl, —N(R$^{3-2}$R$^{3-2a}$), —CH$_2$C(O)R$^{3-2}$, —CH$_2$C(O)OR$^{3-2}$, —CH$_2$C(O)NR$^{3-2}$R$^{3-2a}$ $R^{3-2}$ and $R^{3-2a}$ are each independently hydrogen, $C_{1\text{~}4}$ alkyl or three to six-membered cycloalkyl, Ar is phenyl, 5- or 6-membered monocyclic heteroaryl, 5- or 6-membered monocyclic heteroaryl with at least one hydrogen atom substituted by R$^{3-3}$, and the R$^{3-3}$ is hydrogen, halogen, $C_{1\text{~}4}$ alkyl, three to six-membered cycloalkyl, hydroxyl, $C_{1\text{~}4}$ alkoxy, three to six-membered epoxyalkyl, $C_{1\text{~}4}$ haloalkyl, $C_{2\text{~}4}$ alkenyl, $C_{2\text{~}4}$ alkyne, —N(R$^{3-3a}$R$^{3-3b}$) or phenyl, R$^{3-3a}$ and R$^{3-3b}$ are each independently hydrogen, $C_{1\text{~}4}$ alkyl or three to six-membered cycloalkyl;

$R^4$ is

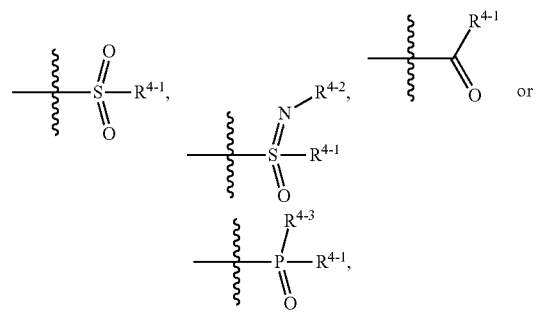

where $R^{4-1}$ is phenyl, phenyl with at least one hydrogen atom substituted by R$^{4-11}$, 5- or 6-membered monocyclic heteroaryl, and 5- or 6-membered monocyclic heteroaryl with at least one hydrogen atom substituted by R$^{4-11}$, 8 to 10-membered fused bicyclic heteroaryl, 8 to 10-membered fused bicyclic heteroaryl with at least one hydrogen atom substituted by R$^{4-11}$, and the R$^{4-11}$ is hydrogen, halogen, nitro, $C_{1\text{~}4}$ alkyl, three to six-membered cycloalkyl, $C_{1\text{~}4}$ alkoxy, —N(R$^{4-1a}$R$^{4-1b}$), phenyl, $C_{1\text{~}4}$ haloalkyl, $C_{1\text{~}4}$ haloalkoxy or

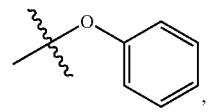 [SMILES: *Oc1ccccc1]

$R^{4-1a}$ and $R^{4-1b}$ are each independently hydrogen, $C_{1\text{~}4}$ alkyl or three to six-membered cycloalkyl, and $R^{4-1a}$ and $R^{4-1b}$ can be bonded to each other to form a ring, $R^{4-2}$ is $C_{1\text{~}4}$ alkyl, three- to six-membered cycloalkyl, or when $R^2$ is $C_{1\text{~}4}$ alkyl, $R^{4-2}$ and $R^2$ are bonded to form a 4 to 8-membered ring, $R_{4\text{-}3}$ is $C_{1\text{~}4}$ alkyl or $C_{1\text{~}4}$ alkoxy;

when the number of $R^5$ is not 0, each is independently selected from halogen, nitro, nitrile group, —N$^+$($R^{5-1}$)$_3$, $C_{1\text{~}4}$ haloalkyl, —C(O)OR$^{5-1}$, —C(O)R$^{5-1}$, —C(O)N(R$^{5-1}$R$^{5-1a}$), —S(O)$_2$R$^{5-1}$, —S(O)R$^{5-1}$ and —N=C(R$^{5-1}$R$^{5-1a}$), wherein R$^{5-1}$ and R$^{5-1a}$ are each independently hydrogen, $C_{1\text{~}4}$ alkyl, $C_{2\text{~}4}$-alkenyl, $C_{2\text{~}4}$ alkynyl, $C_{1\text{~}4}$ alkyl with at least one hydrogen substituted by halogen, $C_{2\text{~}4}$ alkenyl with at least one hydrogen substituted by halogen, or $C_{2\text{~}4}$ alkynyl with at least one hydrogen substituted by halogen.

Based on the improvement of the compound's ability to selectively induce autophagy, lower toxicity and better metabolic stability, in some preferred embodiments, the compound has a structure represented by formula (III);

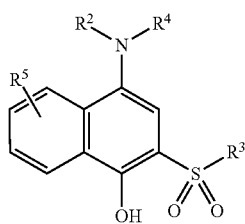

wherein $R^2$ is hydrogen, $C_{1-4}$ alkyl, three to six-membered cycloalkyl or four to six-membered epoxyalkyl; $R^3$ is

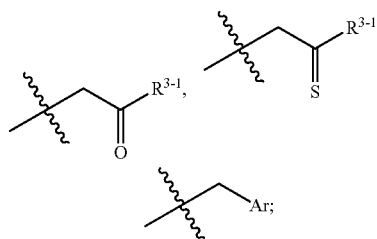

where $R^{3-1}$ is hydrogen, hydroxyl, $C_{1-4}$ alkyl, $C_{1-4}$ alkoxy, three to six-membered cycloalkyl, three to six-membered epoxyalkyl, $-N(R^{3-2}R^{3-2a})$, $-CH_2C(O)R^{3-2}$, $-CH_2C(O)OR^{3-2}$ or $-CH_2C(O)NR^{3-2}R^{3-2a}$, $R^{3-2}$ and $R^{3-2a}$ are each independently hydrogen, $C_{1-4}$ alkyl or three to six-membered cycloalkyl, Ar is phenyl, 5- or 6-membered monocyclic heteroaryl, 5- or 6-membered monocyclic heteroaryl with at least one hydrogen atom substituted by $R^{3-3}$, and the $R^{3-3}$ is hydrogen, halogen, $C_{1-4}$ alkyl, three to six-membered cycloalkyl, hydroxyl, $C_{1-4}$ alkoxy, three to six-membered epoxyalkyl, $C_{1-4}$ haloalkyl, $C_{2-4}$ alkenyl, $C_{2-4}$ alkyne, $-N(R^{3-3a}R^{3-3b})$ or phenyl, $R^{3-3a}$ and $R^{3-3b}$ are each independently hydrogen, $C_{1-4}$ alkyl or three to six-membered cycloalkyl;

$R^4$ is

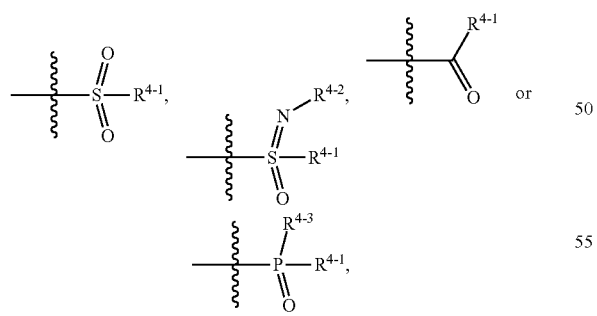

where $R^{4-1}$ is phenyl, phenyl with at least one hydrogen atom substituted by $R^{4-11}$, 5- or 6-membered monocyclic heteroaryl, and 5- or 6-membered monocyclic heteroaryl with at least one hydrogen atom substituted by $R^{4-11}$, 8- to 10-membered fused bicyclic heteroaryl, or 8- to 10-membered fused bicyclic heteroaryl with at least one hydrogen atom substituted by $R^{4-11}$, and the $R^{4-11}$ is hydrogen, halogen, nitro, $C_{1-4}$ alkyl, three to six-membered cycloalkyl, $C_{1-4}$ alkoxy, $-N(R^{4-1a}R^{4-1b})$, phenyl, $C_{1-4}$ haloalkyl, $C_{1-4}$ haloalkoxy or

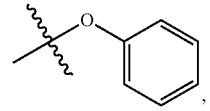 [SMILES: *Oc1ccccc1]

, $R^{4-1a}$ and $R^{4-1b}$ are each independently hydrogen, $C_{1-4}$ alkyl or three to six-membered cycloalkyl, and $R^{4-1a}$ and $R^{4-1b}$ can be bonded to each other to form a ring, $R^{4-2}$ is $C_{1-4}$ alkyl or a three to six-membered cycloalkyl, or when $R^2$ is $C_{1-4}$ alkyl, $R^{4-2}$ and $R^2$ are bonded to form a 4 to 8-membered ring, $R_{4-3}$ is $C_{1-4}$ alkyl or $C_{1-4}$ alkoxy;

when the number of $R^5$ is not 0, each is independently selected from halogen, nitro, nitrile group, $-N^+(R^{5-1})_3$, $C_{1-4}$ haloalkyl, $-C(O)OR^{5-1}$, $-C(O)R^{5-1}$, $-C(O)N(R^{5-1}R^{5-1a})$, $-S(O)_2R^{5-1}$, $-S(O)R^{5-1}$, $-N=C(R^{5-1}R^{5-1a})$, hydroxyl, $C_{1-4}$ alkyl, phenyl, phenyl with at least one hydrogen substituted by $R^{5-1}$, $C_{1-4}$ alkoxy, $-N(R^{5-1}R^{5-1a})$, $-N(R^{5-1})C(O)R^{5-1a}$, $-OC(O)R^{5-1}$, $-OC(O)N(R^{5-1}R^{5-1a})$ and $-SR^{5-1}$, wherein $R^{5-1}$, $R^{5-1a}$ and $R^{5-1b}$ are each independently hydrogen, $C_{1-4}$ alkyl, $C_{2-4}$ alkenyl, $C_{2-4}$ alkynyl, $C_{1-4}$ alkyl with at least one hydrogen substituted by halogen, $C_{2-4}$ alkenyl with at least one hydrogen substituted by halogen, or $C_{2-4}$ alkynyl with at least one hydrogen substituted by halogen.

In some more preferred embodiments, the compound has a structure represented by formula (III);

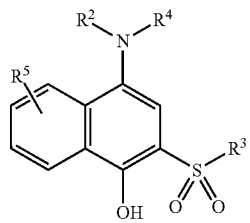

wherein $R^2$ is hydrogen, $C_{1-4}$ alkyl, three to six-membered cycloalkyl or four to six-membered epoxyalkyl; $R^3$ is

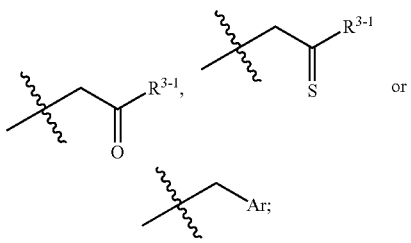

where $R^{3-1}$ is hydrogen, hydroxyl, $C_{1-4}$ alkyl, $C_{1-4}$ alkoxy, three to six-membered cycloalkyl, three to six-membered epoxyalkyl, $-N(R^{3-2}R^{3-2a})$, $-CH_2C(O)R^{3-2}$, $-CH_2C(O)OR^{3-2}$ or $-CH_2C(O)NR^{3-2}R^{3-2a}$, $R^{3-2}$ and $R^{3-2a}$ are each independently hydrogen, $C_{1-4}$ alkyl or three to six-membered cycloalkyl, Ar is phenyl, 5- or 6-membered monocyclic heteroaryl, or 5- or 6-membered monocyclic heteroaryl with at least one hydrogen atom substituted by $R^{3-3}$, and the $R^{3-3}$ is hydrogen, halogen, $C_{1\text{-}4}$ alkyl, three to six-membered cycloalkyl, hydroxyl, $C_{1\text{-}4}$ alkoxy, three to six-membered epoxyalkyl, $C_{1\text{-}4}$ haloalkyl, $C_{2\text{-}4}$ alkenyl, $C_{2\text{-}4}$ alkyne, $-N(R^{3-3a}R^{3-3b})$ or phenyl, $R^{3-3a}$ and $R^{3-3b}$ are each independently hydrogen, $C_{1\text{-}4}$ alkyl or three to six-membered cycloalkyl;

$R^4$ is

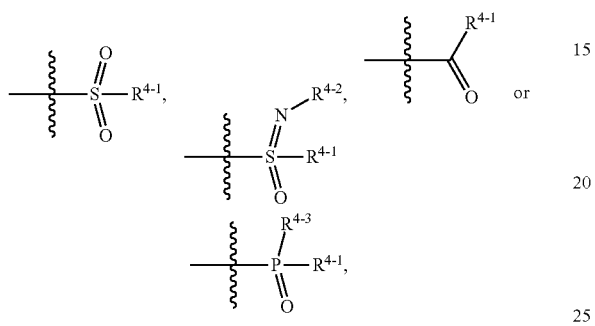

where $R^{4-1}$ is phenyl, phenyl with at least one hydrogen atom substituted by $R^{4-11}$, 5- or 6-membered monocyclic heteroaryl, and 5- or 6-membered monocyclic heteroaryl with at least one hydrogen atom substituted by $R^{4-11}$, 8 to 10-membered fused bicyclic heteroaryl, or 8 to 10-membered fused bicyclic heteroaryl with at least one hydrogen atom substituted by $R^{4-11}$, and the $R^{4-11}$ is hydrogen, halogen, nitro, $C_{1\text{-}4}$ alkyl, three to six-membered cycloalkyl, $C_{1\text{-}4}$ alkoxy, $-N(R^{4-1a}R^{4-1b})$, phenyl, $C_{1\text{-}4}$ haloalkyl, $C_{1\text{-}4}$ haloalkoxy or

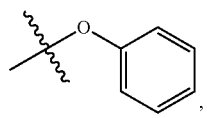, $R^{4-1a}$ and $R^{4-1b}$ are each independently hydrogen, $C_{1\text{-}4}$ alkyl or three to six-membered cycloalkyl, and $R^{4-1a}$ and $R^{4-1b}$ can be bonded to each other to form a ring, $R^{4-2}$ is $C_{1\text{-}4}$ alkyl or three- to six-membered cycloalkyl, or when $R^2$ is $C_{1\text{-}4}$ alkyl, $R^{4-2}$ and $R^2$ are bonded to form a 4 to 8-membered ring, $R_{4\text{-}3}$ is $C_{1\text{-}4}$ alkyl or $C_{1\text{-}4}$ alkoxy;

when the number of $R^5$ is not 0, each is independently selected from hydroxyl, $C_{1\text{-}4}$ alkyl, phenyl, phenyl with at least one hydrogen substituted by $R^{5-1}$, $C_{1\text{-}4}$ alkoxy, $-N(R^{5-1}R^{5-1a})$, $-N(R^{5-1})C(O)R^{5-1a}$, $-OC(O)R^{5-1}$, $-OC(O)N(R^{5-1}R^{5-1a})$ and $-SR^{5-1}$, wherein $R^{5-1}$, $R^{5-1a}$ and $R^{5-1b}$ are each independently hydrogen, $C_{1\text{-}4}$ alkyl, $C_{2\text{-}4}$ alkenyl, $C_{2\text{-}4}$ alkynyl, $C_{1\text{-}4}$ alkyl with at least one hydrogen substituted by halogen, $C_{2\text{-}4}$ alkenyl with at least one hydrogen substituted by halogen, or $C_{2\text{-}4}$ alkynyl with at least one hydrogen substituted by halogen.

In the aforementioned compounds of the formula I to the Formula III, more preferably, $R^1$ is hydrogen or methyl, more preferably hydrogen.

In the aforementioned compounds of the Formula I to the Formula III, more preferably, $R^2$ is hydrogen, $C_{1\text{-}6}$ alkyl (preferably methyl), three to six-membered cycloalkyl (preferably cyclopropyl) or three to six-membered epoxyalkyl (preferably oxetane).

In the aforementioned compounds of the Formula I to the Formula III, more preferably, $R^3$ is selected from $-CH_2-COOH$, $-CH_2-CONH_2$,

wherein, Ar is 5- or 6-membered monocyclic heteroaryl, more preferably 5- or 6-membered nitrogen-containing monocyclic heteroaryl, more preferably a triazolyl (such as

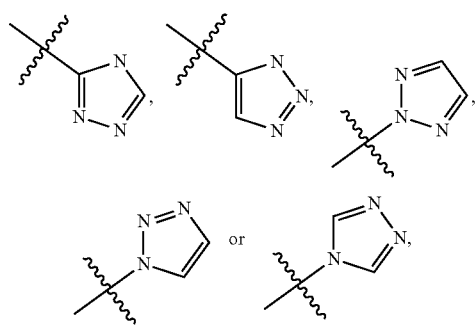

especially is

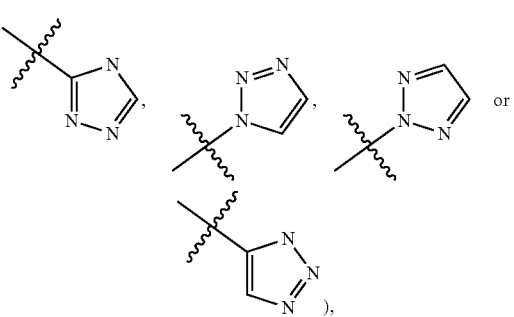

tetrazolyl (for example

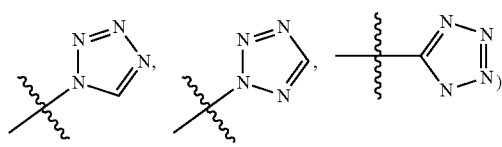 [SMILES: *n1cnnn1 ; *n1ncnn1 ; *c1nnn[nH]1]

or phenyl.

In the aforementioned compounds of the Formula I to the Formula III, more preferably, $R^4$ is:

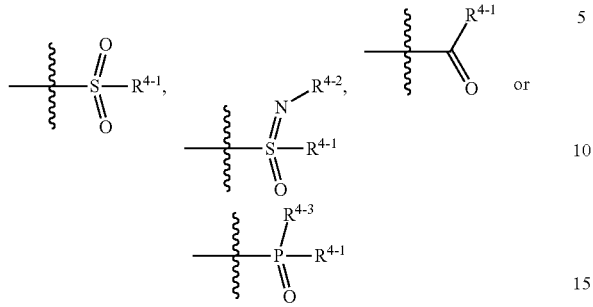

wherein $R^{4-1}$ is selected from phenyl, 5- or 6-membered monocyclic heteroaryl (such as thienyl, pyrazolyl, isoxazolyl, pyridyl) and 8 to 10-membered fused bicyclic heteroaryl (such as benzothienyl), each of the above groups is optionally substituted by a group selected from the following: halogen, nitro, phenyl, nitrile, hydroxyl, $C_{1\sim6}$ alkyl, three to six-membered cycloalkyl, $C_{1\sim6}$ alkoxy, $C_{1\sim6}$ haloalkyl, $C_{1\sim6}$ haloalkoxy,

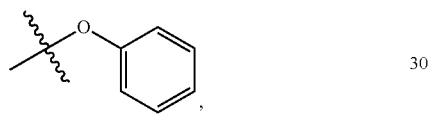

-N($R^{4-1a}R^{4-1b}$) ($R^{4-1a}$ and $R^{4-1b}$ can be bonded to each other to form a ring, such as a pyrrolidine ring);
$R^{4-2}$ is hydrogen, $C_{1\sim6}$ alkyl, three to six-membered cycloalkyl, or when $R^2$ is $C_{1\sim6}$ alkyl, $R^{4-2}$ and $R^2$ are bonded to form a 4 to 8-membered (e.g. 5-membered or 6-membered) ring;
$R^{4-3}$ is hydrogen, $C_{1\sim6}$ alkyl or $C_{1\sim6}$ alkoxy.
$R^{4-1a}$, $R^{4-1b}$, $R^{4-2}$, $R^{4-3}$, $R^5$ are as defined in the context of this specification.

In the aforementioned compounds of the Formula I to the Formula III, preferably, the number of $R^5$ is 0~2 (especially 0~1), and when the number of $R^5$ is not 0, each is independently selected from hydroxyl, $C_{1\sim4}$ alkyl, $C_{1\sim4}$ alkoxy, nitro, —COOH, —NHCO—$C_{1\sim4}$ alkyl (for example —NHCO—CH$_3$).

In some more preferred embodiments, the compounds of the invention are selected from any of the following compounds, or pharmaceutically acceptable salts, stereoisomers, solvates or prodrugs thereof:

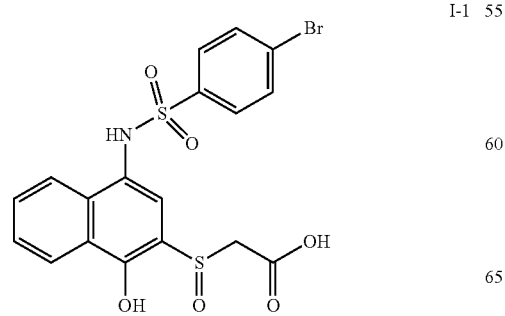

I-1

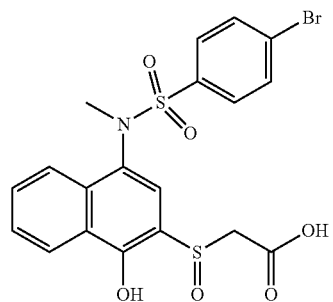

I-2

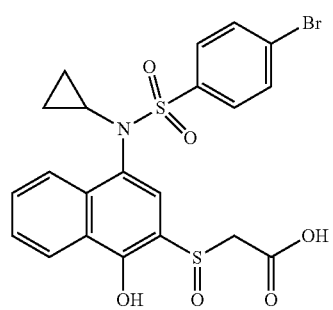

I-3

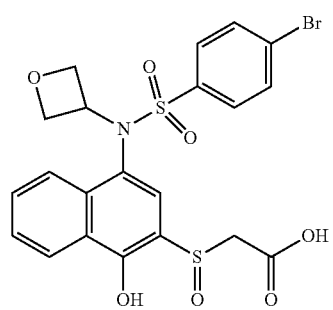

I-4

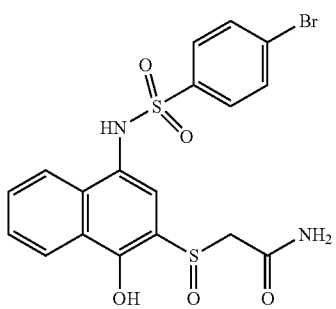

I-5

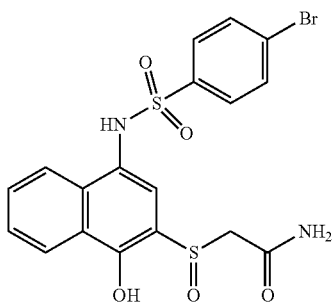

I-6

| | |
|---|---|
| I-7-1 | I-11-1 |
| I-8 | I-11-2 |
| I-9-1 | I-12 |
| I-9-2 | I-13-1 |
| I-10 | I-14-1 |

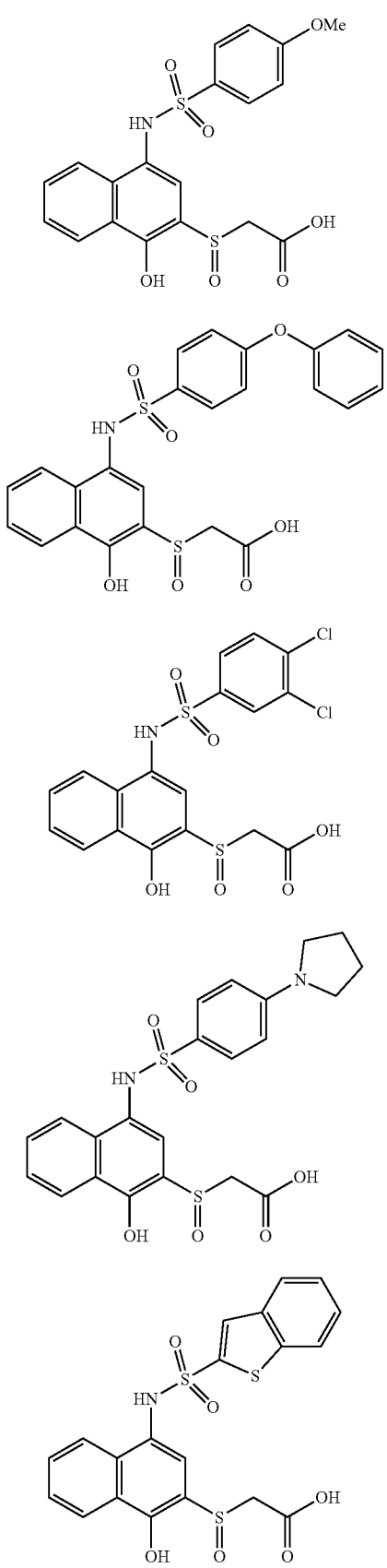
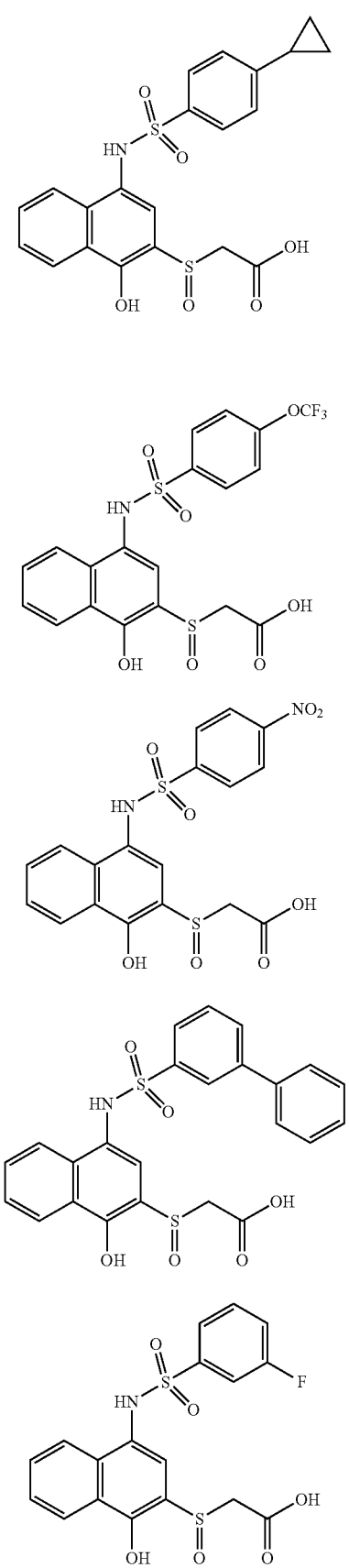

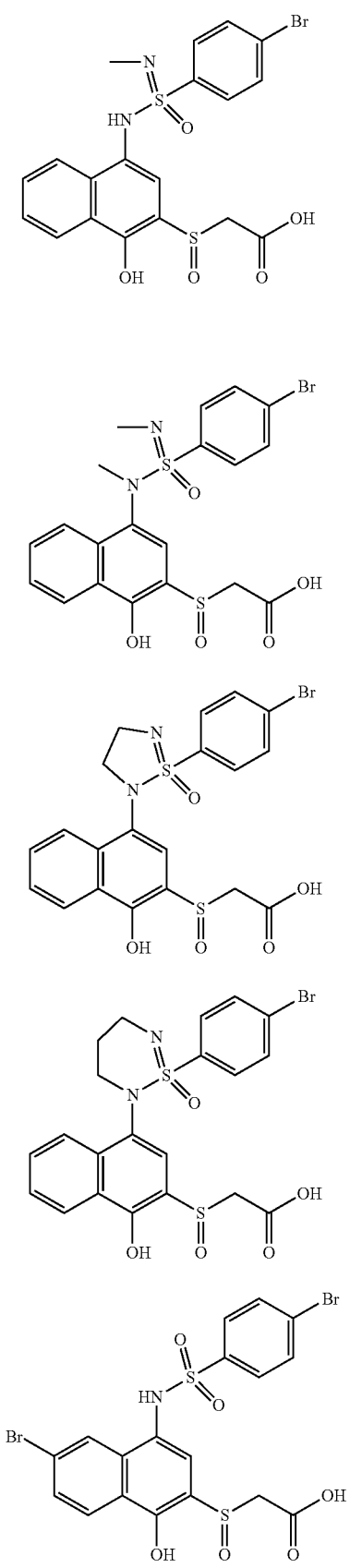
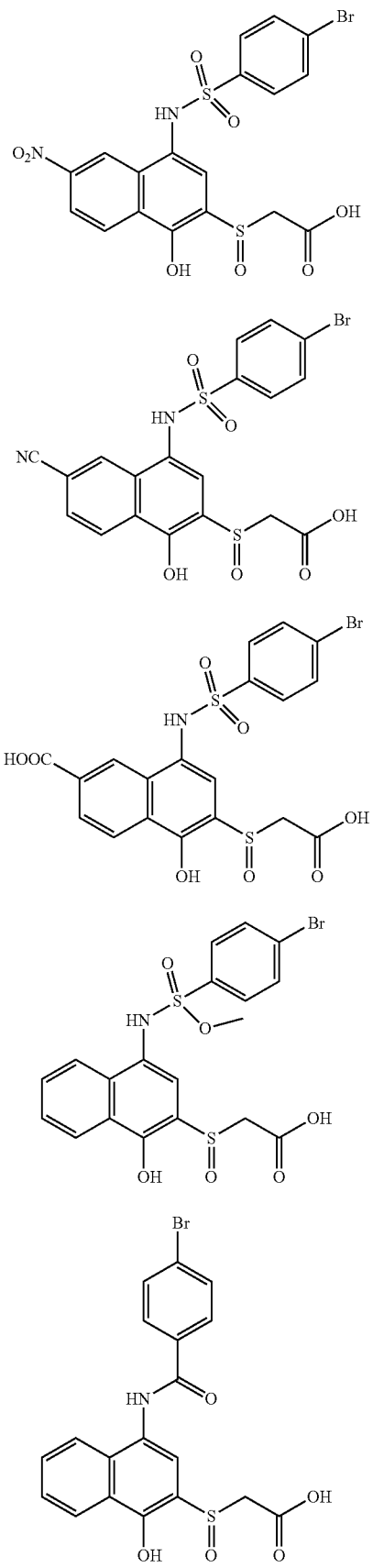

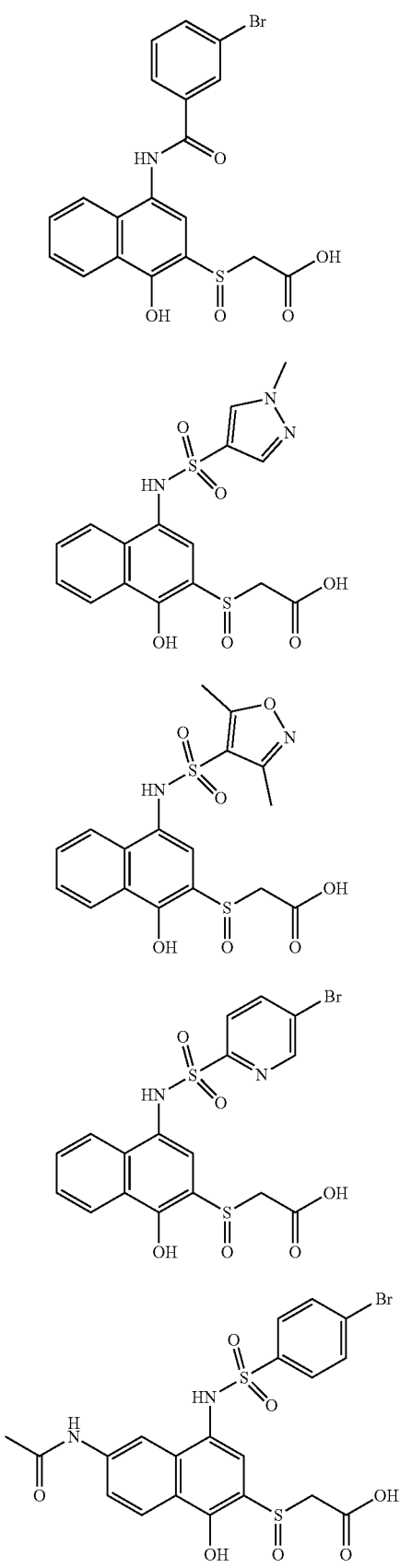
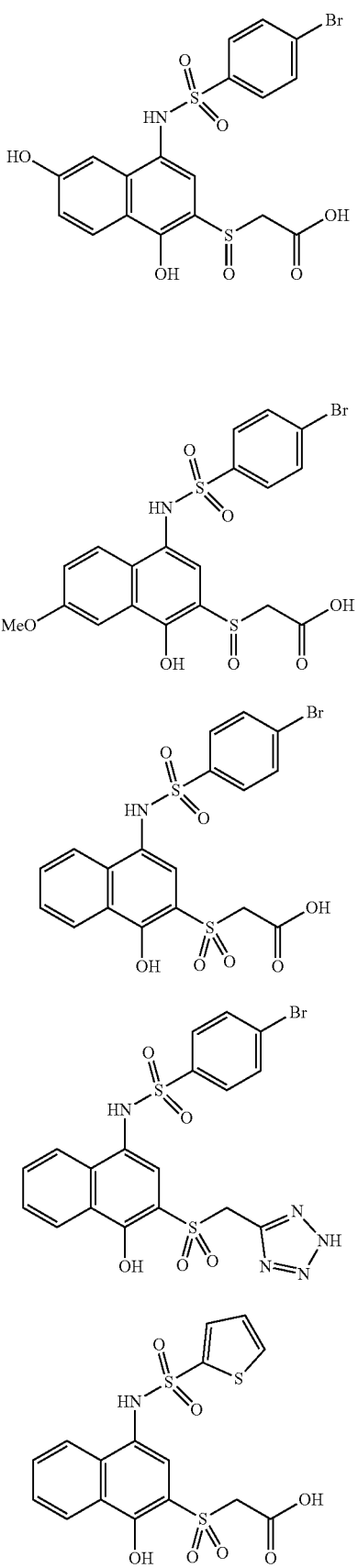

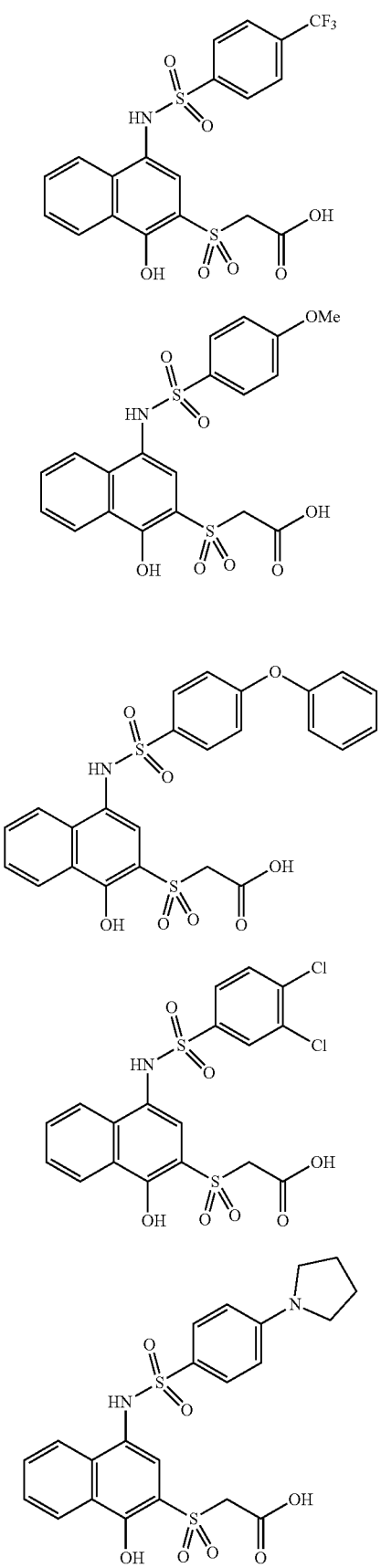
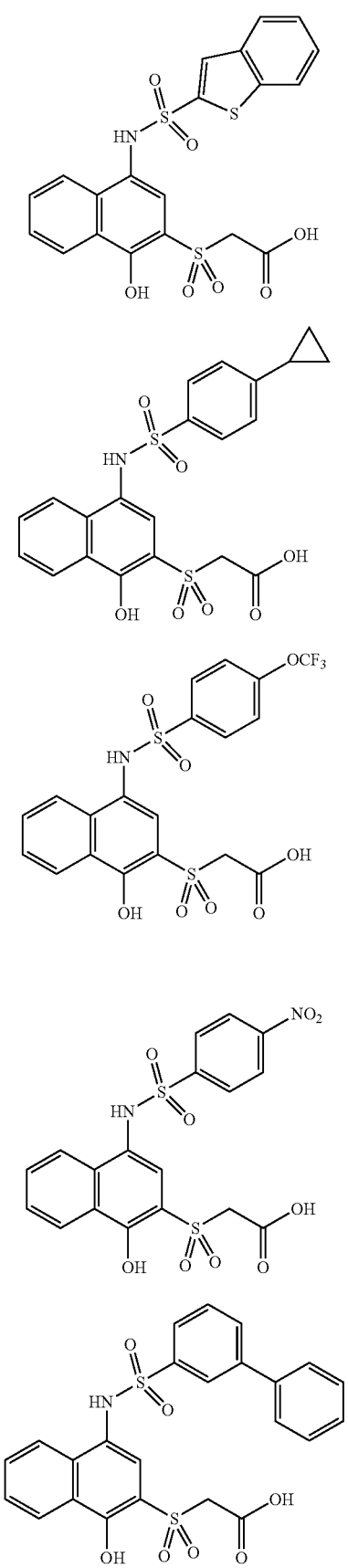

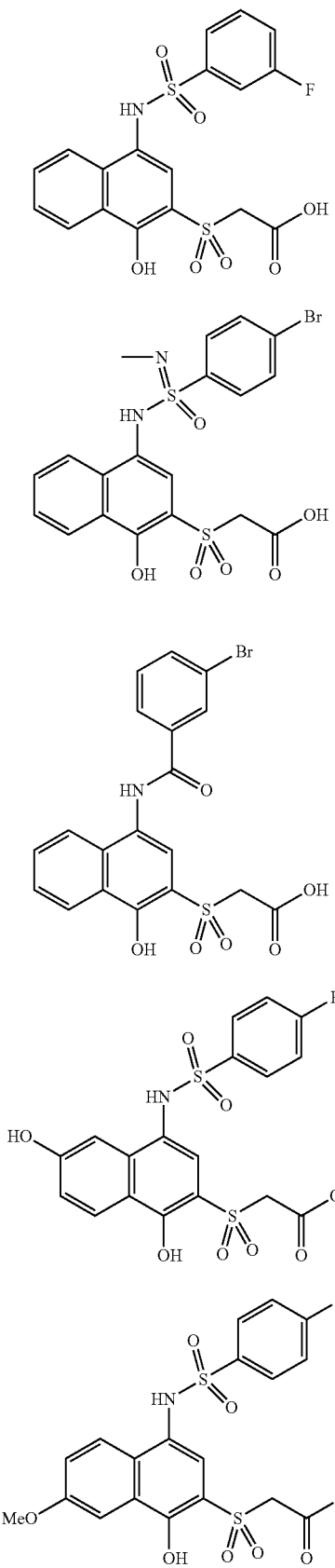

In some preferred embodiments, the $C_{1\sim6}$ alkyl is a $C_{1\sim4}$ alkyl, and the $C_{1\sim4}$ alkyl is preferably methyl, ethyl, n-propyl, isopropyl, n-butyl, isobutyl or tert-butyl, such as methyl or ethyl.

In some preferred embodiments, the three to six-membered cycloalkyl is preferably $C_{3\sim5}$ cycloalkyl, and the $C_{3\sim5}$ cycloalkyl is preferably

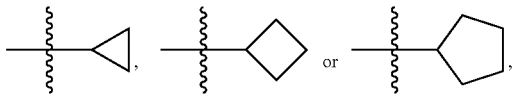

for example:

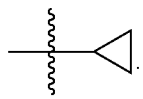 [SMILES: *C1CC1]

In some preferred embodiments, the three- to six-membered epoxyalkyl is preferably

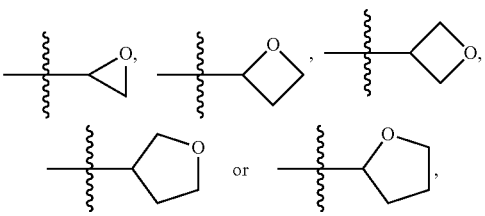

for example:

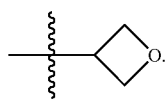 [SMILES: *C1COC1]

In some preferred embodiments, the phenyl substituted by $C_{1\sim6}$ alkyl is preferably phenyl substituted by $C_{1\sim4}$ alkyl, more preferably phenyl substituted by any one of methyl, ethyl, n-propyl, isopropyl, butyl, isobutyl and tert-butyl.

In some preferred embodiments, the $C_{1\sim6}$ alkoxy is preferably $C_{1\sim4}$ alkoxy, more preferably methoxy, ethoxy, n-propoxy, isopropoxy, or n-butoxy, tert-butoxy, sec-butoxy or isobutoxy.

In some preferred embodiments, the —N(R$^{3-2}$R$^{3-2a}$), —N(R$^{3-3a}$R$^{3-3b}$), —N(R$^{4-1a}$R$^{4-1b}$), —N(R$^{5-1}$R$^{5-1a}$) is preferably

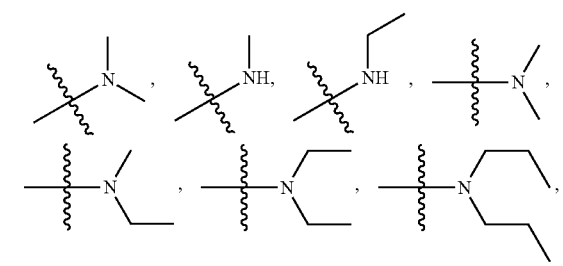

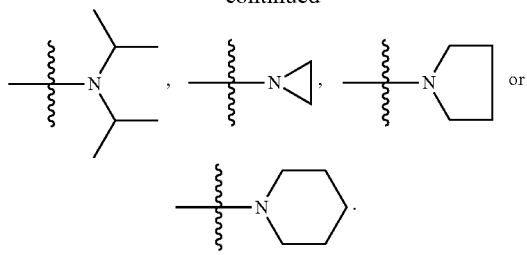

In some preferred embodiments, the 5- or 6-membered monocyclic heteroaryl is preferably

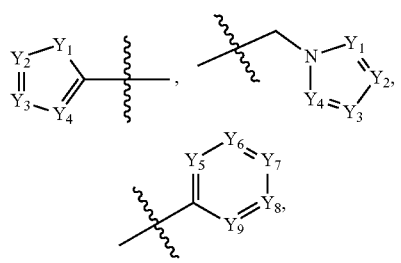

wherein $Y_1$, $Y_2$, $Y_3$, $Y_4$, $Y_5$, $Y_6$, $Y_7$, $Y_8$, $Y_9$ are each independently selected from C, N, O or S, and $Y_1$, $Y_2$, $Y_3$, and $Y_4$ are not all C, and $Y_5$, $Y_6$, $Y_7$, $Y_8$, and Y are not all C; the 5- or 6-membered monocyclic heteroaryl is more preferably pyrrolyl, furyl, thienyl, pyrazolyl, imidazolyl, oxazolyl, isoxazolyl, thiazolyl, pyridyl, pyranyl, thiopyran, pyridazinyl, pyrimidinyl, pyrazinyl, piperazinyl, triazolyl, tetrazolyl; the 5- or 6-membered monocyclic heteroaryl is more preferably

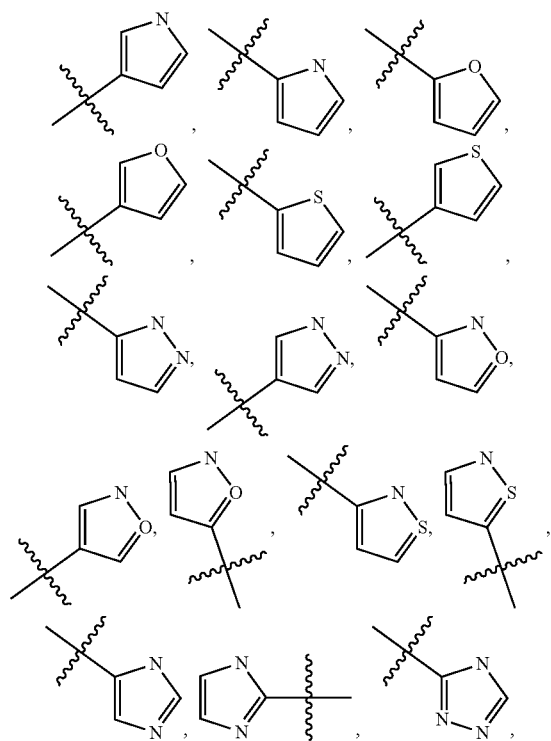

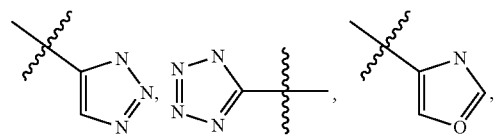

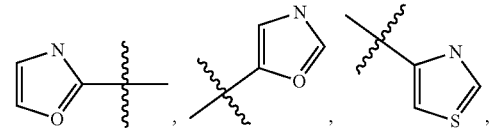

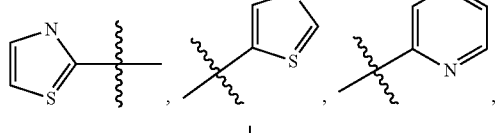

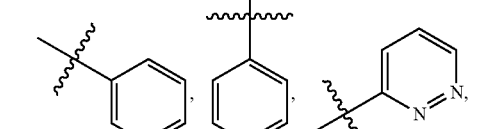

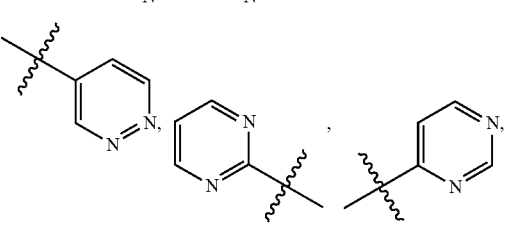

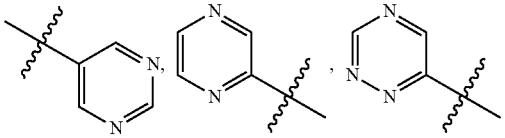

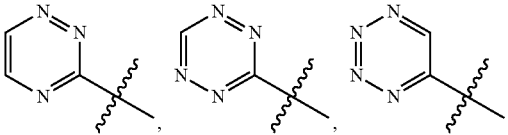

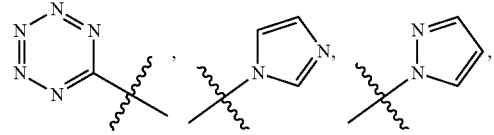

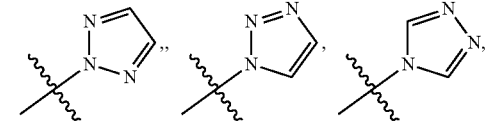

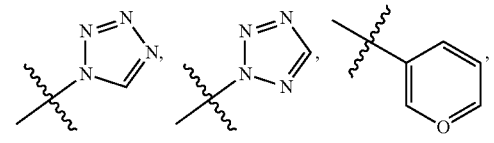

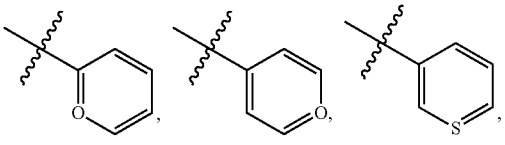

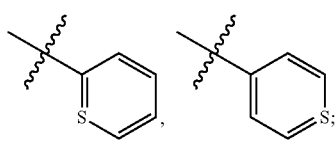

more preferably, the 5- or 6-membered monocyclic heteroaryl is 5- or 6-membered nitrogen-containing monocyclic heteroaryl, such as:

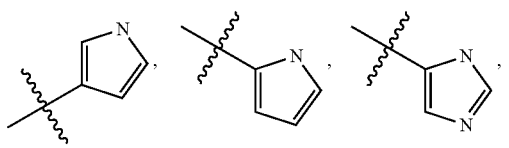

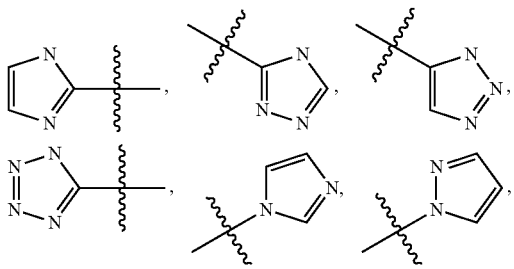

most preferably, the 5- or 6-membered monocyclic heteroaryl is 5-membered nitrogen-containing monocyclic heteroaryl, such as:

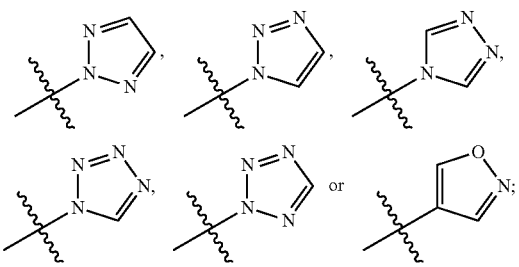

In some preferred embodiments, the 8 to 10-membered fused bicyclic heteroaryl is

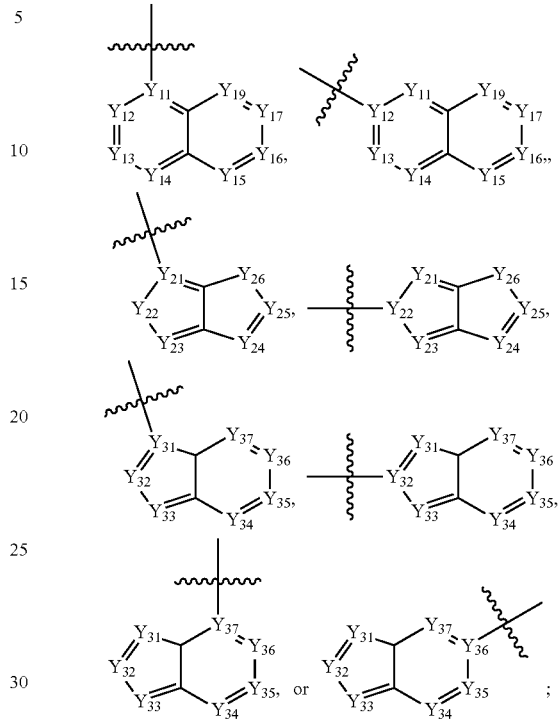

wherein, $Y_{11}$, $Y_{12}$, $Y_{13}$, $Y_{14}$, $Y_{15}$, $Y_{16}$, $Y_{17}$, $Y_{18}$ and $Y_{19}$ are each independently selected from C, N, O or S, and $Y_{11}$, $Y_{12}$, $Y_{13}$, $Y_{14}$, $Y_{15}$, $Y_{16}$, $Y_{17}$, $Y_{18}$ and $Y_{19}$ are not all C; $Y_{21}$, $Y_{22}$, $Y_{23}$, $Y_{24}$, $Y_{25}$ and $Y_{26}$ are each independently selected from C, N, O or S, and $Y_{21}$, $Y_{22}$, $Y_{23}$, $Y_{24}$, $Y_{25}$ and $Y_{26}$ are not all C; $Y_{31}$, $Y_{32}$, $Y_{33}$, $Y_{34}$, $Y_{35}$, $Y_{36}$ and $Y_{37}$ are each independently selected from C, N, O or S, and $Y_{31}$, $Y_{32}$, $Y_{33}$, $Y_{34}$, $Y_{35}$, $Y_{36}$ and $Y_{37}$ are not all C; the 8 to 10-membered fused bicyclic heteroaryl is more preferably indolyl, benzindolyl, benzothienyl, carbazolyl, quinolyl, pteridyl, purinyl; the 8 to 10-membered fused bicyclic heteroaryl is most preferably

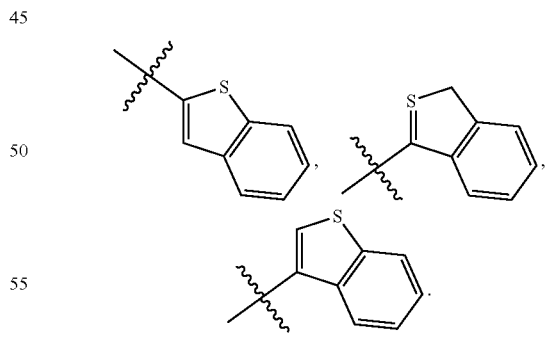

In some preferred embodiments, the halogen is preferably fluorine, chlorine, bromine or iodine.

In some preferred embodiments, the $C_{1-6}$ haloalkyl is preferably $C_{1-3}$ haloalkyl; more preferably, fluoromethyl, fluoroethyl, fluoro-n-propyl, fluoroisopropyl, chloromethyl, chloroethyl, chloro-n-propyl, chloroisopropyl, bromomethyl, bromoethyl, bromo-n-propyl, bromoisopropyl, iodomethyl, iodoethyl, iodo-n-propyl, iodoisopropyl; most preferably, trifluoromethyl.

In some preferred embodiments, the $C_{1\sim6}$ haloalkoxy is preferably $C_{1\sim3}$ haloalkoxy; more preferably, fluoromethoxy, fluoroethoxy, fluoro-n-propoxy fluoroisopropoxy, chloromethoxy, chloroethoxy, chloro-n-propoxy, chloroisopropoxy, bromomethoxy, bromoethoxy, bromo-n-propoxy, bromoisopropoxy, iodooxymethyl, iodoethoxy, iodo-n-propoxy, iodoisopropoxy; most preferrably, trifluoromethoxy.

In some preferred embodiments, the $C_{2\sim6}$ alkenyl is preferably $C_{2\sim4}$ alkenyl, more preferably —CH=CH$_2$, —CH=CH—CH$_3$, —CH$_2$—CH=CH$_2$, —CH=CH—CH$_2$—CH$_3$, —CH=CH—CH=CH$_2$.

In some preferred embodiments, the $C_{2\sim6}$ alkynyl is preferably $C_{2\sim6}$ alkynyl, more preferably —C≡CH, —CH$_2$—C≡CH, —CH$_2$—CH$_2$—C≡CH, —CH$_2$—C≡C—CH$_3$.

In a second aspect of the present invention, it provides a pharmaceutical composition, comprising the compounds and a pharmaceutically acceptable salt, stereoisomer, solvate or prodrug thereof as described in the first aspect of the present invention.

In a third aspect of the present invention, it provides a use of the compound, or a pharmaceutically acceptable salt, stereoisomer, solvate or prodrug thereof as described in the first aspect of the present invention, or the pharmaceutical composition described in the second aspect of the present invention in the preparation of mitophagy inducers (especially selective mitophagy inducers).

Compared with the prior art, the present invention has at least the following advantages:

(1) The compound and pharmaceutically acceptable salts, stereoisomers, solvates or prodrugs thereof provided in the first aspect of the present invention or the pharmaceutical composition provided in the second aspect of the present invention can induce autophagy in damaged mitochondria, and selectively induce autophagy in damaged mitochondria without affecting the normal mitochondria or only weakly affecting the normal mitochondria;

(2) The compound and its pharmaceutically acceptable salts, stereoisomers, solvates or prodrugs thereof provided in the first aspect of the present invention or the pharmaceutical composition provided in the second aspect of the present invention have superior properties of metabolic stability and pharmacokinetic properties compared to UMI-77;

(3) The compound and pharmaceutically acceptable salts, stereoisomers, solvates or prodrugs thereof provided in the first aspect of the present invention, or the pharmaceutical composition provided in the second aspect of the present invention are less toxic, better druggability compared to UMI-77;

(4) The compound and pharmaceutically acceptable salts, stereoisomers, solvates or prodrugs thereof provided in the first aspect of the present invention or the pharmaceutical composition provided in the second aspect of the present invention.

Therefore, the compounds of the present invention have the effect of inducing autophagy in damaged mitochondria or improving metabolic stability. Preferred compounds of the present invention have the effect of both selectively inducing autophagy in damaged mitochondria and improving metabolic stability:

More preferably, preferred compounds of the present invention have the effect of selectively inducing autophagy in damaged mitochondria or improving metabolic stability. Particularly preferred compounds of the present invention have the effect of both selectively inducing damaged mitophagy and improving metabolic stability:

It should be understood that within the scope of the present invention, the above-mentioned technical features of the present invention and the technical features specifically described below (such as embodiments) can be combined with each other to form new or preferred technical solutions. Due to space limitations, they will not be described one by one herein.

DESCRIPTION OF THE DRAWINGS

One or more embodiments are exemplified by the pictures in the corresponding drawings, and these exemplary illustrations do not constitute limitations to the embodiments.

DETAILED DESCRIPTION

Figure 1:
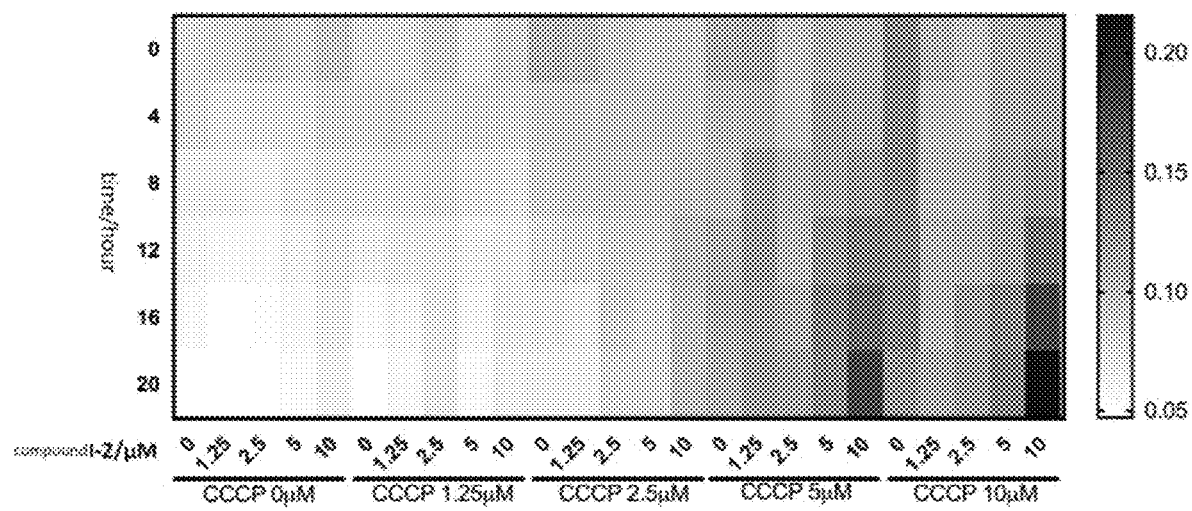
FIG. 1 is a graph showing the test results of Compound I-2's ability to induce autophagy in damaged mitochondria in Test Example 1 of the present invention.

The inventor has found through detailed experimental studies that the compounds described in the first aspect of the present invention have the effect of inducing autophagy in damaged mitochondria or improving metabolic stability:

Preferably, preferred compounds of the present invention have the effects of inducing autophagy in damaged mitochondria and improving metabolic stability.

More preferably, preferred compounds of the present invention have the effect of selectively inducing autophagy in damaged mitochondria or improving metabolic stability. Particularly preferred compounds of the present invention have the effect of selectively inducing autophagy in damaged mitochondria and improving metabolic stability:

Terms

As used herein, the term "mitophagy" refers to a process of selective degradation of mitochondria by autophagy, which is an important mechanism for the control of mitochondrial quality and quantity.

As used herein, the term "mitophagy inducer" refers to a compound that can induce mitophagy function.

As used herein, the term "alkyl" refers to a straight-chain or branched saturated aliphatic hydrocarbon group. The term "$C_{1-6}$ alkyl" refers to a straight-chain or branched alkyl having 1 to 6 carbon atoms, non-limiting examples are: methyl, ethyl, n-propyl, isopropyl, n-butyl, isobutyl, tert-butyl, sec-butyl, n-pentyl, 1,1-dimethylpropyl, 1,2-dimethylpropyl, 2,2-dimethylpropyl, 1-ethylpropyl, 2-methylbutyl, 3-methylbutyl, n-hexyl, 1-ethyl-2-methylpropyl, 1,1,2-trimethylpropyl, 1,1-dimethylbutyl, 1,2-dimethylbutyl, 2,2-dimethylbutyl, 1,3-dimethylbutyl, 2-ethylbutyl, 2-methylpentyl, 3-methylpentyl, 4-methylpentyl, 2,3-dimethylbutyl, and various branched isomers, etc. The term "$C_{1-4}$ alkyl" refers to a straight-chain or branched alkyl having 1 to 4 carbon atoms. If the $C_{1-4}$ alkyl appears at the end of the molecule, non-limiting examples are: methyl, ethyl, n-propyl, isopropyl, n-butyl, isobutyl, sec-butyl, tert-butyl, or when two parts of the molecule are connected through the alkyl, non-limiting examples are: —CH$_2$—, —CH$_2$—CH$_2$—, —CH(CH$_3$)—, —CH$_2$—CH$_2$—CH$_2$—, —CH(C$_2$H$_5$)—, —C(CH$_3$)$_2$—, each hydrogen of the $C_{1-4}$ alkyl may be substituted by a substituent further enumerated herein.

As used herein, the term "alkenyl" refers to a straight or branched hydrocarbon chain containing at least one carbon-carbon double bond. Each hydrogen in the alkenyl carbon may be substituted by a substituent further enumerated herein. The term "$C_{2-6}$ alkenyl" refers to a straight or branched hydrocarbon chain of 1 to 6 carbon atoms containing at least one carbon-carbon double bond. If it appears at the end of the molecule, non-limiting examples are: —CH=CH$_2$, —CH=CH—CH$_3$, —CH$_2$—CH=CH$_2$, —CH=CH—CH$_2$—CH$_3$, —CH=CH—CH=CH$_2$, or when two parts of the molecule are connected through the alkenyl, a non-limiting example is —CH=CH—. Each hydrogen of the $C_{2-6}$ alkenyl carbons may be substituted by a substituent further enumerated herein.

As used herein, the term "alkynyl" refers to a straight or branched hydrocarbon chain containing at least one carbon-carbon triple bond. Each hydrogen in the alkynyl carbon may be substituted by a substituent further enumerated herein. The term "$C_{2-6}$ alkynyl" refers to a straight or branched hydrocarbon chain having 1 to 6 carbon atoms containing at least one carbon-carbon triple bond. If it appears at the end of the molecule, non-limiting examples are: —C≡CH, —CH$_2$—C≡CH, —CH$_2$—CH$_2$—C≡CH, —CH$_2$—C≡C—CH$_3$, or, when two parts of the molecule are connected through the alkynyl, a non-limiting example is —C≡C—. Each hydrogen in the $C_{2-6}$ alkynyl carbon may be substituted by a substituent further enumerated herein.

As used herein, the term "alkoxy" refers to a group having the structure "—O-alkyl", wherein the alkyl is as defined above. The term "$C_{1-6}$ alkoxy" refers to an alkoxy group having 1 to 6 carbon atoms, non-limiting examples are: methoxy, ethoxy, n-propoxy, isopropoxy, n-butoxy, tert-butoxy, isobutoxy, n-pentyloxy, etc.

As used herein, the term "amido" refers to a group formed by substituting at least one hydrogen atom in the amino with an alkyl. For example: in the amido

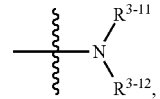

either one of $R^{3-11}$ and $R^{3-12}$ is alkyl, the other is hydrogen; or $R^{3-11}$ and $R^{3-12}$ are all alkyl; when $R^{3-11}$ and $R^{3-12}$ are all alkyl, $R^{3-11}$ and $R^{3-12}$ can be bonded to form a ring.

As used herein, the term "haloalkyl" refers to an alkyl with one or more (e.g., 1, 2, 3, 4 or 5) hydrogen atoms are substituted by halogen, wherein the alkyl is as defined above.

As used herein, "(O)" refers to

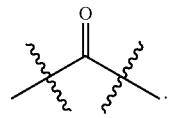

In one embodiment, —CH$_2$C(O)R$^{3-2}$ refers to

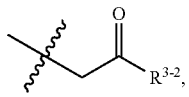

As used herein, the term "halooxyalkyl" refers to an alkoxy with one or more hydrogen atoms substituted by halogen, wherein the alkoxy is as defined above.

As used herein, the terms "aryl", "aryl ring" and "aromatic ring" are used interchangeably and refer to all-carbon monocyclic, all-carbon non-fused polycyclic (rings connected by covalent bonds, non-fused) or all-carbon fused polycyclic (that is, rings sharing pairs of adjacent carbon atoms) groups, at least one ring in the group is aromatic, that is, it has a ring-forming conjugated π electron system.

As used herein, the term "heteroaryl" refers to an aryl group in which at least one of the ring carbon atoms making up the aryl is replaced by a heteroatom that is a non-carbon atom, such as S, N, or O.

As used herein, the term "monocyclic heteroaryl" refers to a heteroaryl group having only one aromatic ring, wherein heteroaryl is as defined above. The term "5- or 6-membered monocyclic heteroaryl" refers to a monocyclic heteroaryl having 5 or 6 ring atoms, of which 1, 2 or 3 ring atoms are heteroatoms selected from nitrogen, oxygen or S(=O)m' (wherein m' is an integer 0 to 2), non-limiting examples: thiophene, furan, thiazole, isothiazole, imidazole, oxazole, pyrrole, pyrazole, triazole (e.g. 1, 2, 3-triazole, 1,2,4-triazole, 1,2,5-triazole, 1,3,4-triazole, etc.), tetrazole, isoxazole, oxadiazole, 1,2,3-oxadiazole, 1,2,4-oxadiazole, 1,2,5-oxadiazole, 1,3,4 oxadiazole, thiadiazole, pyridine, pyridazine, pyrimidine, pyrazine etc.

As used herein, the term "fused ring heteroaryl" refers to at least two aromatic rings in which two ring atoms are adjacent to each other, wherein heteroaryl is as defined above. The term "fused bicyclic heteroaryl" refers to a fused ring heteroaryl having two aromatic rings, wherein the fused ring heteroaryl is as defined above. The term "8 to 10-membered fused bicyclic heteroaryl" refers to those having 8 to 10 ring atoms, of which 1, 2, 3, 4 or 5 ring atoms are heteroatoms selected from nitrogen, oxygen, or S(=O)m' (wherein m' is an integer 0 to 2), non-limiting examples include: benzo[d] isoxazole, 1H-indole, isoindole, 1H-benzo[d]imidazole, benzo[d]isothiazole, 1H-benzo[d][1,2,3]triazole, benzo[d] oxazole, benzo[d]thiazole, indazole, benzofuran, benzo[b] thiophene, quinoline, isoquinoline, quinazoline, quinoxaline, cinnoline, pyrido[3,2-d]pyrimidine, pyrido[2,3-d]pyrimidine, pyrido[3,4-d]pyrimidine, pyrido[4,3-d]pyrimidine, 1,8-naphthyridine, 1,7-naphthyridine, 1,6-naphthyridine, 1,5-naphthyridine, pyrazolo[1,5-a]pyrimidine, imidazo[1,2-b]pyridazine, etc.

As used herein, the term "effective dose" or "therapeutically effective dose" refers to a chemical entity (e.g., a compound that exhibits activity as a modulator of NLRP1/3, or a pharmaceutically acceptable salt and/or hydrate thereof and/or cocrystal) in a sufficient amount that, when administered, the dose will alleviate to a certain extent one or more of the symptoms of the disease or condition being treated. Results include alleviation and/or remission of signs, symptoms or causes of disease or any other desired change in a biological system. The appropriate "effective" dose in any individual situation is determined using any appropriate technique, such as dose escalation studies.

As used herein, the term "excipient" or "pharmaceutically acceptable excipient" means a pharmaceutically acceptable material, composition or vehicle such as a liquid or solid filler, diluent, carrier, solvent, or packaging materials. In one embodiment, each component is compatible with the other ingredients of the pharmaceutical formulation and is suitable for contacting with human and animal tissues or organs without undue toxicity, irritation, allergic response, immunogenicity or other problems or complications and is "pharmaceutically acceptable" in the sense of being proportionate to a reasonable benefit/risk ratio.

As used herein, the term "pharmaceutically acceptable salts" may refer to pharmaceutically acceptable addition salts prepared from pharmaceutically acceptable non-toxic acids, including inorganic acids and organic acids. In some cases, pharmaceutically acceptable salts are obtained by reacting a compound described herein with an acid. The term "pharmaceutically acceptable salt" may also refer to the formation of a salt by reacting a compound having an acidic group with a base or pharmaceutically acceptable addition salts prepared by other methods as previously determined. The pharmacologically acceptable salt is not particularly limited as long as it can be used in medicines. Examples of salts formed by the compounds described herein with bases include the following: salts with inorganic bases such as sodium, potassium, magnesium, calcium and aluminium; salts with organic bases such as methylamine, ethylamine, and ethanolamine; or formed by reaction with dicyclohexylamine, N-methyl-D-glucosamine or tris(hydroxymethyl)methylamine; salts with basic amino acids such as lysine and ornithine; and ammonium salts. The salt may be an acid addition salt, this is exemplified by the addition of salts to the following acids: inorganic acids, such as hydrochloric acid, hydrobromic acid, hydroiodic acid, sulfuric acid, nitric acid and phosphoric acid; organic acids, such as formic acid, acetic acid, propionic acid, oxalic acid, malonic acid, succinic acid, fumaric acid, maleic acid, lactic acid, malic acid, tartaric acid, citric acid, methanesulfonic acid and ethanesulfonic acid; acidic amino acids such as aspartic acid and glutamic acid.

As used herein, the term "excipient" or "pharmaceutically acceptable excipient" means a pharmaceutically acceptable material, composition, or vehicle, such as a liquid or solid filler, diluent, carrier, solvent, or encapsulating material. In one embodiment, each component is compatible with the other ingredients of the pharmaceutical formulation and is suitable for contacting with human and animal tissues or organs without undue toxicity, irritation, allergic response, immunogenicity or other problems or complications, and is "pharmaceutically acceptable" in the sense of being proportionate to a reasonable benefit/risk ratio.

As used herein, the term "pharmaceutical composition" refers to a mixture of a compound described herein and "excipients" such as carriers, stabilizers, diluents, dispersing agents, suspending agents and/or thickening agents. Pharmaceutical compositions facilitate the administration of compounds to an organism. A variety of techniques for administering compounds exist in the art, including, but not limited to, rectal, oral, intravenous, aerosol, parenteral, ocular, pulmonary, and topical administration.

As used herein, the term "subject" refers to an animal, including, but not limited to, a primate (e.g., a human), a monkey, a cow, a pig, a sheep, a goat, a horse, a dog, a cat, a rabbit, a rat, or a mouse. The terms "subject" and "patient" are used interchangeably herein, for example with respect to mammalian subjects (e.g., humans).

As used herein, the terms "treat, treating and treatment" in the context of treating a disease or disorder are meant to include alleviation or elimination of the disorder, disease or condition, wherein the term "disorder" as used herein shall always be understood to mean "a disorder, disease or condition" or one or more of the symptoms associated with a disorder; or slowing a disorder or condition or slowing the progression, spread or worsening of one or more of its symptoms.

Unless otherwise specified, "selective" as used herein refers to the property of significantly inducing damaged mitophagy without affecting normal mitochondria or only weakly affecting normal mitochondria. "Metabolic stability" as used herein includes, but is not limited to, liver microsome stability and plasma stability:

Unless otherwise specified, as used herein,

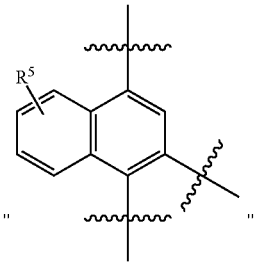

means that the naphthalene ring (including the two benzene rings on the left and the right) is substituted by 0, 1, 2, 3, 4 or 5 $R^5$, and when the naphthalene ring is substituted by more than 1 of $R^5$, $R^5$ may be the same or different each time it appears.

In order to make the purpose, technical solutions and advantages of the embodiments of the present invention clearer, the present invention will be further described below in conjunction with specific embodiments. It should be understood that these examples are only used to illustrate the invention and are not intended to limit the scope of the invention. Experimental methods without specifying specific conditions in the following examples usually follow conventional conditions or conditions recommended by the manufacturer. Unless otherwise stated, percentages and parts are by weight. The experimental materials and reagents used in the following examples can be obtained from commercial sources unless otherwise specified.

Unless otherwise specified, technical and scientific terms used herein have the same meanings as commonly understood by those of ordinary skill in the technical field to which this application belongs. It should be noted that the terms used herein are only for describing specific embodiments and are not intended to limit the exemplary embodiments of the present invention.

Example 1. Synthesis and Characterization of Compound I-1

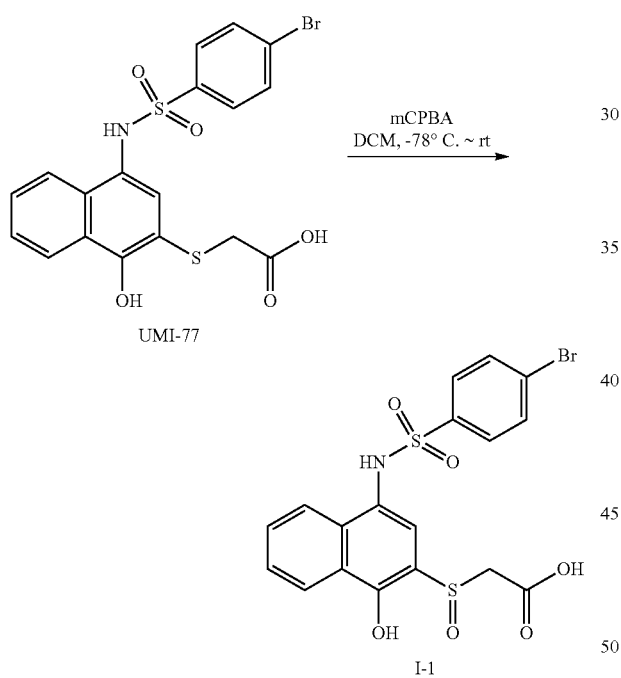

UMI-77 (15 mg, 0.032 mmol) was suspended in DCM (0.5 mL) and stirred in a dry ice-ethanol bath, 85% mCPBA (6.5 mg, 0.032 mmol) was added, and then slowly returned to room temperature. The formed product I-1 was detected by LC-MS. The organic solvent was evaporated under reduced pressure, and the obtained crude product was purified by preparative HPLC (MeCN/H$_2$O/TFA) to obtain product I-1 (6 mg).

The purified product I-1 was taken for structural characterization, LC-MS (ESI) m/z: 482, 484 [MH]$^-$. $^1$H-NMR (400 MHZ, DMSO-d$_6$) δ (ppm): 13.1 (s, 1H), 10.98 (s, 1H), 10.17 (s, 1H), 8.25 (d, J=7.4 Hz, 1H), 8.00 (d, J=8.6 Hz, 1H), 7.71 (d, J=8.3 Hz, 2H), 7.64-7.50 (m, 4H), 7.21 (s, 1H), 4.00 (d, J=14.2 Hz, 1H), 3.45 (d, J=14.2 Hz, 1H).

Example 2. Synthesis and Characterization of Compound I-2

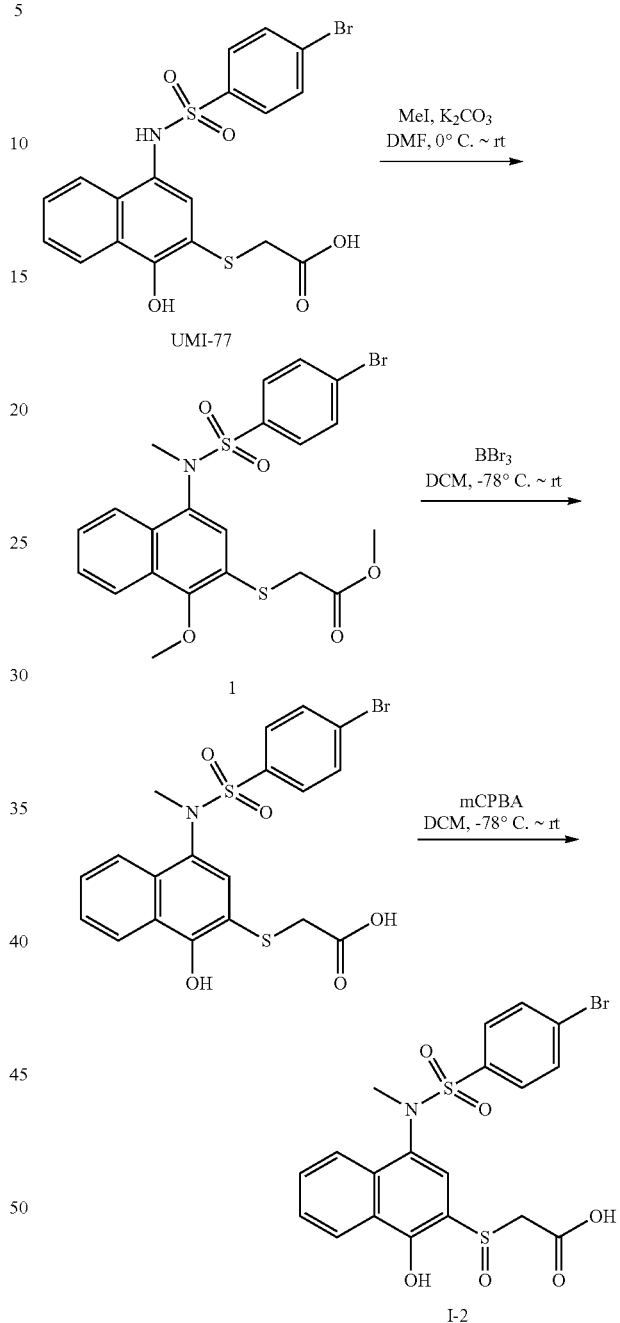

UMI-77 (45 mg, 0.096 mmol) was dissolved in DMF (0.5 mL) under the protection of nitrogen atmosphere and stirred in an ice-water bath. K$_2$CO$_3$ (39 mg, 0.28 mmol) and MeI (30 μL, 0.48 mmol) were added in sequence, kept stirring in the ice-water bath for 10 min, then returned to room temperature and continued stirring overnight. A formed trimethylated product 1 was detected by LC-MS. The reaction system was diluted with DCM and subjected to silica gel column chromatography (30% v/v ethyl acetate/petroleum ether system) to obtain an intermediate 1 (42 mg).

The intermediate 1 (42 mg, 0.081 mmol) was dissolved in dry DCM (0.5 mL) and stirred in a dry ice-ethanol bath. 1

M BBr₃ was added dropwise to DCM solution (0.24 mL, 0.24 mmol), then slowly returned to room temperature and continued stirring for 2 hours. A formed demethylated product was detected by LC-MS. The demethylated product (15 mg, 0.031 mmol) was suspended in DCM (0.5 mL) and stirred in a dry ice-ethanol bath. 85% mCPBA (6.3 mg, 0.031 mmol) was added, and then slowly returned to room temperature. The product I-2 was detected by LC-MS. The organic solvent was evaporated under reduced pressure, and the obtained crude product was purified by preparative HPLC (MeCN/H₂O/TFA) to obtain product I-2 (5 mg).

The purified product I-2 was taken for structural characterization, LC-MS (ESI) m/z: 496, 498 [MH]⁻. ¹H-NMR (400 MHZ, DMSO-d₆) δ (ppm): 13.2 (s, 1H), 11.23 (s, 1H), 8.34 (d, J=8.5 Hz, 1H), 8.20 (d, J=8.4 Hz, 0.6H), 8.13 (d, J=8.4 Hz, 0.4H), 7.91-7.81 (m, 2H), 7.80-7.57 (m, 4H), 7.09 (s, 0.4H), 6.96 (s, 0.6H), 4.03 (dd, J=24.7, 14.2 Hz, 1H), 3.60 (dd, J=25.4, 14.3 Hz, 1H), 3.25 (s, 1.2H), 3.21 (s, 1.8H).

Example 3. Synthesis and Characterization of Compound I-3

Intermediate 2 (0.8 mmol) and 2,2'-bipyridyl (0.8 mmol) were dissolved in dry DCE (5 mL), and cyclopropylboronic acid (1.6 mmol), copper acetate (0.8 mmol) and sodium carbonate (1.6 mmol) were added sequentially, heated to 80 degrees and stirred for 24 hours. A formed product 3 was detected by LC-MS. Purified by silica gel column chromatography, intermediate 3 (82 mg) was obtained. Intermediate 3 (0.26 mmol) was dissolved in DCM (0.2 mL) and pyridine (0.2 mL) and stirred in an ice-water bath. p-bromobenzenesulfonyl chloride (0.3 mmol) was added, and then slowly returned to room temperature. A formed intermediate 4 was detected by LC-MS. Purified by silica gel column chromatography, intermediate 4 (120 mg) was obtained.

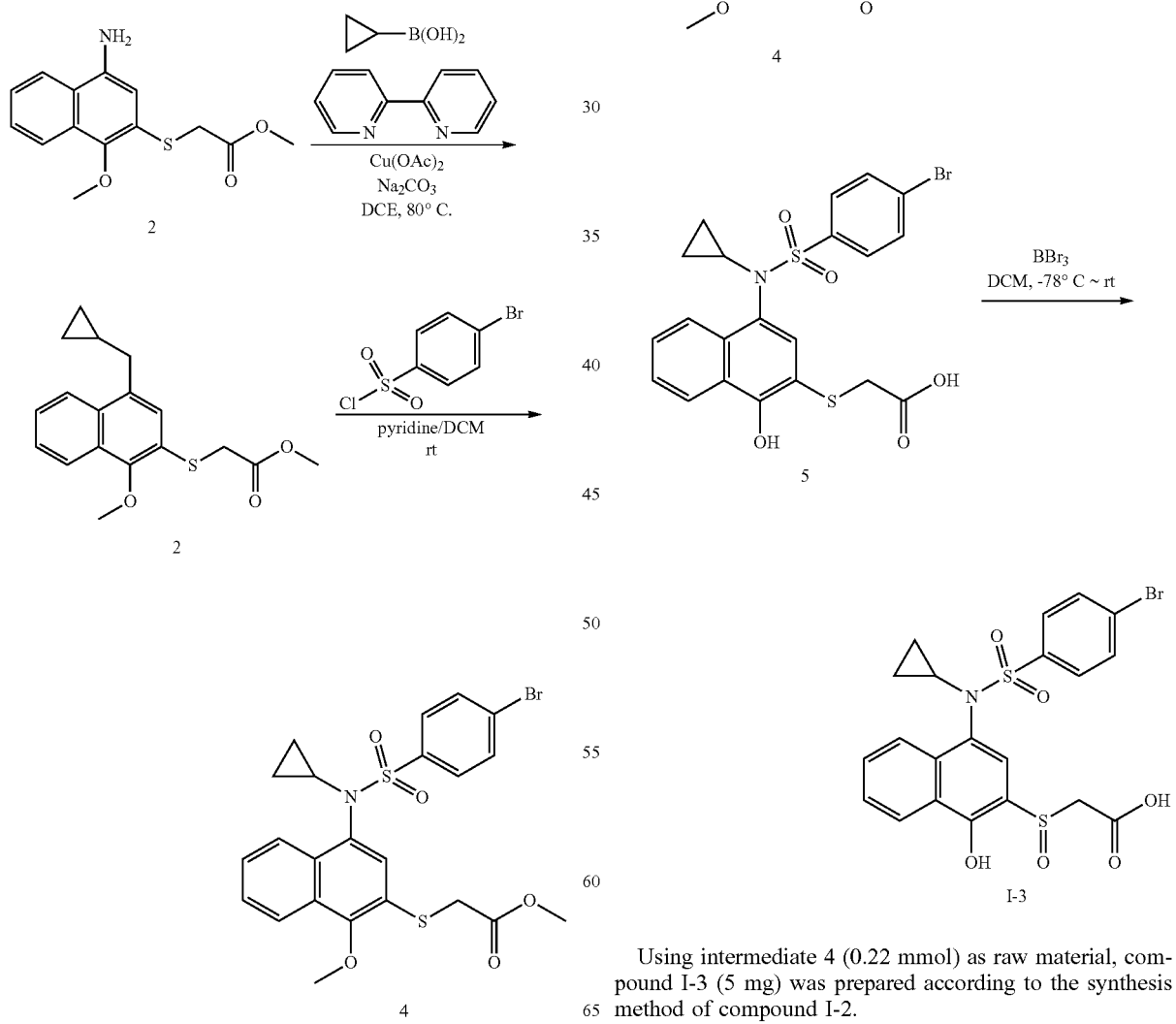

Using intermediate 4 (0.22 mmol) as raw material, compound I-3 (5 mg) was prepared according to the synthesis method of compound I-2.

The purified product I-3 was taken for structural characterization, LC-MS (ESI) m/z: 522, 524 [MH]⁻.

Example 4. Synthesis and Characterization of Compound I-4

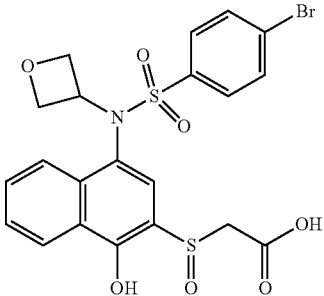

Using intermediates 2 and

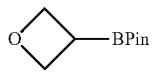

as raw materials, compound I-4 can be prepared according to the synthesis method of compound I-3 by replacing

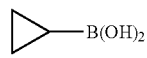

with

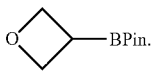

The purified product I-4 was taken for structural characterization, LC-MS (ESI) m/z: 538, 540 [MH]⁻.

Example 5. Synthesis and Characterization of Compound I-5

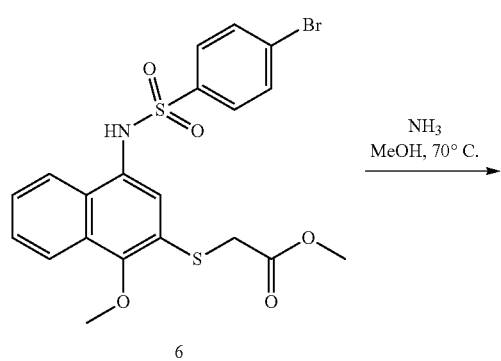

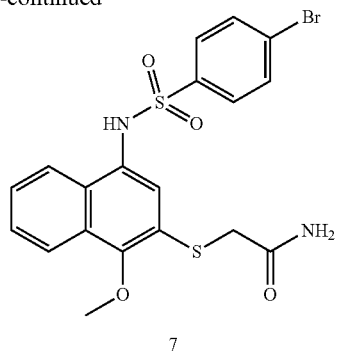

Intermediate 6 (50 mg, 0.1 mmol) was dissolved in 7M ammonia methanol (0.5 mL) and heated to 70° C. and stirred for 24 hours. A formed intermediate 7 was detected by LC-MS. The organic solvent was evaporated under reduced pressure, and the crude product obtained was directly used in the next reaction.

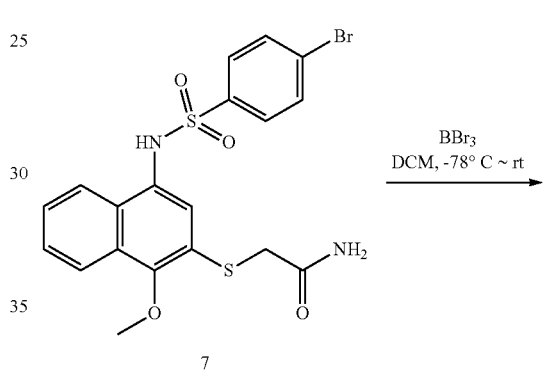

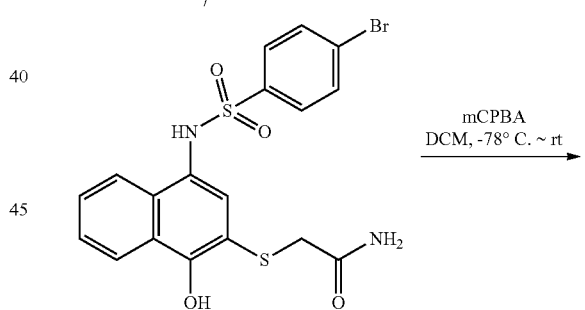

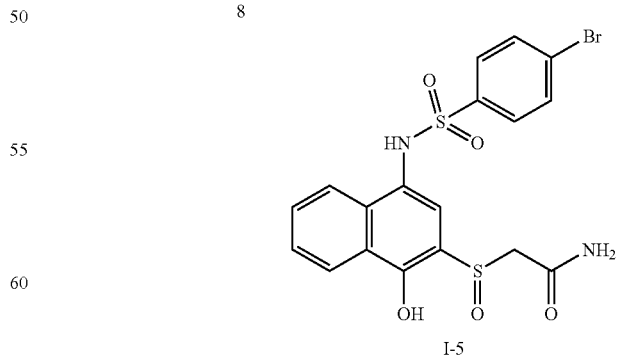

Using intermediate 7 (0.1 mmol) as raw material, compound I-5 (3 mg) was prepared according to the synthesis method of compound I-2.

The purified product I-5 was taken for structural characterization, LC-MS (ESI) m/z: 481, 483 [MH]⁻.

Example 6. Synthesis and Characterization of Compound I-6

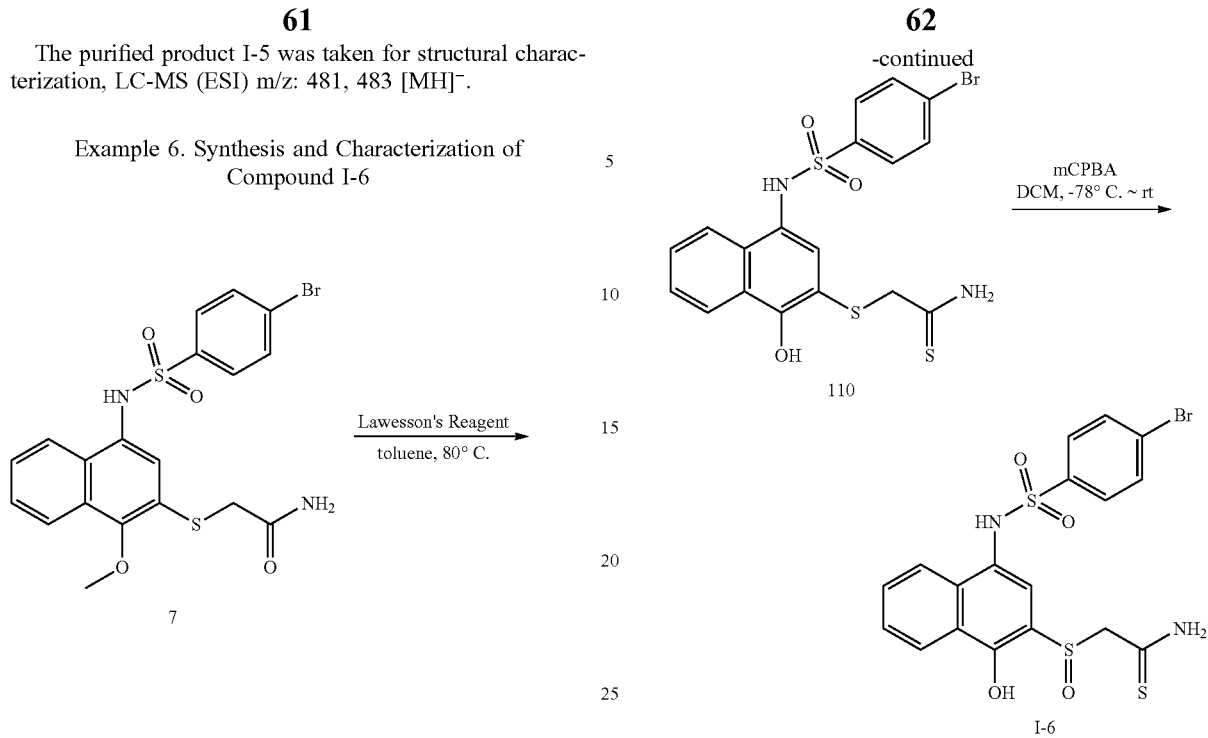

Intermediate 7 (31 mg, 0.064 mmol) was dissolved in dry methylbenzene (0.4 mL), Lawesson reagent (0.04 mmol) was added, and the mixture was heated to 80 degrees and stirred for 24 hours. A formed intermediate 9 was detected by LC-MS. Purified by Silica gel column chromatography, intermediate 9 (22 mg) was obtained.

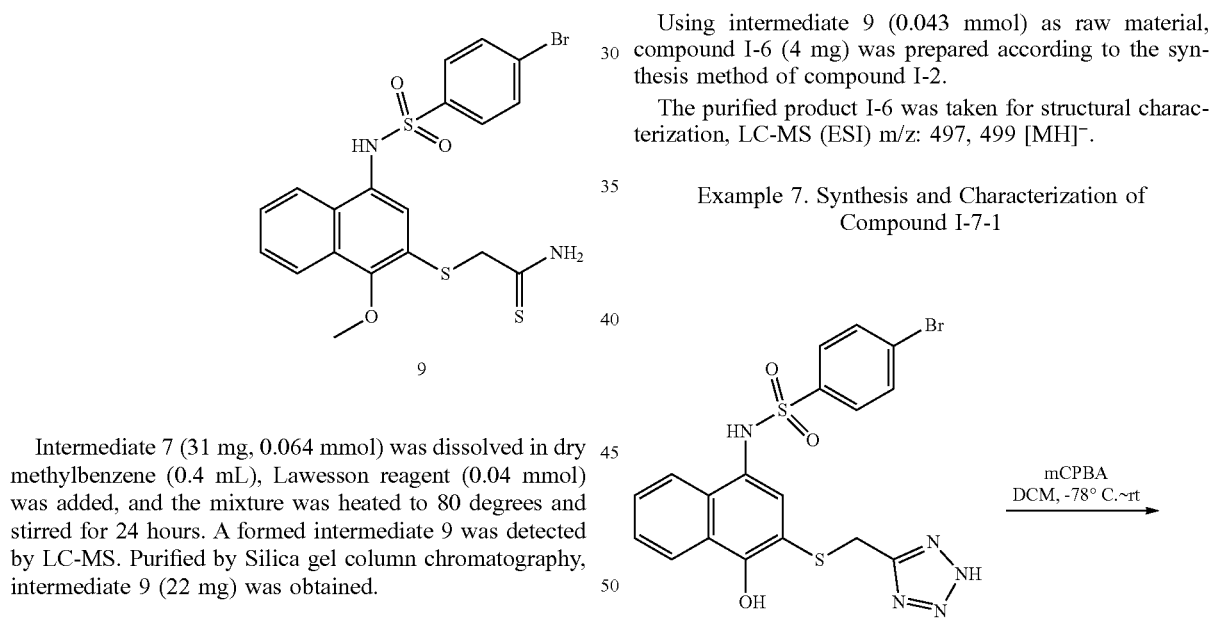

Using intermediate 9 (0.043 mmol) as raw material, compound I-6 (4 mg) was prepared according to the synthesis method of compound I-2.

The purified product I-6 was taken for structural characterization, LC-MS (ESI) m/z: 497, 499 [MH]⁻.

Example 7. Synthesis and Characterization of Compound I-7-1

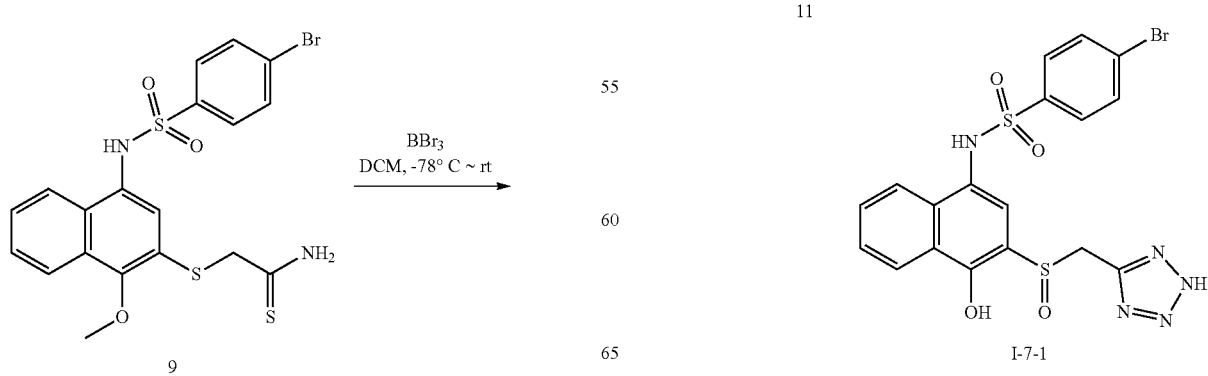

Using the known compound 11 (J. Med. Chem. 2014, 57, 4111-4133) (0.04 mmol) as raw material, compound I-7-1 (7 mg) was prepared according to the synthesis method of compound I-1.

The purified product I-7-1 was taken for structural characterization, $^1$H-NMR (400 MHZ, Methanol-d4) δ 8.17 (d, J=8.4 Hz, 1H), 7.80 (d, J=8.4 Hz, 1H), 7.62-7.56 (m, 2H), 7.56-7.45 (m, 4H), 7.10 (s, 1H), 4.70 (d, J=2.8 Hz, 2H). LC-MS (ESI) m/z: 506, 508 [MH]$^-$.

Example 8. Synthesis and Characterization of Compound I-8

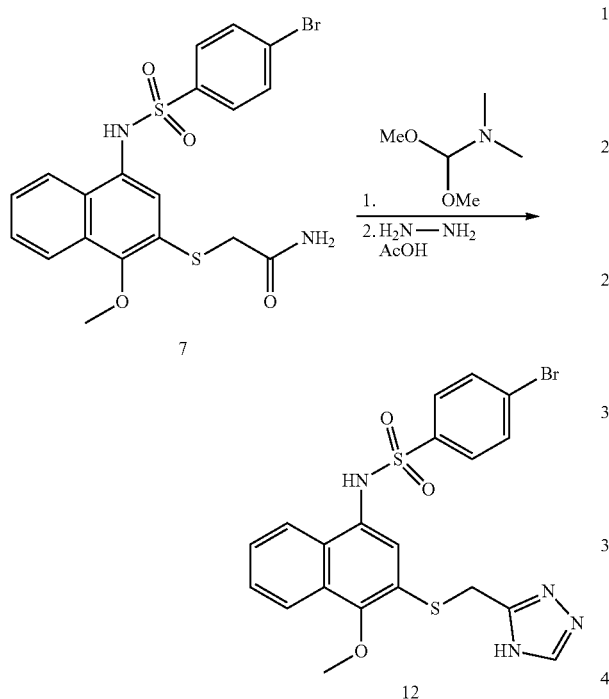

Intermediate 7 (48 mg, 0.1 mmol) was dissolved in DMF-DMA (1.0 mL) and heated and stirred at 110 degrees for 15 hours. After DMF-DMA was evaporated under reduced pressure, the residue was dissolved in acetic acid (1.0 mL), and hydrazine hydrate (0.2 mmol) was added, and heated to 90 degrees and stirred for 2 hours. A formed intermediate 12 was detected by LC-MS. Purified by Silica gel column chromatography, intermediate 12 (21 mg) was obtained.

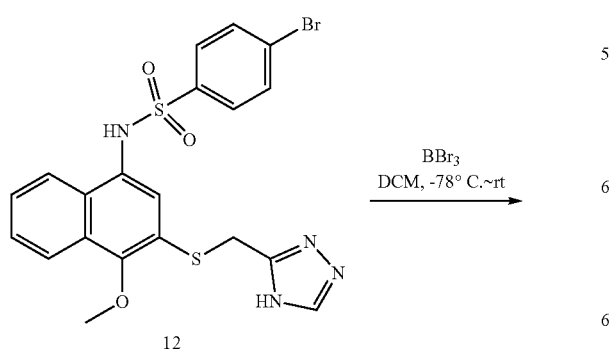

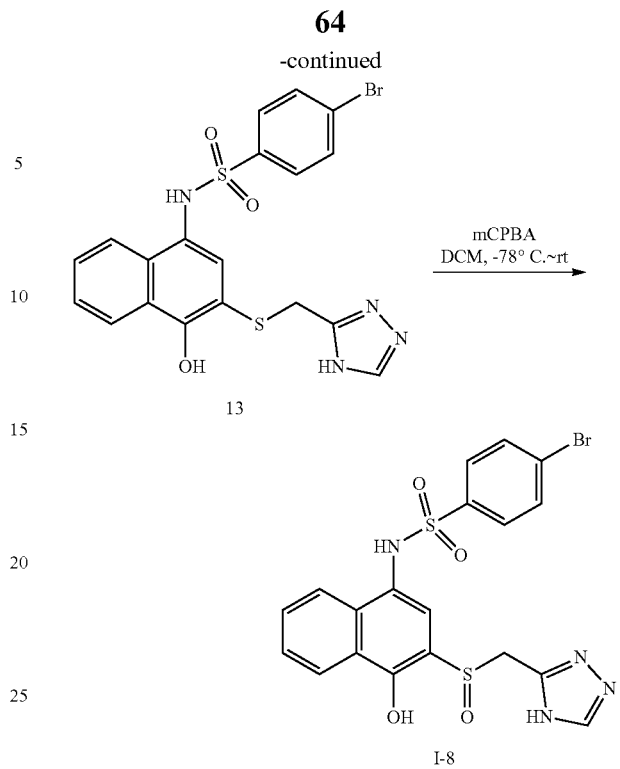

Using intermediate 12 (0.04 mmol) as raw material, compound I-8 (4 mg) was prepared according to the synthesis method of compound I-2.

The purified product I-8 was taken for structural characterization, LC-MS (ESI) m/z: 507, 509 [M+H]$^+$.

Example 9. Synthesis and Characterization of Compounds I-9-1 and I-9-2

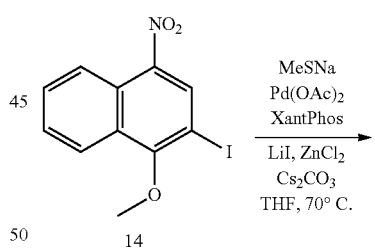

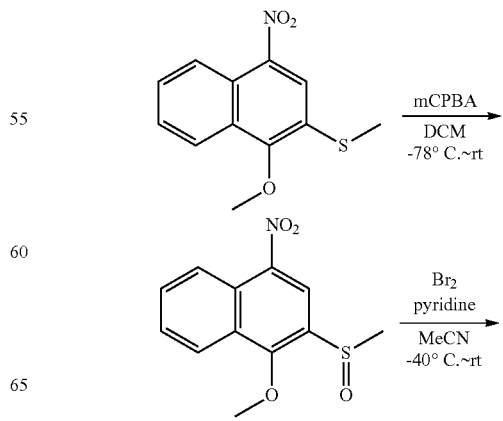

-continued

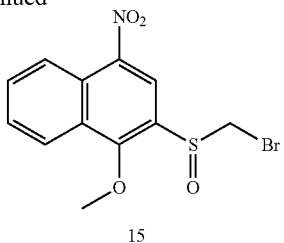

15

Intermediate 15 was preparedly using known compound 14 (5.0 mmol) as raw material. Suspend sodium methy mercaptide (1.2 eq), cesium carbonate (1.5 eq), lithium iodide (0.5 eq), 14 (1.0 eq) in anhydrous THF under nitrogen protection, added 1.0 M of Zinc Chloride THE solution (1.0 eq) with a syringe, stirred at room temperature. At the same time, palladium acetate (0.1 eq) and XantPhos (0.1 eq) are mixed in anhydrous THF, and this solution was transferred to the above suspension with a syringe. Subsequently, heating in an oil bath at 70 degrees Celsius overnight. LC-MS shows that 14 is basically consumed and product is produced. The reaction system was diluted with ethyl acetate and filtered through a layer of diatomaceous earth. The filtrate was spin-dried and subjected to silica gel column chromatography to obtain the methylthio-substituted product (3.4 mmol). This product was dissolved in anhydrous DCM and cooled in a dry ice-ethanol bath. mCPBA (1.1 eq) was added at one time and then slowly returned to room temperature. LC-MS shows that the reaction is completed. The solvent was removed by rotary evaporation, and the remaining solid was pulped with methyl tert-butyl ether to obtain a sulfoxide product (3.3 mmol). The sulfoxide product was dissolved in acetonitrile, pyridine (10 eq) was added, and stirred in a −40° C. cold bath and dropwise added liquid bromine (2.0 eq), and then slowly returned to room temperature. LC-MS shows the brominated products are formed. The reaction was quenched with saturated sodium hydrogen sulfite aqueous solution, the aqueous phase was extracted with DCM, the organic phase was spin-dried and subjected to silica gel column chromatography to prepare intermediate 15 (1.4 mmol).

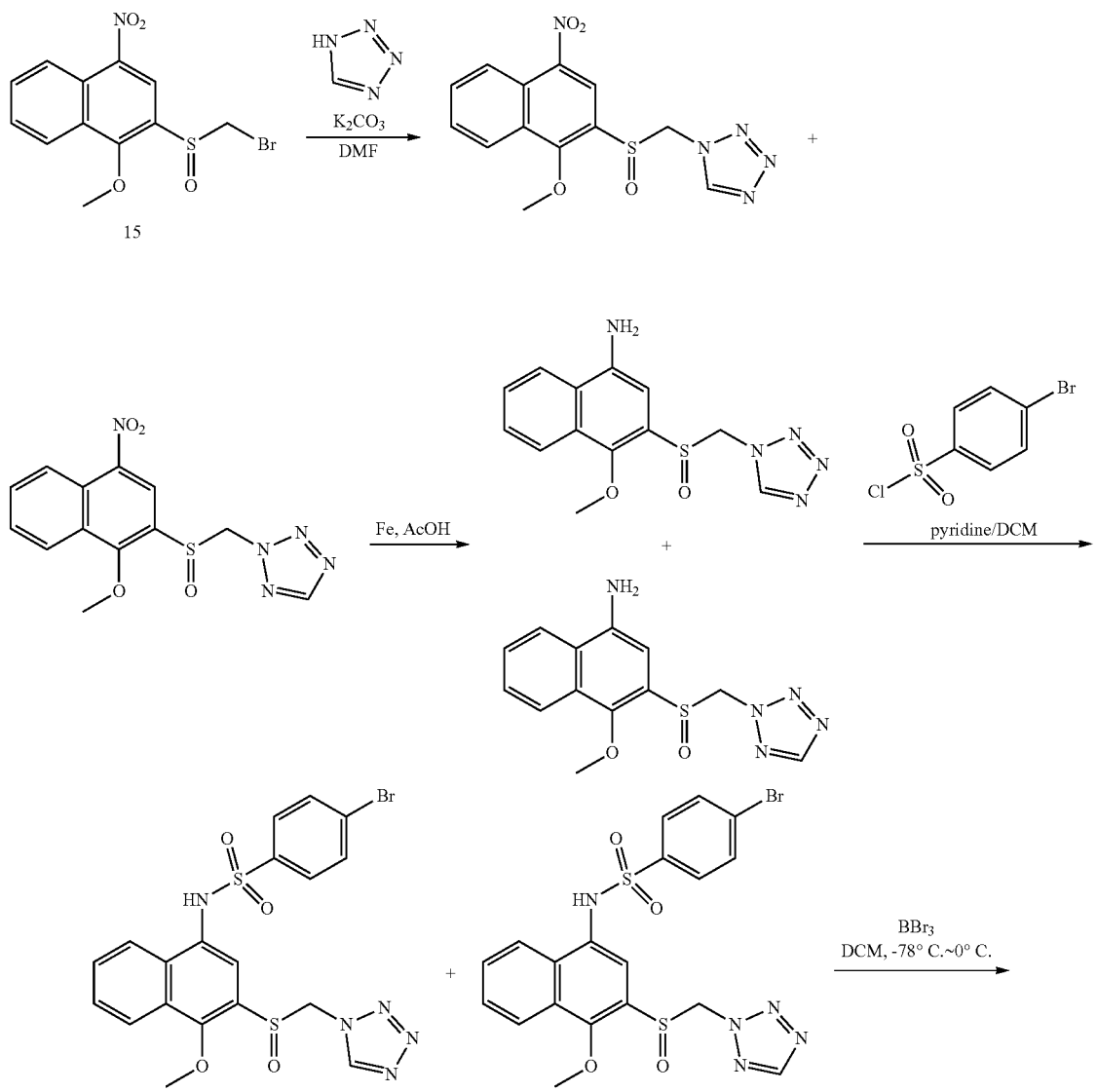

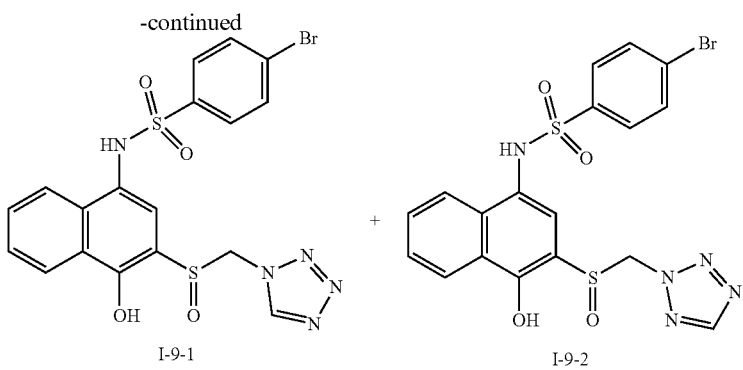

Using intermediate 15 (1.4 mmol) as raw material, tetrazole (1.2 eq) as nucleophile and potassium carbonate (1.5 eq) as base, stirring the reaction in DMF solvent at room temperature until 15 is completely consumed. Two isomers obtained cannot be separated by silica gel column chromatography. The mixture of the two (1.1 eq) can be prepared according to the synthetic route of UMI-77 (J. Med. Chem. 2014, 57, 4111-4133) to obtain compounds I-9-1 (5 mg) and I-9-2 (1 mg).

The purified product I-9-1 was taken for structural characterization, LC-MS (ESI) m/z: 508, 510 [M+H]$^+$.

The purified product I-9-2 was taken for structural characterization, LC-MS (ESI) m/z: 508, 510 [M+H]$^+$.

Example 10. Synthesis and Characterization of Compound I-10

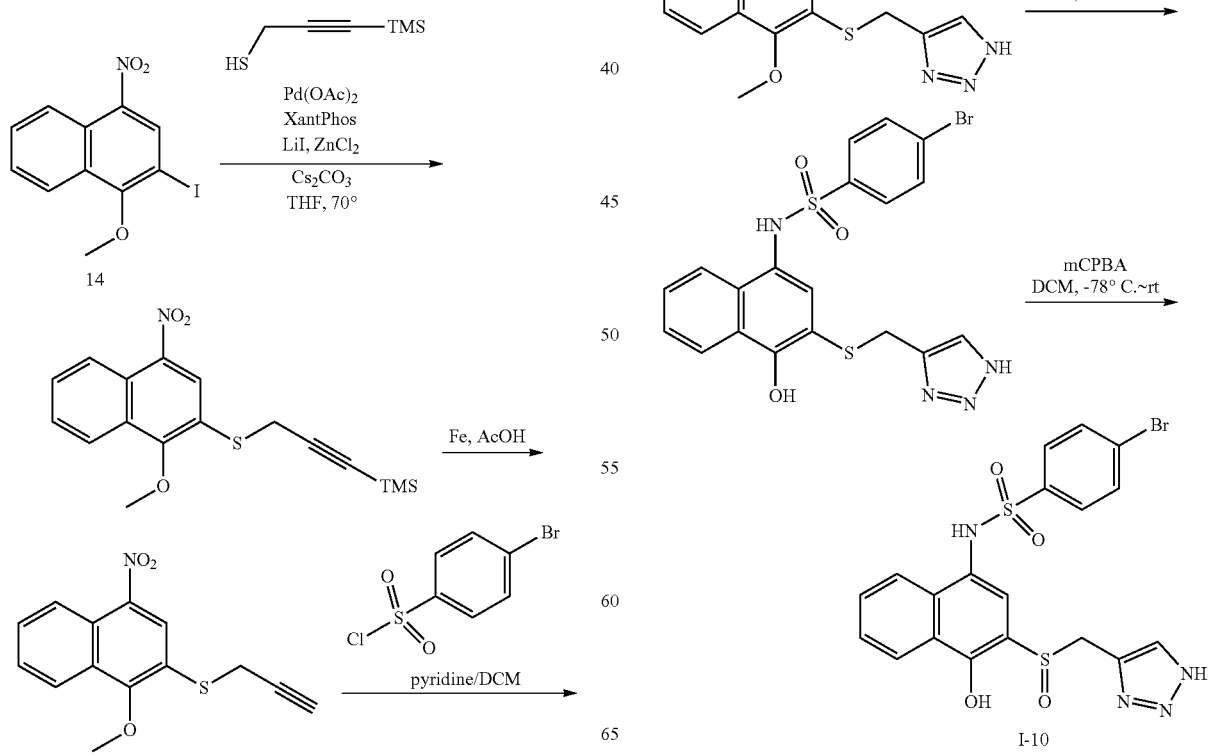

Known compound 14 (7.0 mmol), TMS-protected propargyl mercaptan (1.2 eq), cesium carbonate (2.5 eq), lithium iodide (0.5 eq) were suspended in anhydrous THF under nitrogen protection, 1.0 M zinc chloride THE solution (1.0 eq) was added via syringe and stirred at room temperature. At the same time, palladium acetate (0.1 eq) and XantPhos (0.1 eq) were mixed and dissolved in anhydrous THF, and this solution was transferred to the above suspension with a syringe. Subsequent heating in an oil bath at 70 degrees Celsius overnight. LC-MS showed that 14 was substantially consumed up and a product was formed. The reaction system was diluted with ethyl acetate and filtered through a layer of diatomaceous earth. The filtrate was spin-dried and subjected to silica gel column chromatography to obtain the thio product (4.1 mmol). According to the UMI-77 synthesis route (J. Med. Chem. 2014, 57, 4111-4133), the nitro group was reduced with reduced iron powder in acetic acid solvent, accompanied by the removal of the TMS protective group on the alkynyl group. After silica gel column chromatography, naphthylamine intermediate (3.5 mmol) was obtained. The naphthylamine intermediate was then sulfonylated according to the UMI-77 synthetic route (J. Med. Chem. 2014, 57, 4111-4133) to obtain the sulfonamide intermediate (3.2 mmol). This sulfonamide intermediate (3.2 mmol) was dissolved in a 2:1 mixed solvent of methanol and DMF, cuprous iodide (0.1 eq) was added, $TMSN_3$ was added dropwise with stirring at room temperature, reacted overnight, LC-MS shows that a triazole product is formed, and a triazole product (1.7 mmol) is obtained by silica gel column chromatography. Compound I-10 was prepared by demethylating and oxidizing the triazole product according to the synthesis method of compound I-2.

The purified product I-10 was taken for structural characterization, LC-MS (ESI) m/z: 507, 509 $[M+H]^+$.

Example 11. Synthesis and Characterization of Compounds I-11-1 and I-11-2

Referring to the synthetic routes of compounds I-9-1 and I-9-2, compounds I-11-1 and I-11-2 can be prepared by replacing tetrazole

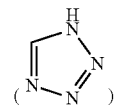

in the route with 1,2,3-triazole

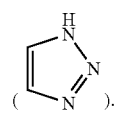

The purified product I-11-1 was taken for structural characterization, LC-MS (ESI) m/z: 507, 509 $[M+H]^+$.

The purified product I-11-2 was taken for structural characterization, LC-MS (ESI) m/z: 507, 509 $[M+H]^+$.

Example 12. Synthesis and Characterization of Compound I-12

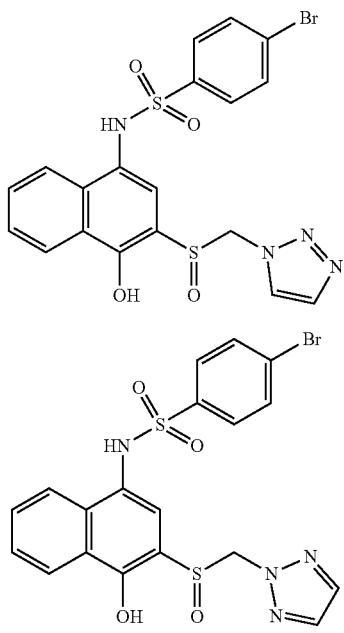

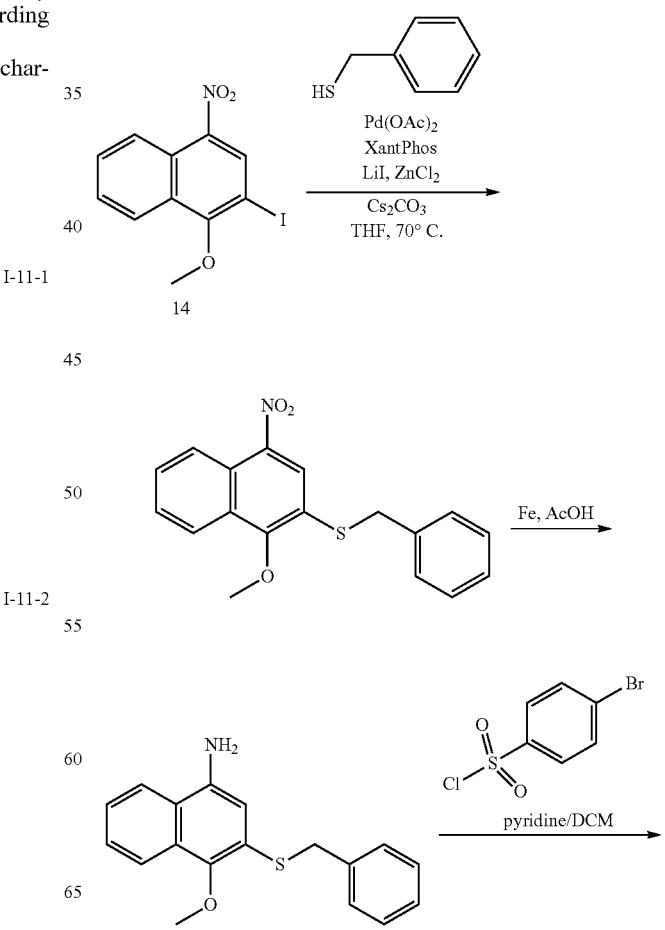

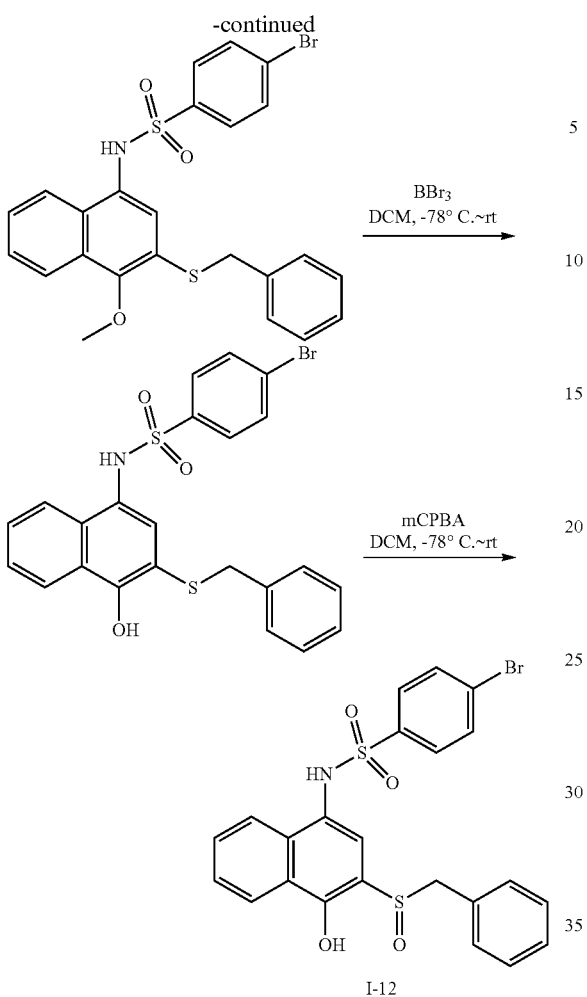

Using the known compound 14 as raw material, referring to the UMI-77 synthesis route (J. Med. Chem. 2014, 57, 4111-4133), replacing

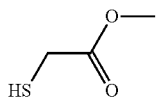

with

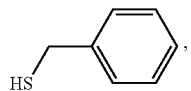

and in the last step oxidizing the sulfoxide with mCPBA according to the synthesis of compound I-1, compound I-12 can be prepared.

The purified product I-12 was taken for structural characterization, $^1$H-NMR (400 MHZ, DMSO-d 6) δ 10.92 (br, 1H), 10.11 (s, 1H), 8.24 (d, J=9.6 Hz, 1H), 7.99 (d, J=9.6 Hz, 1H), 7.58-7.56 (m, 2H), 7.31-7.26 (m, 5H), 7.14-7.11 (m, 2H), 7.09-7.06 (m, 2H), 7.02 (s, 1H), 4.27 (d, J=12.4 Hz, 1H), 3.91 (d, J=12.4 Hz, 1H). LC-MS (ESI) m/z: 516, 518 [M+H]$^+$.

Example 13. Synthesis and Characterization of Compound I-13-1

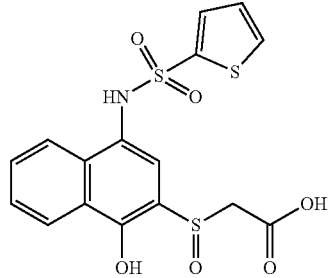

Using intermediate 2 as raw material, according to the synthesis method of UMI-77 and compound I-1, compound I-13-1 can be prepared by replacing the

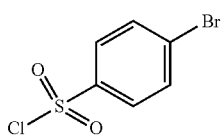 [SMILES: O=S(=O)(Cl)c1ccc(Br)cc1]

with

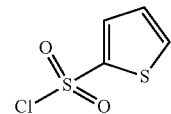

in the synthesis route.

The purified product I-13-1 was taken for structural characterization, $^1$H-NMR (400 MHZ, DMSO-d6) δ 13.19 (br, 1H), 10.96 (br, 1H), 10.23 (s, 1H), 8.29-8.26 (m, 1H), 8.03-8.00 (m, 1H), 7.88 (dd, J=2.0, 5.2 Hz, 1H), 7.60-7.54 (m, 2H), 7.39-7.37 (m, 1H), 7.31 (s, 1H), 7.09-7.06 (m, 1H), 4.02 (d, J=14.4 Hz, 1H), 3.48 (d, J=14.0 Hz, 1H). LC-MS (ESI) m/z: 410 [MH]$^-$.

Example 14. Synthesis and Characterization of Compound I-14-1

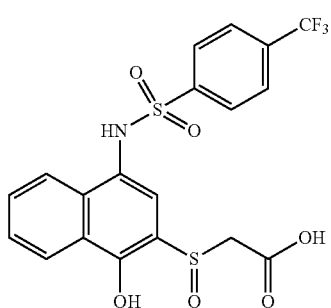

Using intermediate 2 as raw material, compound I-14-1 can be prepared according to the synthesis method of UMI-77 and compound I-1 by replacing the

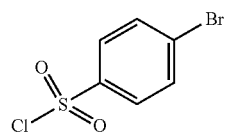

with

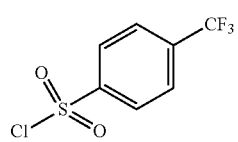 [SMILES: O=S(=O)(Cl)c1ccc(C(F)(F)F)cc1]

in the synthesis route.

The purified product I-14-1 was taken for structural characterization, 1H-NMR (400 MHZ, DMSO-d6) δ 10.28 (s, 1H), 8.26-8.37 (m, 1H), 7.97-7.94 (m, 1H), 7.88 (d, J=8.0 Hz, 2H), 7.82 (d, J=8.0 Hz, 2H), 7.58-7.51 (m, 2H), 7.16 (s, 1H), 3.95 (d, J=14.0 Hz, 1H), 3.42 (d, J=14.0 Hz, 1H). LC-MS (ESI) m/z: 472 [MH]⁻.

Example 15. Synthesis and Characterization of Compound I-15-1

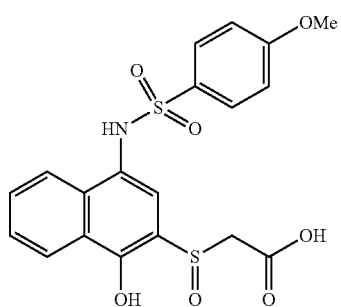

I-15-1

Using intermediate 2 as raw material, compound I-15-1 can be prepared according to the synthesis method of UMI-77 and compound I-1 by replacing the

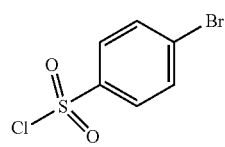

with

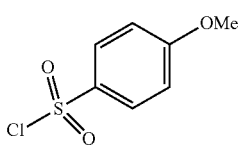 [SMILES: COc1ccc(S(=O)(=O)Cl)cc1]

in the synthesis route.

The purified product I-15-1 was taken for structural characterization, LC-MS (ESI) m/z: 434 [MH]⁻.

Example 16. Synthesis and Characterization of Compound I-16-1

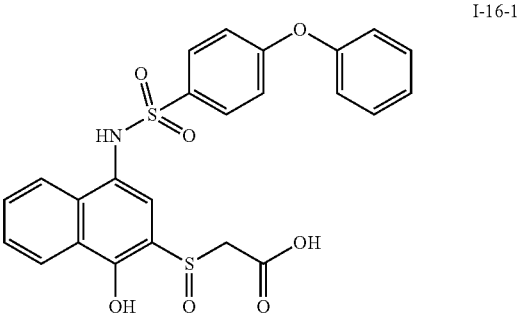 [SMILES: O=C(O)CS(=O)c1cc(NS(=O)(=O)c2ccc(Oc3ccccc3)cc2)c2ccccc2c1O]

I-16-1

Using intermediate 2 as raw material, compound I-16-1 can be prepared according to the synthesis method of UMI-77 and compound I-1 by replacing the

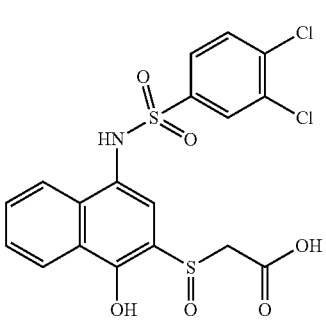

with

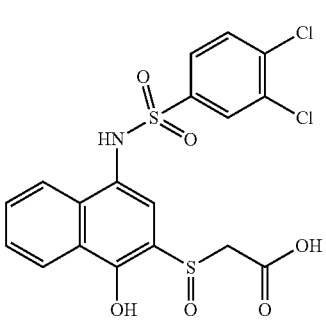

in the synthesis route.

The purified product I-16-1 was taken for structural characterization, 1H-NMR (400 MHZ, DMSO-d6) δ 9.90 (s, 1H), 8.25-8.22 (m, 1H), 8.05-8.02 (m, 1H), 7.59-7.56 (m, 4H), 7.44-7.39 (m, 2H), 7.22-7.18 (m, 1H), 7.12 (s, 1H), 7.07-7.04 (m, 2H)), 7.02-7.00 (m, 2H), 3.95 (d, J=14.4 Hz, 1H), 3.44 (d, J=14.4 Hz, 1H). LC-MS (ESI) m/z: 496 [MH]⁻.

Example 17. Synthesis and Characterization of Compound I-17

I-17-1

Using intermediate 2 as raw material, compound I-17-1 can be prepared according to the synthesis method of UMI-77 and compound I-1 by replacing the

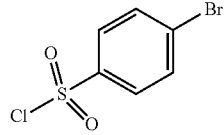

with

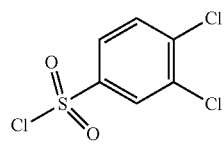 [SMILES: O=S(=O)(Cl)c1ccc(Cl)c(Cl)c1]

in the synthesis route.

The purified product I-17-1 was taken for structural characterization, $^1$H-NMR (400 MHZ, DMSO-d6) δ 13.18 (br, 1H), 11.04 (br, 1H), 10.26 (s, 1H), 8.30-8.27 (m, 1H), 8.03-8.00 (m, 1H), 7.81-7.77 (m, 2H), 7.62-7.55 (m, 3H), 7.17 (s, 1H), 4.02 (d, J=14.0 Hz, 1H), 3.45 (d, J=14.0 Hz, 1H). LC-MS (ESI) m/z: 472 [MH]$^-$.

Example 18. Synthesis and Characterization of Compound I-18

I-18-1

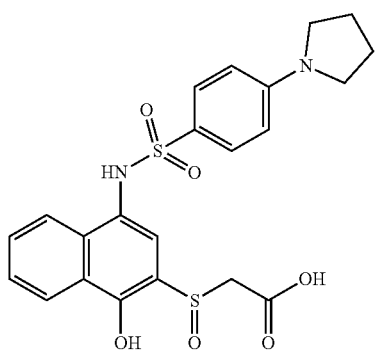

Using intermediate 2 as raw material, compound I-18-1 can be prepared according to the synthesis method of UMI-77 and compound I-1 by replacing the

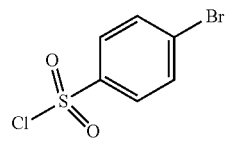 [SMILES: O=S(=O)(Cl)c1ccc(Br)cc1]

with

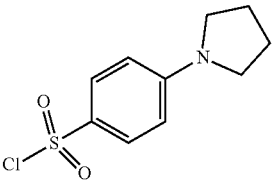 [SMILES: O=S(=O)(Cl)c1ccc(N2CCCC2)cc1]

in the synthesis route.

The purified product I-18-1 was taken for structural characterization, LC-MS (ESI) m/z: 473 [MH]$^-$.

Example 19. Synthesis and Characterization of Compound I-19

I-19-1

Using intermediate 2 as raw material, compound I-19-1 can be prepared according to the synthesis method of UMI-77 and compound I-1 by replacing the

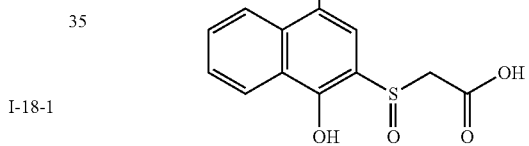

with

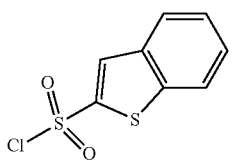 [SMILES: O=S(=O)(Cl)c1cc2ccccc2s1]

in the synthesis route.

The purified product I-19-1 was taken for structural characterization, LC-MS (ESI) m/z: 460 [MH]$^-$.

Example 20, Synthesis and Characterization of Compound I-20-1

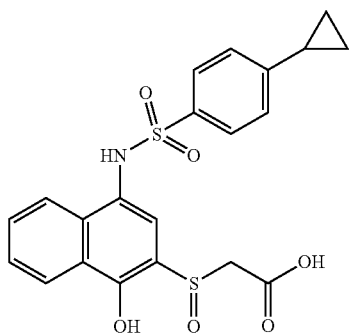

Using intermediate 2 as raw material, compound I-20-1 can be prepared according to the synthesis method of UMI-77 and compound I-1 by replacing the

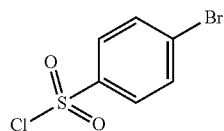

with

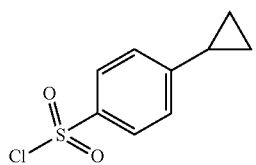 [SMILES: O=S(=O)(Cl)c1ccc(C2CC2)cc1]

in the synthesis route.

The purified product I-20-1 was taken for structural characterization, 1H-NMR (400 MHZ, DMSO-d6) δ 9.90 (s, 1H), 8.28-8.23 (m, 1H), 8.06-8.02 (m, 1H), 7.59-7.52 (m, 2H), 7.50-7.44 (m, 2H), 7.18-7.13 (m, 3H), 3.94 (d, J=14.4 Hz, 1H), 3.39 (d, J=14.4 Hz, 1H), 1.99-1.93 (m, 1H), 1.01-0.95 (m, 2H), 0.76-0.69 (m, 2H). LC-MS (ESI) m/z: 444 [MH]$^-$.

Example 21. Synthesis and Characterization of Compound I-21-1

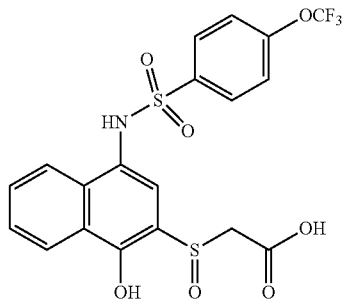

Using intermediate 2 as raw material, compound I-21-1 can be prepared according to the synthesis method of UMI-77 and compound I-1 by replacing the

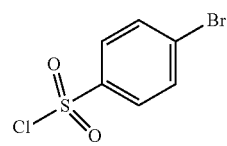 [SMILES: O=S(=O)(Cl)c1ccc(Br)cc1]

with

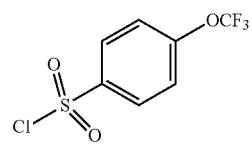 [SMILES: O=S(=O)(Cl)c1ccc(OC(F)(F)F)cc1]

in the synthesis route.

The purified product I-21-1 was taken for structural characterization, $^1$H-NMR (400 MHZ, DMSO-d6) δ 10.17 (s, 1H), 8.24 (d, J=8.0 Hz, 1H), 7.93 (d, J=8.0 Hz, 1H), 7.74-7.70 (m, 2H), 7.58-7.48 (m, 2H), 7.48-7.45 (m, 2H), 7.19 (s, 1H), 3.98 (d, J=14.4 Hz, 1H), 3.44 (d, J=14.4 Hz, 1H). LC-MS (ESI) m/z: 488 [MH]$^-$.

Example 22. Synthesis and Characterization of Compound I-22-1

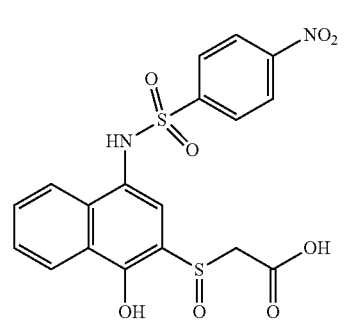

Using intermediate 2 as raw material, compound I-22-1 can be prepared according to the synthesis method of UMI-77 and compound I-1 by replacing the

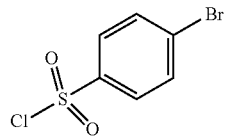

with

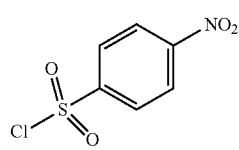 [SMILES: O=[N+]([O-])c1ccc(S(=O)(=O)Cl)cc1]

in the synthesis route.

The purified product I-22-1 was taken for structural characterization, 1H-NMR (400 MHZ, DMSO-d6) δ 10.41 (s, 1H), 8.35-8.31 (m, 2H), 8.27-8.24 (m, 1H), 8.01-7.97 (m, 1H), 7.90-7.86 (m, 2H), 7.59-7.54 (m, 2H), 7.13 (s, 1H), 3.96 (d, J=14.4 Hz, 1H), 3.40 (d, J=14.4 Hz, 1H). LC-MS (ESI) m/z: 449 [MH]⁻.

Example 23. Synthesis and Characterization of Compound I-23-1

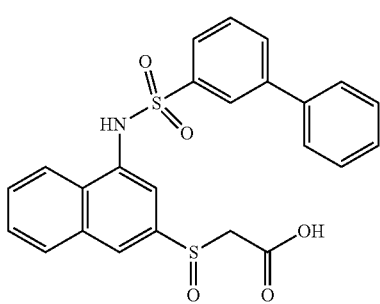

I-23-1

Using intermediate 2 as raw material, compound I-23-1 can be prepared according to the synthesis method of UMI-77 and compound I-1 by replacing the

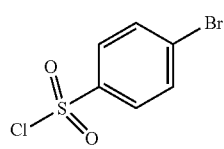

with

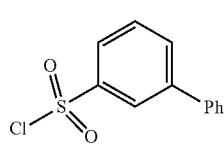 [SMILES: O=S(=O)(Cl)c1cccc(-c2ccccc2)c1]

in the synthesis route.

The purified product I-23-1 was taken for structural characterization, 1H-NMR (400 MHZ, DMSO-d6) δ 10.10 (s, 1H), 8.26-8.23 (m, 1H), 8.07-8.03 (m, 1H), 7.89-7.86 (m, 1H), 7.85-7.83 (m, 1H), 7.62-7.51 (m, 6H), 7.50-7.45 (m, 2H), 7.44-7.39 (m, 1H), 7.28 (s, 1H)), 3.95 (d, J=14.4 Hz, 1H), 3.37 (d, J=14.4 Hz, 1H). LC-MS (ESI) m/z: 480 [MH]⁻.

Example 24. Synthesis and Characterization of Compound I-24-1

I-24-1

Using intermediate 2 as raw material, compound I-24-1 can be prepared according to the synthesis method of UMI-77 and compound I-1 by replacing the

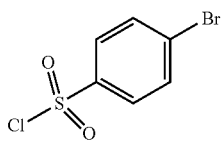 [SMILES: O=S(=O)(Cl)c1ccc(Br)cc1]

with

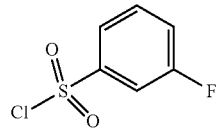 [SMILES: O=S(=O)(Cl)c1cccc(F)c1]

in the synthesis route.

The purified product I-24-1 was taken for structural characterization, 1H-NMR (400 MHZ, DMSO-d6) δ 10.19 (s, 1H), 8.27-8.25 (m, 1H), 8.02-7.99 (m, 1H), 7.59-7.54 (m, 3H), 7.51-7.46 (m, 2H), 7.43-7.39 (m, 1H), 7.20 (s, 1H), 4.00 (d, J=14.4 Hz, 1H), 3.43 (d, J=14.4 Hz, 1H). LC-MS (ESI) m/z: 422 [MH]⁻.

Example 25. Synthesis and Characterization of Compound I-25-1

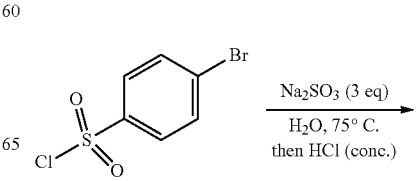

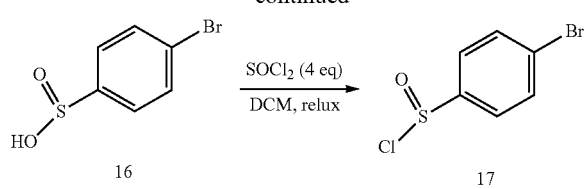

Dissolving Na$_2$SO$_3$ (3.8 g, 30 mmol) in 30 mL deionized water, and adding p-bromobenzenesulfonyl chloride (2.6 g, 10 mmol) in batches while stirring, heating in an oil bath at 75° C. for 5 hours, after cooling, adding concentrated hydrochloric acid dropwise, and a white solid will precipitate. After suction filtration, the obtained solid was recrystallized in water to obtain intermediate 16 (1.3 g). Intermediate 16 was suspended in 80 mL DCM, and thionyl chloride (4 eq) was added dropwise. After the dropwise addition, the oil bath was heated to reflux. After 5 hours, the solvent was removed by rotary evaporation, and the residual thionyl chloride was taken out with toluene to obtain the intermediate 17 (626 mg).

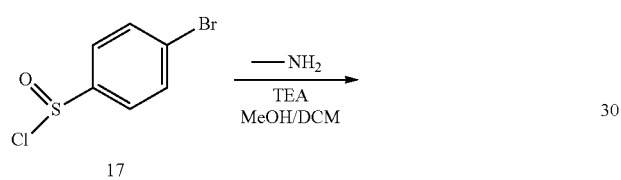

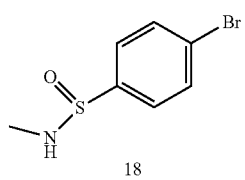

Intermediate 17 (48 mg, 0.2 mmol) was suspended in 1 mL DCM. An alcohol solution of methylamine (1.5 eq) was added while cooling in an ice-water bath, and then triethylamine (2 eq) was added. The mixture was allowed to return to room temperature naturally and stirred for 2 hours. LC-MS shows that intermediate 18 is formed. Purification by silica gel column chromatography (EA in hexane=65% v/v), Intermediate 18 was obtained as a pale yellow solid (30 mg).

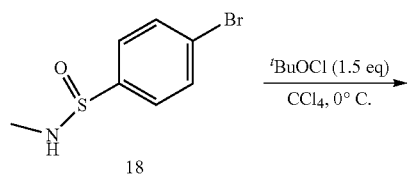

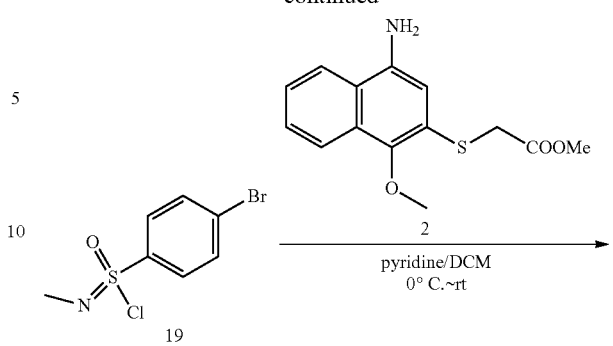

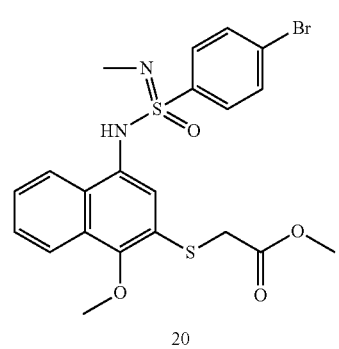

Intermediate 18 (30 mg, 0.13 mmol) was suspended in 0.5 mL carbon tetrachloride, stirred in an ice-water bath, and tert-butyloxychloride (1.5 eq) was added, and the solid was dissolved immediately. Continue stirring for 1 hour and the intermediate 19 was obtained by rotary evaporation to remove the low-boiling substances. Then 19 was dissolved in 0.5 mL DCM and stirred in an ice-water bath. Intermediate 2 (1 eq, prepared with referring to J. Med. Chem. 2014, 57, 4111-4133) was dissolved in 0.3 mL pyridine, and this pyridine solution was added dropwise to the DCM solution of 19, returned to room temperature naturally and stir overnight. LC-MS shows the formation of intermediate 20. Purified by silica gel column chromatography (EA in hexane=40% v/v), the intermediate 20 is obtained as an oil product (51 mg).

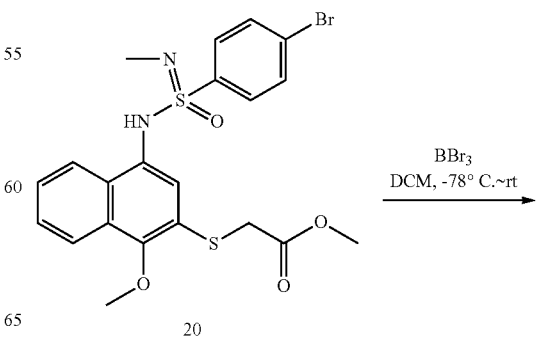

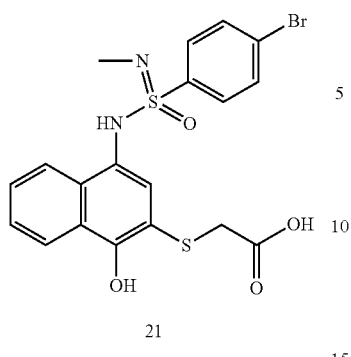

Intermediate 20 (51 mg, 0.1 mmol) was dissolved in 0.5 mL DCM, and BBr3 solution of DCM (0.2 mL, 1 M in DCM) was added dropwise with cooling in a dry ice-ethanol bath, slowly returned to room temperature and stirred for 3 hours. LC-MS shows that 20 is completely consumed and intermediate 21 is formed. The reaction was quenched by adding deionized water dropwise, and extracted three times with DCM. The organic phases were combined, the organic solvent was evaporated by rotary evaporation, and the product was purified by preparative HPLC (MeCN/H$_2$O/TFA) to obtain intermediate 21 (13 mg). The purified 21 was taken for structural characterization, LC-MS (ESI) m/z: 479, 481 [MH]$^-$. $^1$H-NMR (400 MHZ, DMSO-d$_6$) δ (ppm): 9.13 (s, 1H), 8.36-8.28 (m, 1H), 8.14-8.06 (m, 1H), 7.93 (d, J=8.4 Hz, 2H), 7.83 (d, J=8.4 Hz, 2H), 7.55-7.39 (m, 3H), 7.22 (s, 1H), 3.61 (s, 2H), 2.41 (s, 3H).

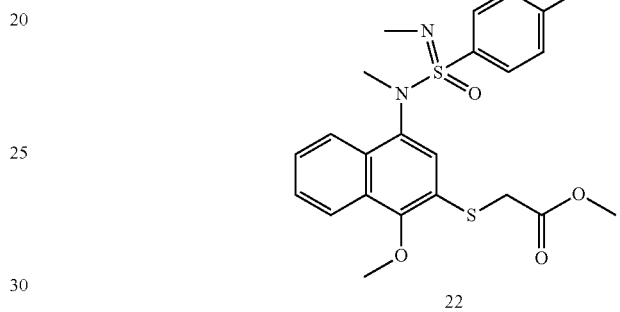

Using intermediate 21 (13 mg) as raw material, compound I-25-1 (4 mg) was prepared according to the synthesis method of compound I-1.

The purified product I-25-1 was taken for structural characterization, LC-MS (ESI) m/z: 495, 497 [MH]$^-$.

Example 26. Synthesis and Characterization of Compound I-26

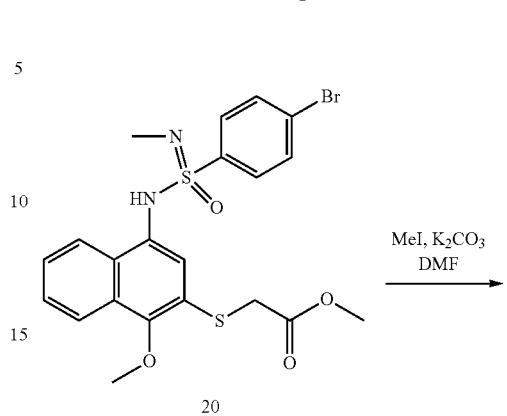

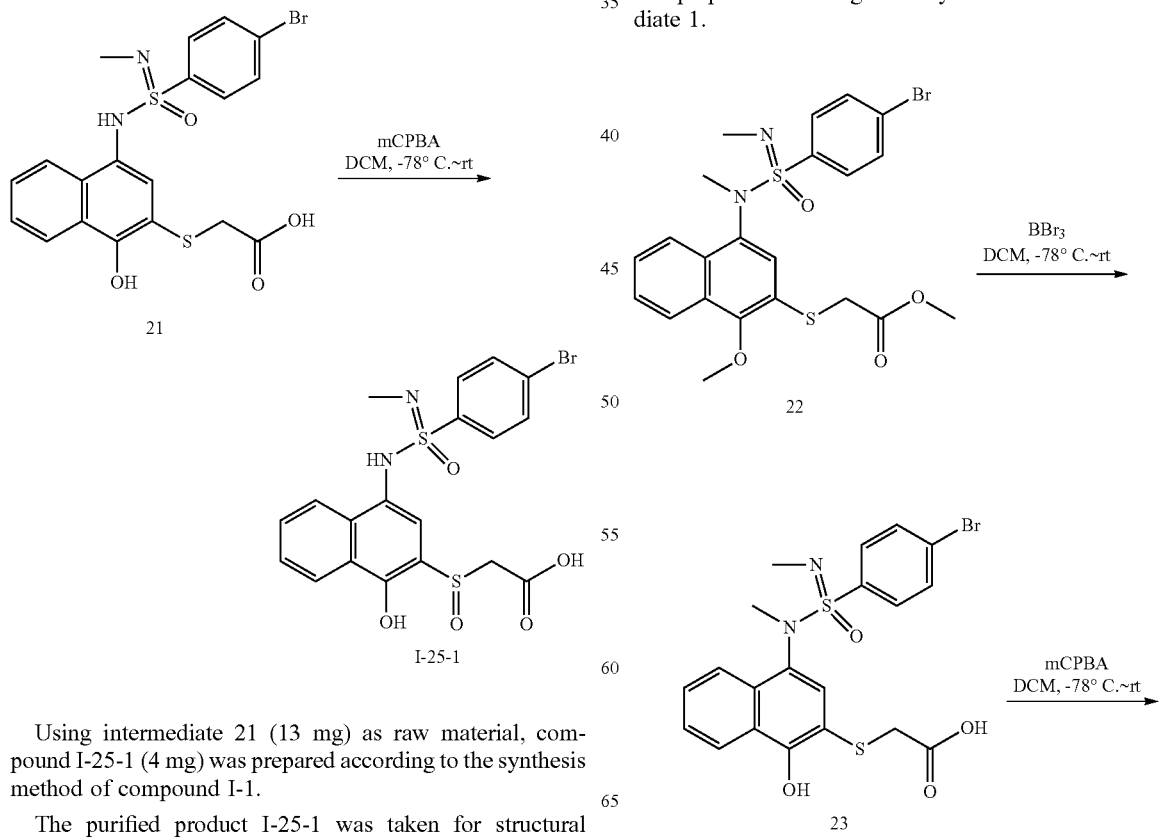

Using intermediate 20 as raw material, intermediate 22 was prepared according to the synthesis method of intermediate 1.

85

-continued

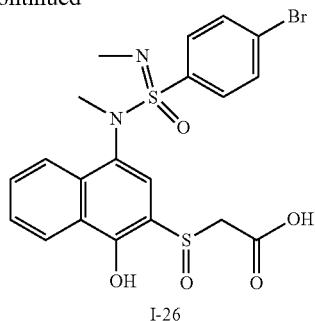

I-26

Using intermediate 22 as raw material, compound I-26 was prepared according to the synthesis method of compound I-2.

The purified product I-26 was taken for structural characterization, LC-MS (ESI) m/z: 509, 511 [MH]⁻.

Example 27. Synthesis and Characterization of Compound I-27

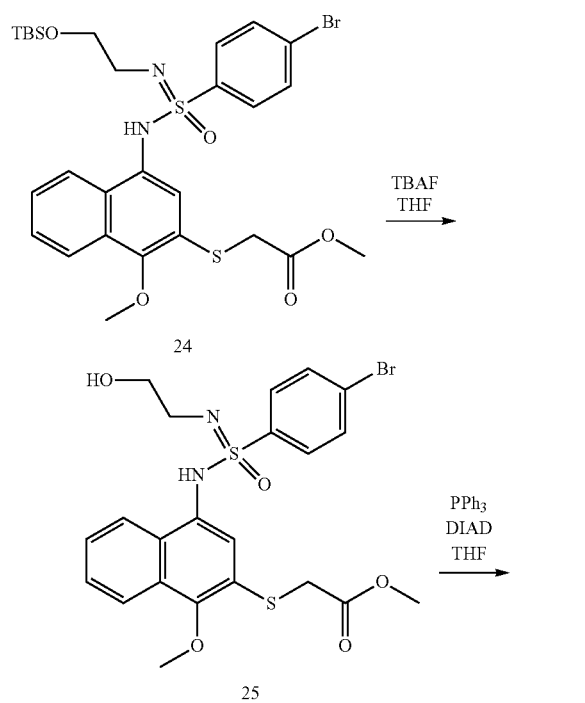

86

According to the synthesis method of intermediate 20, intermediate 24 can be prepared by replacing methylamine with

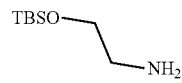

in the synthesis route. Intermediate 24 (1.9 mmol) was dissolved in THF, stirred at room temperature and added 1M TBAF to THE solution dropwise, continued stirring for one hour until TBS was completely removed. Intermediate 25 (1.8 mmol) was obtained by silica gel column chromatography. intermediate 25 (1.8 mmol) and triphenylphosphine (1.2 eq) was dissolved in anhydrous THF, stirred at room temperature and added DIAD (1.2 eq) dropwise, continued stirring at room temperature overnight, LC-MS shows that the cyclization product 26 is formed, and intermediate 26 (0.8 mmol) was obtained by silica gel column chromatography.

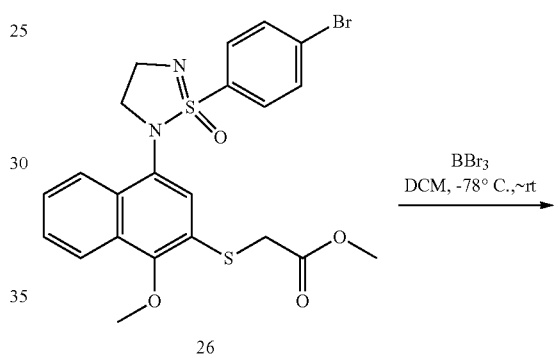

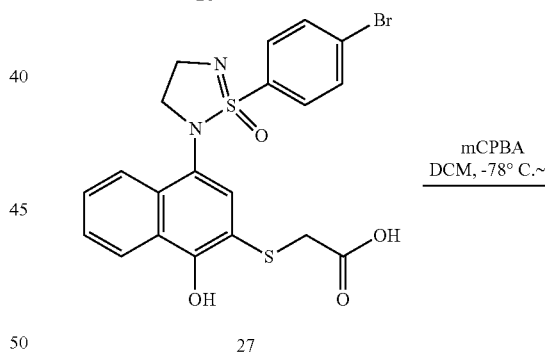

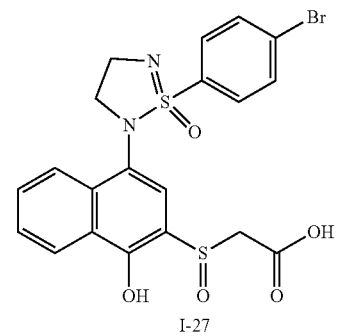

Using intermediate 26 as raw material, compound I-27 can be prepared according to the synthesis method of compound I-2.

The purified product I-27 was taken for structural characterization, LC-MS (ESI) m/z: 507, 509 [MH]⁻.

Example 28. Synthesis and Characterization of Compound I-28

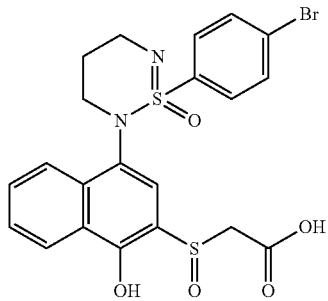

I-28

According to the synthesis method of compound I-27, compound I-28 can be prepared by replacing

TBSO—\—NH₂ with

TBSO—\—NH₂ in the synthesis route.

The purified product I-28 was taken for structural characterization, LC-MS (ESI) m/z: 521, 523 [MH]⁻.

Example 29. Synthesis and Characterization of Compound I-29

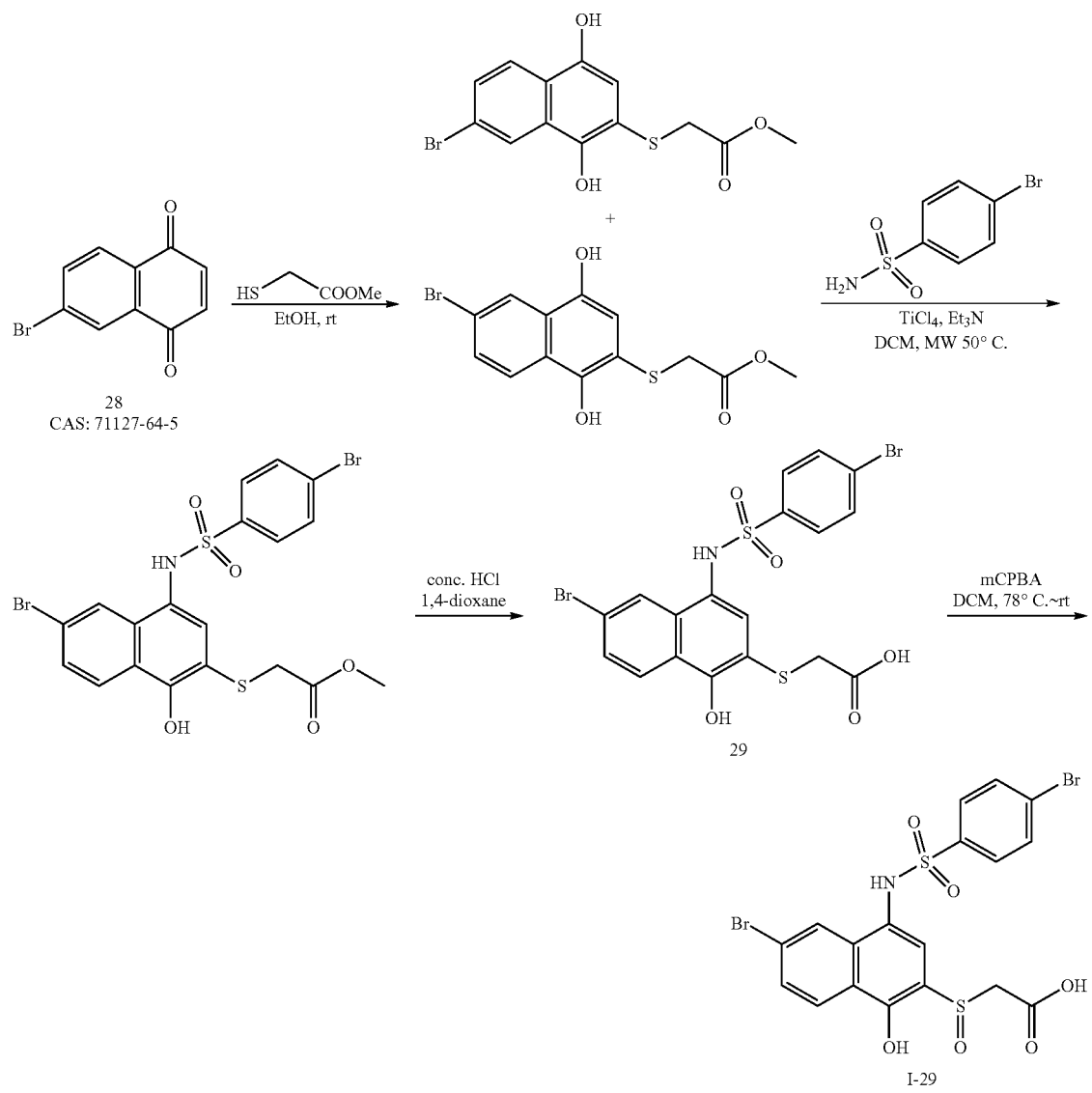

Using the known compound 28 (CAS: 71127-64-5) (5.0 mmol) as raw material, intermediate 29 (0.8 mmol) was prepared according to the synthetic method in the literature (J. Med. Chem. 2012, 55, 1978-1998). Then, the intermediate 29 is oxidized according to the synthesis method of compound I-1 to prepare compound I-29.

The purified product I-29 was taken for structural characterization: LC-MS (ESI) m/z: 562 [MH]⁻.

Example 30. Synthesis and Characterization of Compound I-30

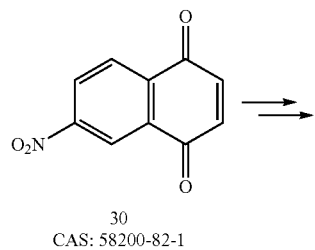

30
CAS: 58200-82-1

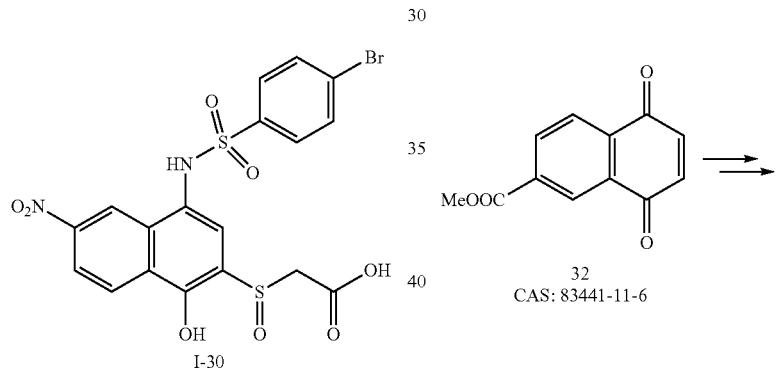

I-30

Compound I-30 can be prepared by using the known compound 30 (CAS: 58200-82-1) as raw material and using the same synthetic route as compound I-29. Take the purified product I-30 for structural characterization: LC-MS (ESI) m/z: 527, 529 [MH]⁻.

Example 31. Synthesis and Characterization of Compound I-31

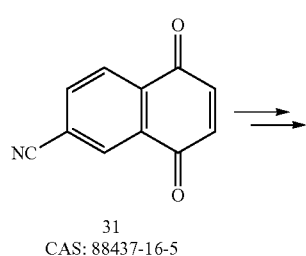

31
CAS: 88437-16-5

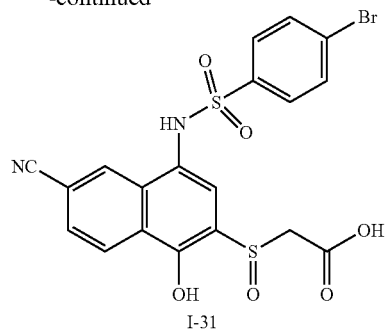

I-31

Compound I-31 can be prepared by using the known compound 31 (CAS: 88437-16-5) as raw material and using the same synthetic route as compound I-29.

The purified product I-31 was taken for structural characterization: LC-MS (ESI) m/z: 507, 509 [MH]⁻.

Example 32. Synthesis and Characterization of Compound I-32

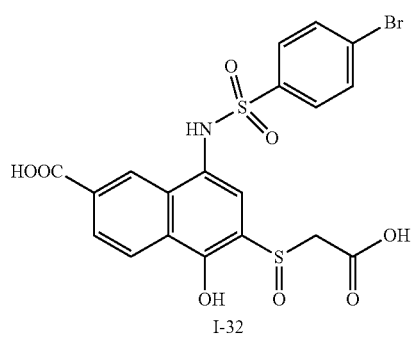

32
CAS: 83441-11-6

I-32

Compound I-32 can be prepared by using the known compound 32 (CAS: 83441-11-6) as raw material and using the same synthetic route as compound I-29.

The purified product I-32 was taken for structural characterization: LC-MS (ESI) m/z: 526, 528 [MH]⁻.

Example 33. Synthesis and Characterization of Compound I-33

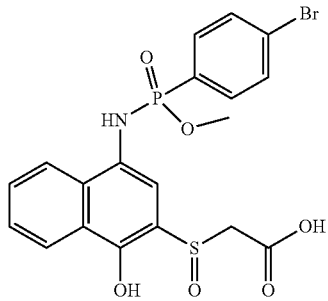

I-33

Using intermediate 2 as raw material, referring to the synthetic methods of UMI-77 and compound I-1, compound I-33 can be prepared by replacing

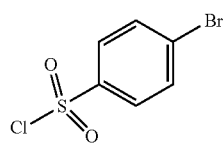

with

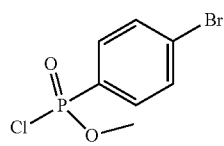

in the synthetic route.

The purified product I-33 was taken for structural characterization, LC-MS (ESI) m/z: 496, 498 [MH]⁻.

Example 34: Synthesis and Characterization of Compound I-34

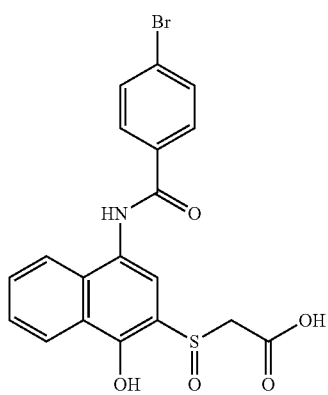

I-34

Using intermediate 2 as raw material, compound I-34 can be prepared according to the synthesis method of UMI-77 and compound I-34 by replacing

with

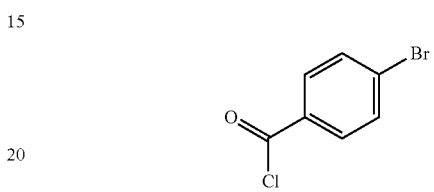

in the synthesis route.

The purified product I-34 was taken for structural characterization, ¹H-NMR (400 MHZ, DMSO-d6) δ 10.49 (s, 1H), 8.35-8.32 (m, 1H), 8.04-8.02 (m, 2H), 7.97-7.93 (m, 1H), 7.80-7.77 (m, 2H), 7.71 (s, 1H), 7.68-7.61 (m, 2H), 4.13 (d, J=14.4 Hz, 1H), 3.69 (d, J=14.4 Hz, 1H). LC-MS (ESI) m/z: 446, 448 [MH]⁻.

Example 35. Synthesis and Characterization of Compound I-35-1

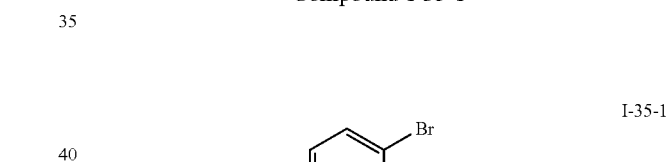

I-35-1

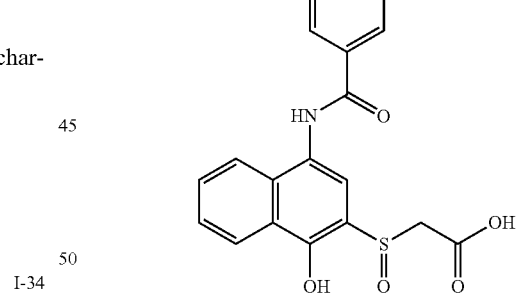

Using intermediate 2 as raw material, compound I-35-1 can be prepared according to the synthesis method of UMI-77 and compound I-1 by replacing the

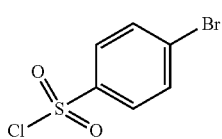 [SMILES: O=S(=O)(Cl)c1ccc(Br)cc1]

with

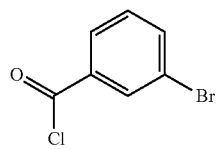

in the synthesis route.

The purified product I-35-1 was taken for structural characterization, $^1$H-NMR (400 MHZ, DMSO-d6) δ 10.51 (s, 1H), 8.34-8.31 (m, 1H), 8.26 (m, 1H)), 8.07-8.05 (m, 1H), 7.95-7.93 (m, 1H), 7.83-7.81 (m, 1H), 7.70 (s, 1H), 7.66-7.60 (m, 2H), 7.53 (t, J=8.0 Hz, 2H), 4.11 (d, J=14.4 Hz, 1H), 3.69 (d, J=14.4 Hz, 1H). LC-MS (ESI) m/z: 446, 448 [MH]$^-$.

Example 36. Synthesis and Characterization of Compound I-36

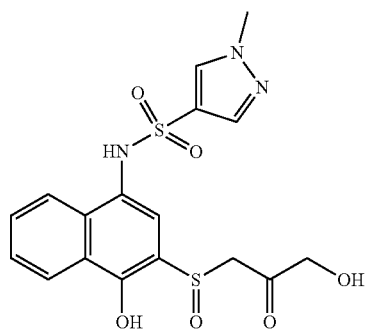 [SMILES: Cn1cc(S(=O)(=O)Nc2cc(S(=O)CC(=O)CO)c(O)c3ccccc23)cn1]

Using intermediate 2 as raw material, compound I-36 can be prepared according to the synthesis method of UMI-77 and compound I-1 by replacing

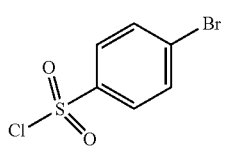

with

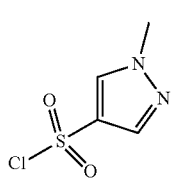

in the synthesis route.

The purified product I-36 was taken for structural characterization, $^1$H-NMR (400 MHZ, DMSO-d6) δ 9.69 (s, 1H), 8.25-8.23 (m, 1H), 8.12-8.10 (m, 1H), 8.00 (s, 1H), 7.61-7.60 (m, 2H), 7.59-7.52 (m, 1H), 7.23 (s, 1H), 3.86 (d, J=14.4 Hz, 1H), 3.80 (s, 3H), 3.61 (d, J=14.4 Hz, 1H). LC-MS (ESI) m/z: 408 [MH]$^-$.

Example 37. Synthesis and Characterization of Compound I-37

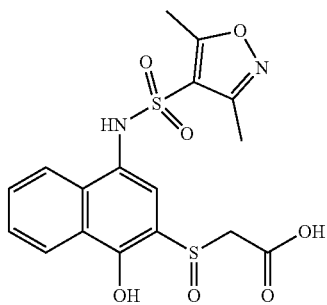 [SMILES: Cc1noc(C)c1S(=O)(=O)Nc1cc(S(=O)CC(=O)O)c(O)c2ccccc12]

Using intermediate 2 as raw material, compound I-37 can be prepared according to the synthesis method of UMI-77 and compound I-1 by replacing

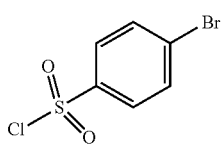 [SMILES: O=S(=O)(Cl)c1ccc(Br)cc1]

with

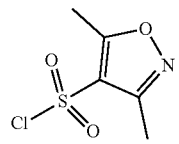

in the synthesis route.

The purified product I-37 was taken for structural characterization, LC-MS (ESI) m/z: 423 [MH]$^-$.

Example 38. Synthesis and Characterization of Compound I-38

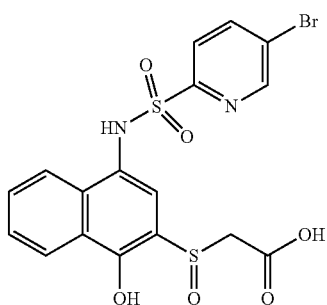 [SMILES: O=C(O)CS(=O)c1cc(NS(=O)(=O)c2ccc(Br)cn2)c2ccccc2c1O]

Using intermediate 2 as raw material, compound I-38 can be prepared according to the synthesis method of UMI-77 and compound I-1 by replacing with

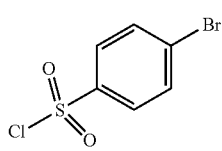

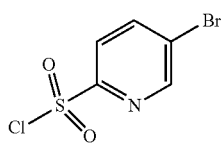 [SMILES: O=S(=O)(Cl)c1ccc(Br)cn1]

in the synthesis route.

The purified product I-38 was taken for structural characterization, LC-MS (ESI) m/z: 483, 485 [MH]⁻.

Example 39. Synthesis and Characterization of Compound I-39

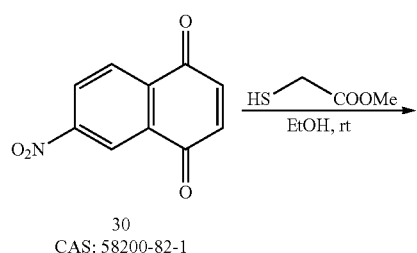

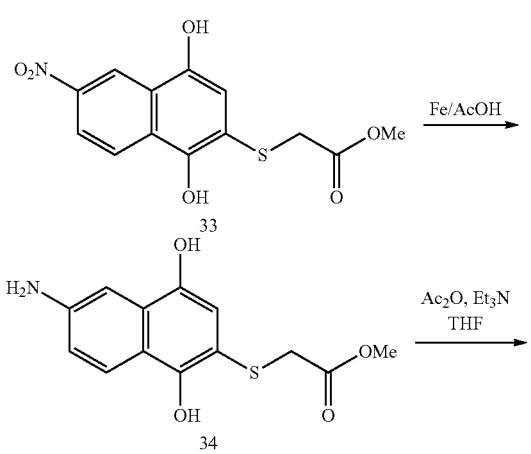

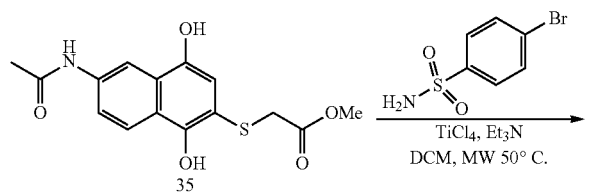

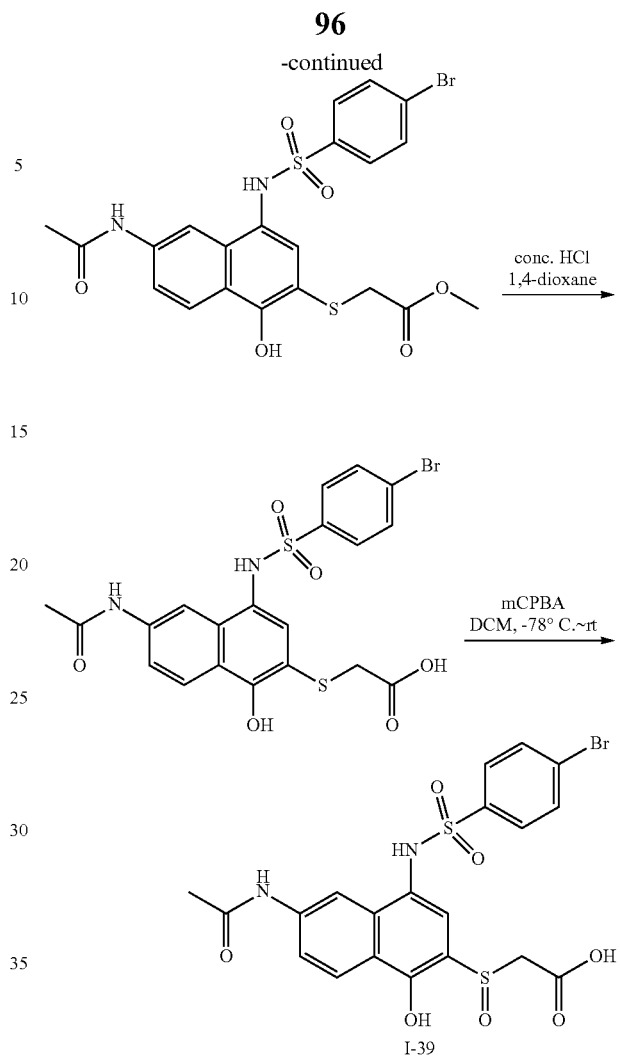

Using the known compound 30 (CAS: 58200-82-1) (10.0 mmol) as raw material, according to the synthesis method of the literature (J. Med. Chem. 2012, 55, 1978-1998), excess amount of

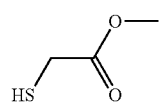

can be subjected to nucleophilic substitution in ethanol and 30 was reduced to give intermediate 33 (7.1 mmol). Dissolve the 33 in acetic acid and add reduced iron powder (8.0 eq), heat and stir at 50 degrees until the nitro group is completely reduced to intermediate 34. Filter and concentrate the filtrate, dissolve the residue in THF, add triethylamine (5.0 eq), add acetic anhydride (2.0 eq) dropwise with stirring at room temperature, and stirring was continued until LC-MS shows that intermediate 34 is completely acetylated to obtain intermediate 35, and silica gel column chromatography was performed and intermediate 35 (3.8 mmol) was obtained. Subsequently, compound I-39 can be prepared using the same synthetic steps as compound I-29.

The purified product I-39 was taken for structural characterization, LC-MS (ESI) m/z: 539, 541 [MH]⁻.

Example 40. Synthesis and Characterization of Compound I-40-1

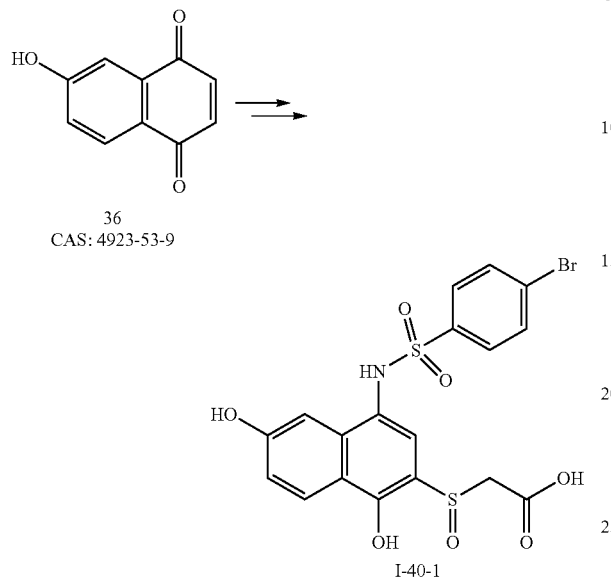

Using the known compound 36 (CAS: 4923-53-9) as raw material and using the same synthetic route as compound I-29, compound I-40-1 can be prepared.

The purified product I-40-1 was taken for structural characterization: LC-MS (ESI) m/z: 498, 500 [MH]⁻.

Example 41. Synthesis and Characterization of Compound I-41-1

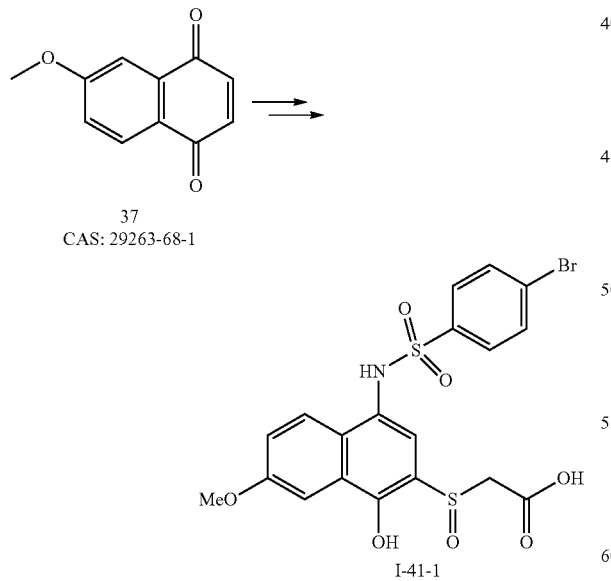

I-41-1 can be prepared by using the known compound 37 (CAS: 29263-68-1) as raw material and using the same synthetic route as compound I-29.

Take the purified product I-41-1 for structural characterization: LC-MS (ESI) m/z: 512, 514 [MH]⁻.

Example 42. Synthesis and Characterization of Compound I-42

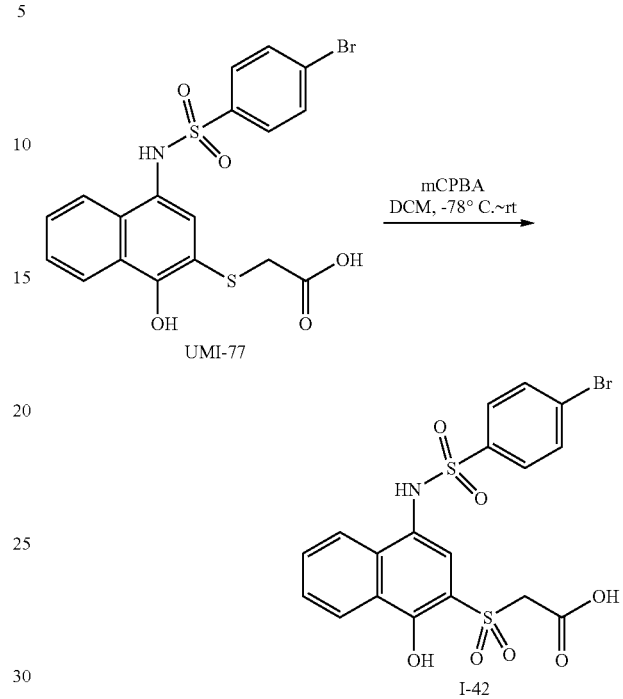

UMI-77 (15 mg, 0.032 mmol) was dissolved in DCM (0.5 mL) and stirred in a dry ice-ethanol bath. 2 equivalents of 85% mCPBA (13 mg, 0.064 mmol) was added, and then slowly returned to room temperature. The formed product I-42 was detected by LC-MS. The organic solvent was evaporated under reduced pressure, and the obtained crude product was purified by preparative HPLC (MeCN/H$_2$O/TFA) to obtain product I-42 (5 mg).

The purified product I-42 was taken for structural characterization, $^1$H-NMR (400 MHz, DMSO-d6) δ 10.14 (s, 1H), 8.37-8.34 (m, 1H), 7.97-7.95 (m, 1H)), 7.72-7.69 (m, 2H), 7.64-7.61 (m, 2H), 7.55-7.53 (m, 2H), 7.27 (s, 1H), 4.51 (s, 2H). LC-MS (ESI) m/z: 498, 500 [MH]⁻.

Example 43. Synthesis and Characterization of Compound I-7-2

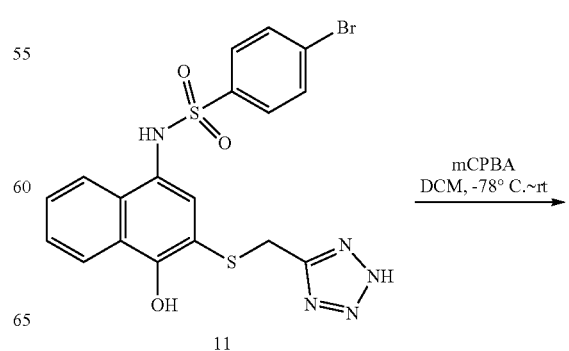

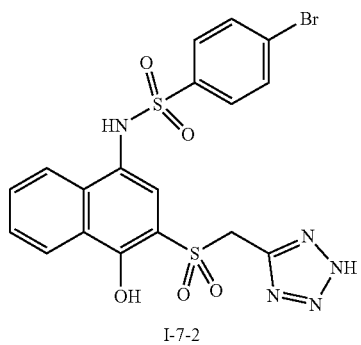

I-7-2

Using the known compound 11 (J. Med. Chem. 2014, 57, 4111-4133) (0.04 mmol) as raw material, compound I-7-2 (4 mg) was prepared according to the synthesis method of compound I-42.

The purified product I-7-2 was taken for structural characterization, LC-MS (ESI) m/z: 522, 524 [MH]⁻.

Example 44. Synthesis and Characterization of Compound I-13-2

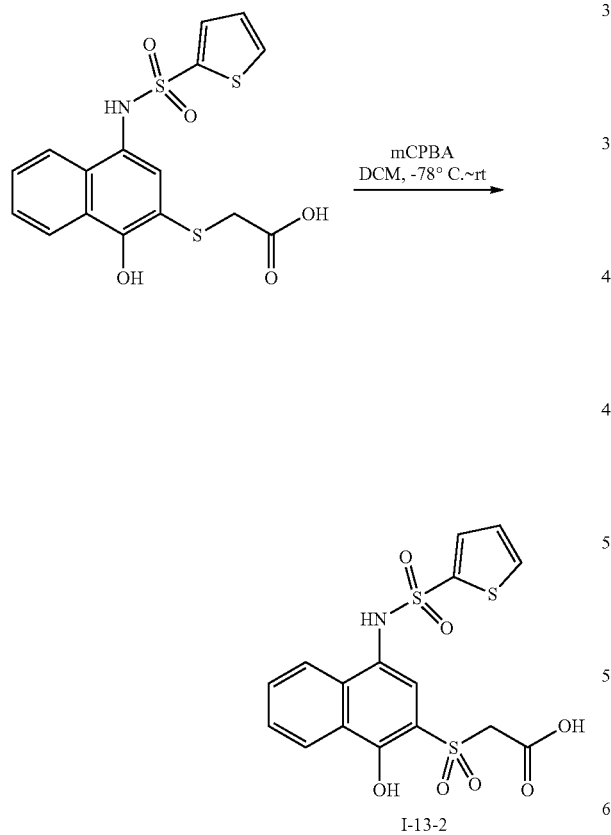

I-13-2

Compound I-13-2 (5 mg) was prepared according to the synthesis method of compounds I-13-1 and I-42.

The purified product I-13-2 was taken for structural characterization, LC-MS (ESI) m/z: 426 [MH]⁻.

Example 45. Synthesis and Characterization of Compound I-14-2

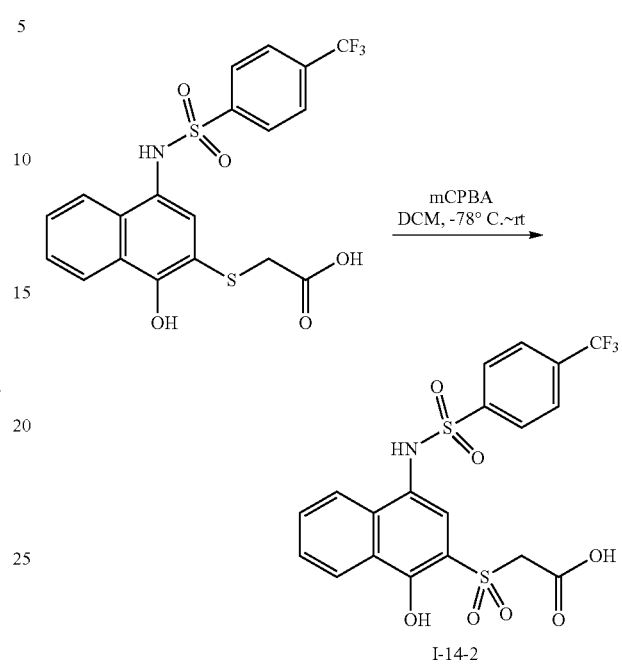

I-14-2

I-14-2 (7 mg) was prepared according to the synthesis method of compounds I-14-1 and I-42.

The purified product I-14-2 was taken for structural characterization, LC-MS (ESI) m/z: 488 [MH]⁻.

Example 46. Synthesis and Characterization of Compound I-15-2

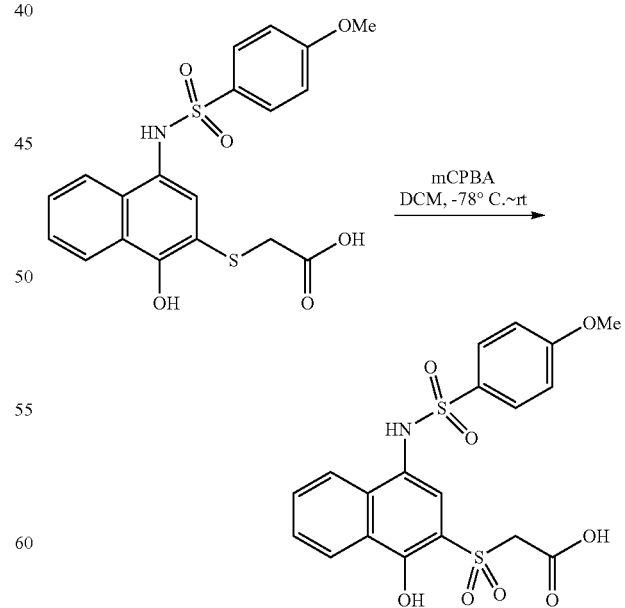

I-15-2

Compound I-15-2 (12 mg) was prepared according to the synthesis method of compounds I-15-1 and I-42.

The purified product I-15-2 was taken for structural characterization, LC-MS (ESI) m/z: 450 [MH]⁻.

Example 47. Synthesis and Characterization of Compound I-16-2

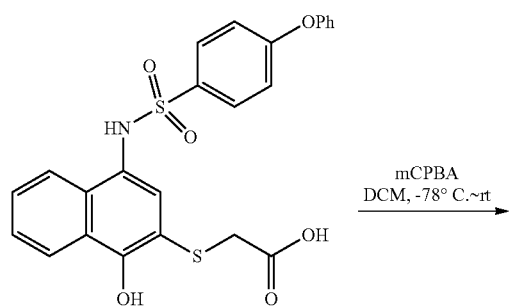

Compound I-16-2 (15 mg) was prepared according to the synthesis method of compounds I-16-1 and I-42.

The purified product I-16-2 was taken for structural characterization, LC-MS (ESI) m/z: 512 [MH]⁻.

Example 48. Synthesis and Characterization of Compound I-17-2

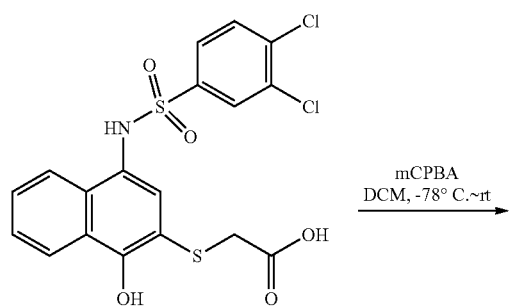

-continued

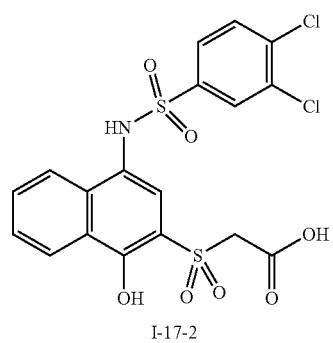

Compound I-17-2 (17 mg) was prepared according to the synthesis method of compounds I-17-1 and I-42.

The purified product I-17-2 was taken for structural characterization, LC-MS (ESI) m/z: 488 [MH]⁻.

Example 49. Synthesis and Characterization of Compound I-18-2

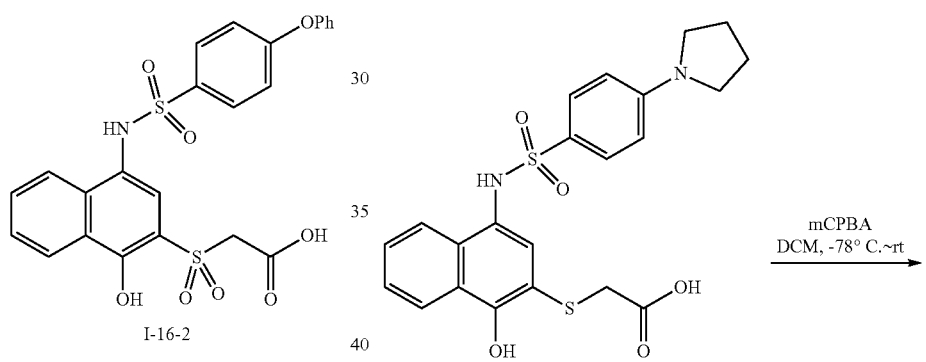

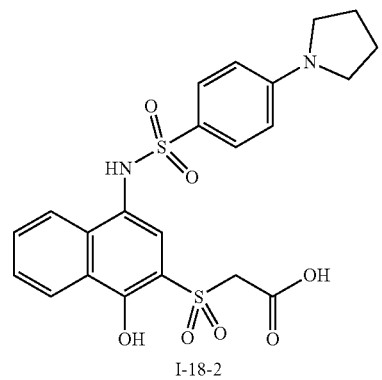

Compound I-18-2 (11 mg) was prepared according to the synthesis method of compounds I-18-1 and I-42.

The purified product I-18-2 was taken for structural characterization, LC-MS (ESI) m/z: 489 [MH]⁻.

Example 50, Synthesis and Characterization of Compound I-19-2

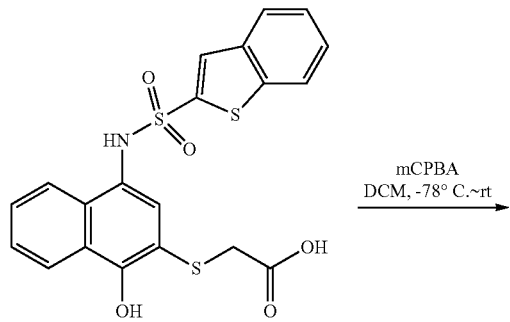

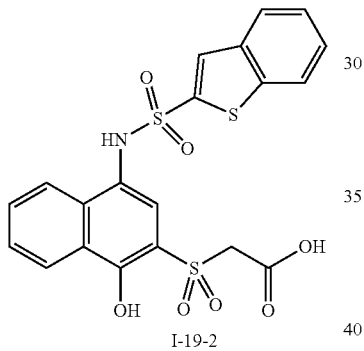

I-19-2

Compound I-19-2 (17 mg) was prepared according to the synthesis method of compounds I-19-1 and I-42.

The purified product I-19-2 was taken for structural characterization, LC-MS (ESI) m/z: 476 [MH]⁻.

Example 51. Synthesis and Characterization of Compound I-20-2

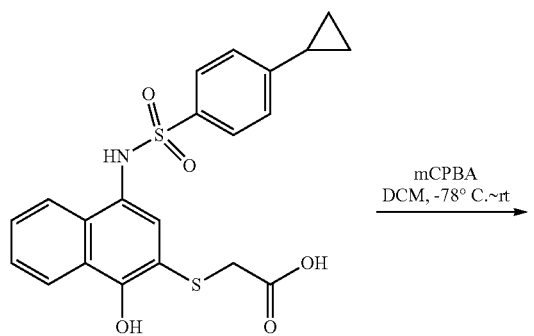

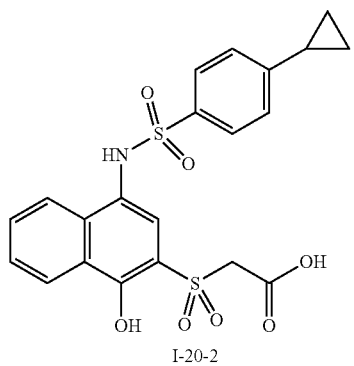

I-20-2

Compound I-20-2 (21 mg) was prepared according to the synthesis method of compounds I-20-1 and I-42.

The purified product I-20-2 was taken for structural characterization, LC-MS (ESI) m/z: 460 [MH]⁻.

Example 52. Synthesis and Characterization of Compound I-21-2

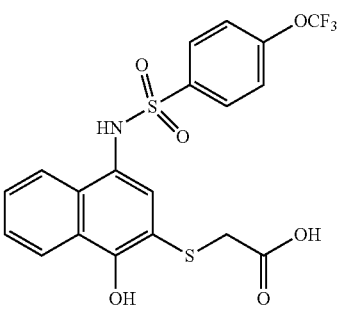

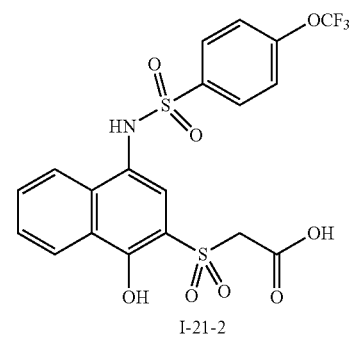

I-21-2

Compound I-21-2 (14 mg) was prepared according to the synthesis method of compounds I-21-1 and I-42.

The purified product I-21-2 was taken for structural characterization, LC-MS (ESI) m/z: 504 [MH]⁻.

Example 53. Synthesis and Characterization of Compound I-22-2

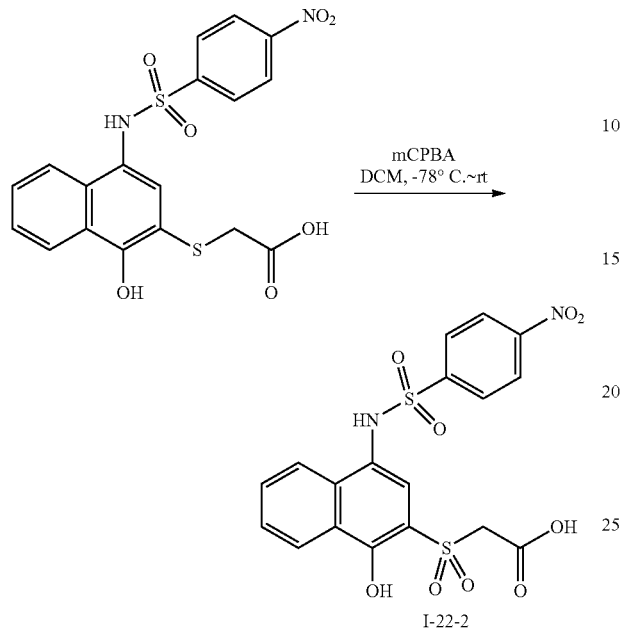

Compound I-22-2 (25 mg) was prepared according to the synthesis of compounds I-22-1 and I-42.

The purified product I-22-2 was taken for structural characterization, LC-MS (ESI) m/z: 465 [MH]⁻.

Example 54. Synthesis and Characterization of Compound I-23-2

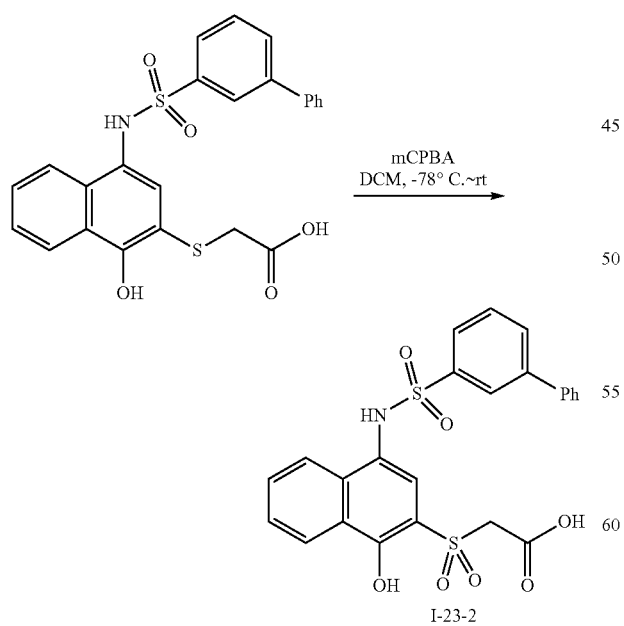

Compound I-23-2 (23 mg) was prepared according to the synthesis method of compounds I-23-1 and I-42.

The purified product I-23-2 was taken for structural characterization, LC-MS (ESI) m/z: 496 [MH]⁻.

Example 55. Synthesis and Characterization of Compound I-24-2

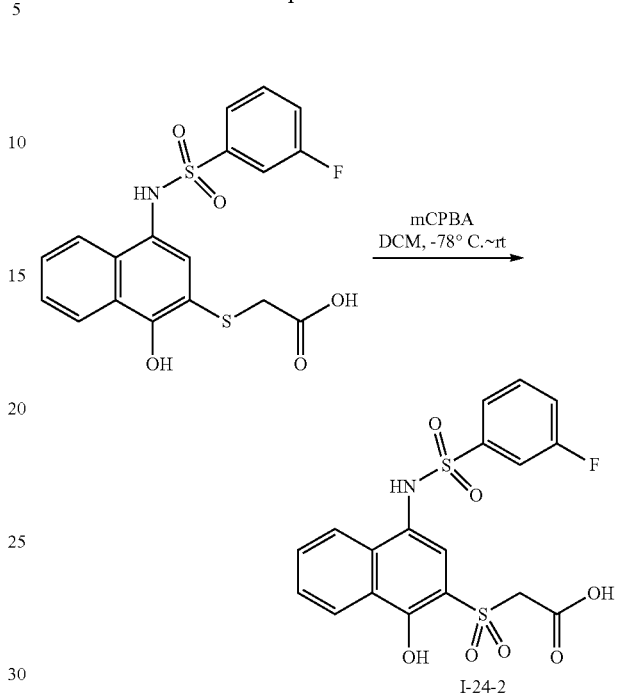

Compound I-24-2 (18 mg) was prepared according to the synthesis method of compounds I-24-1 and I-42.

The purified product I-24-2 was taken for structural characterization, LC-MS (ESI) m/z: 438 [MH]⁻.

Example 56. Synthesis and Characterization of Compound I-25-2

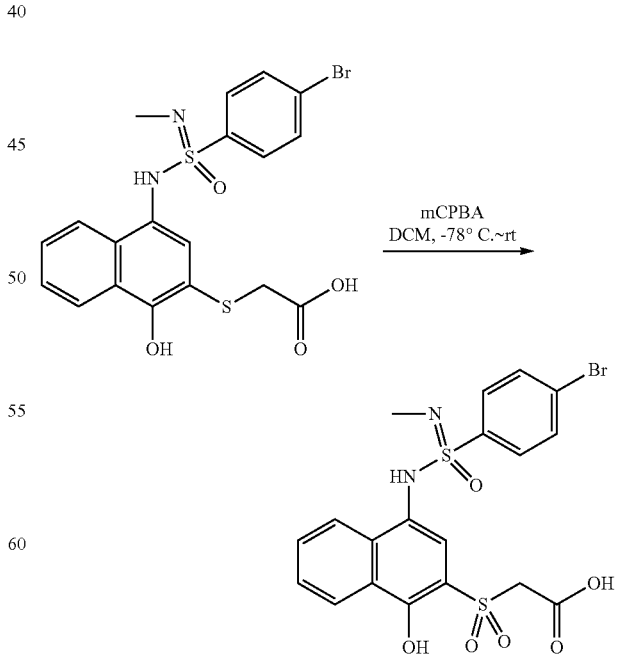

Compound I-25-2 (18 mg) was prepared according to the synthesis method of compounds I-25-1 and I-42.

The purified product I-25-2 was taken for structural characterization, LC-MS (ESI) m/z: 511, 513 [MH]⁻.

Example 57. Synthesis and Characterization of Compound I-35-2

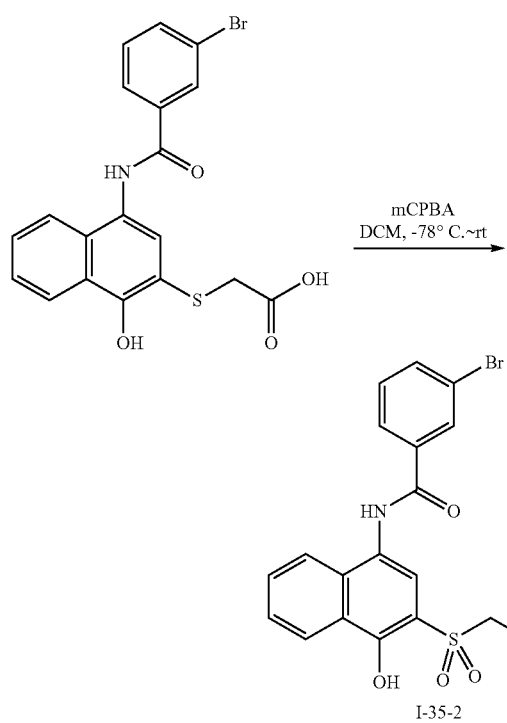

I-35-2

Compound I-35-2 (14 mg) was prepared according to the synthesis method of compounds I-35-1 and I-42.

The purified product I-35-2 was taken for structural characterization, ¹H-NMR (400 MHZ, DMSO-d6) δ 10.52 (s, 1H), 8.44 (d, J=8.0 Hz, 1H), 8.27-8.26 (m, 1H), 8.07 (d, J=8.0 Hz, 1H), 7.97 (d, 8.0 Hz, 1H), 7.85-7.83 (m, 1H), 7.77 (s, 1H), 7.76-7.67 (m, 1H), 7.54 (t, J=8.0 Hz, 1H), 4.64 (s, 2H). LC-MS (ESI) m/z: 462, 464 [MH]⁻.

Example 58. Synthesis and Characterization of Compound I-40-2

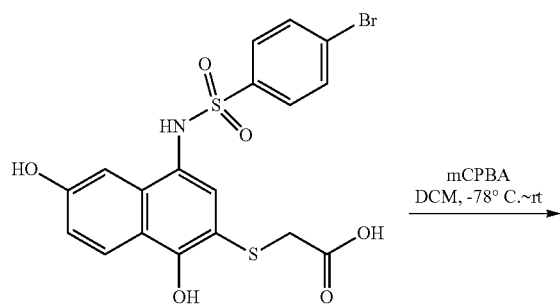

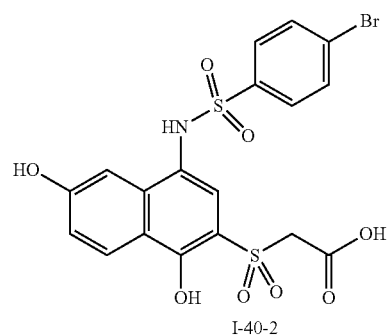

I-40-2

Compound I-40-2 (3 mg) was prepared according to the synthesis method of compounds I-40-1 and I-42.

The purified product I-40-2 was taken for structural characterization, LC-MS (ESI) m/z: 514, 516 [MH]⁻.

Example 59. Synthesis and Characterization of Compound I-41-2

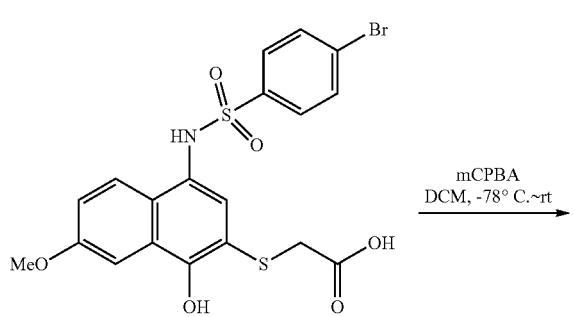

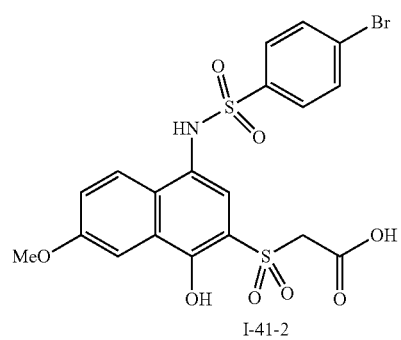

I-41-2

Compound I-41-2 (12 mg) was prepared according to the synthesis method of compounds I-41-1 and I-42.

The purified product I-41-2 was taken for structural characterization, LC-MS (ESI) m/z: 528, 530 [MH]⁻.

Example 60, Synthesis and Characterization of Compound I-43

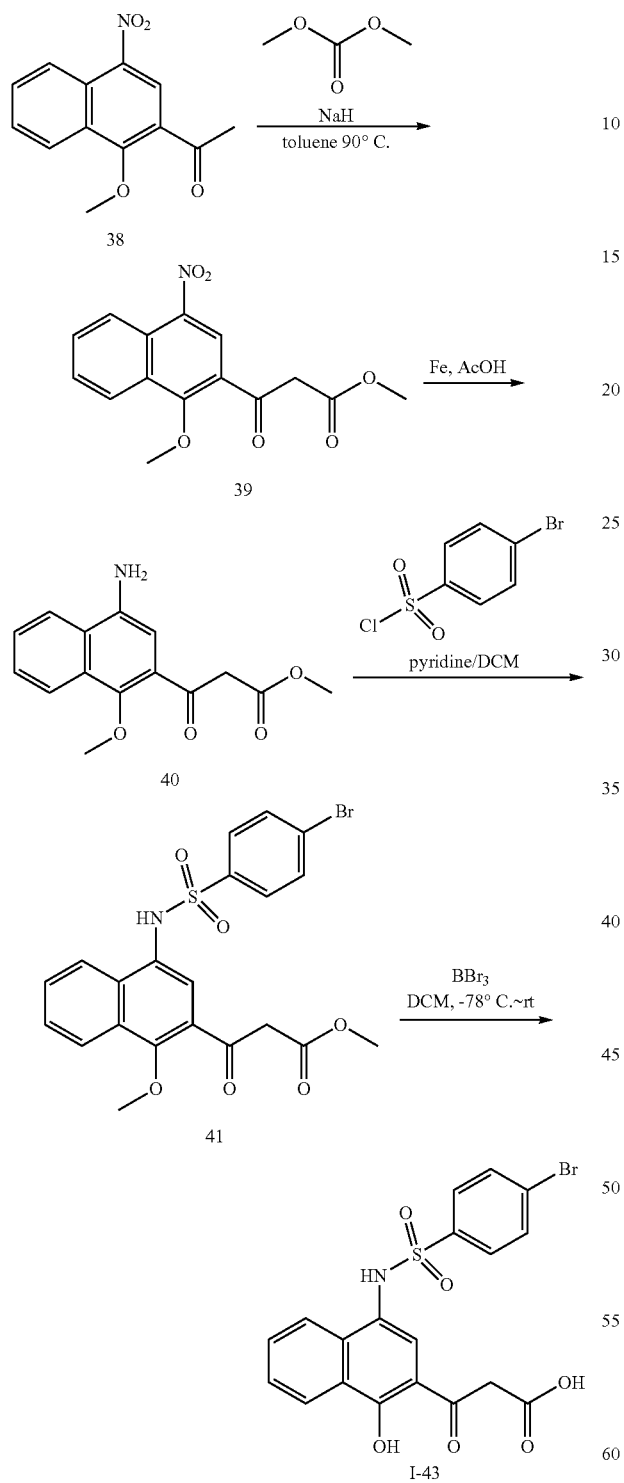

Compound I-43 was prepared from the known compound 38 according to the synthetic route as shown above.

The purified product I-43 was taken for structural characterization, LC-MS (ESI) m/z: 462, 464 [MH]⁻.

Example 61. Synthesis and Characterization of Compound I-44

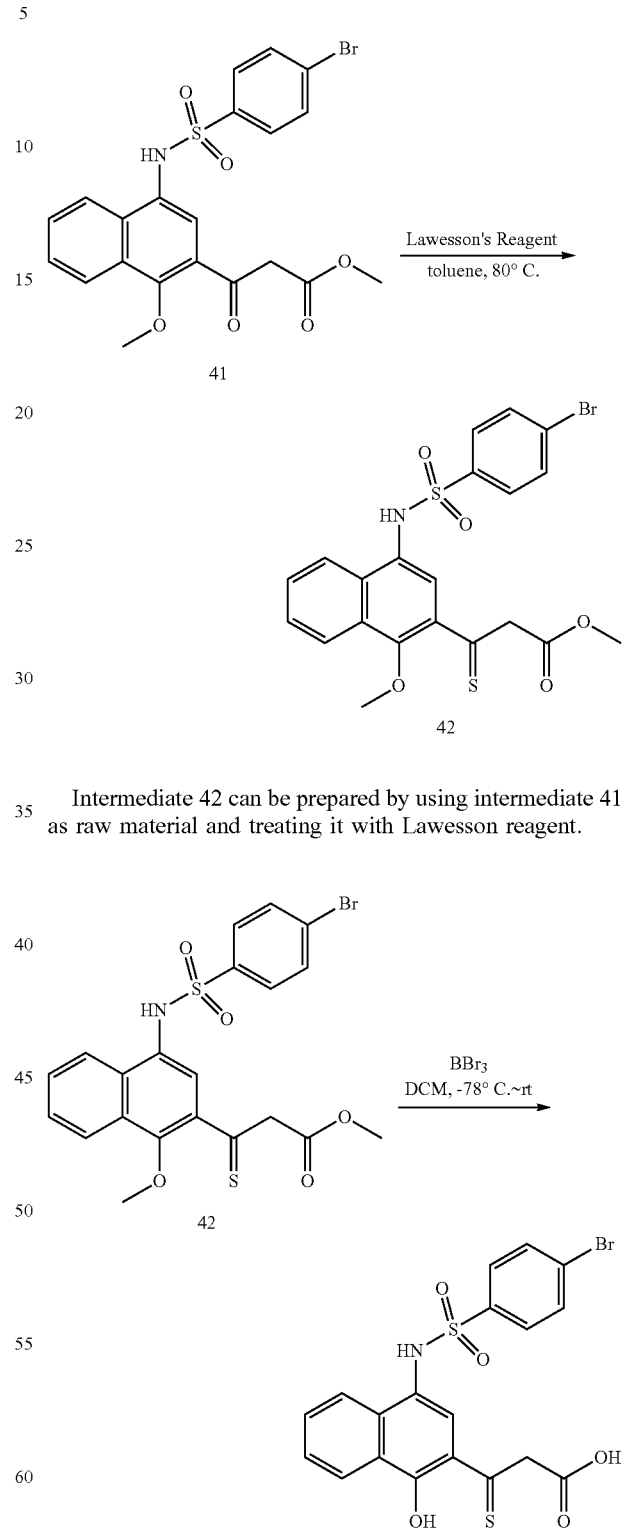

Intermediate 42 can be prepared by using intermediate 41 as raw material and treating it with Lawesson reagent.

Intermediate 42 can be treated with boron tribromide to remove the methyl to prepare compound I-44.

The purified product I-44 was taken for structural characterization: LC-MS (ESI) m/z: 478, 480 [MH]$^-$.

Test Example 1. Functional Test of Mitophagy Inducer

Group 1: Human embryonic kidney transformed cells HEK293Tmtkeima cells were treated with 0 μM, 1.25 μM, 2.5 μM, 5 μM and 10 μM CCCP respectively, and seeded in a 96-well black ELISA PLATE at 1.5*10$^5$ cells/ml, 100 μL per well. Compound I-2 was added after 25 hours, and 3 replicates were set. At 37° C., under 5% $CO_2$ incubation conditions, photographs were taken every few hours with biotek cytation 5 for a total of 20 hours, with the bright field as the focusing channel, and 9 images were taken per hole, and the images were processed using the instrument software. The resulting photographs are shown in FIG. 1.

As shown in FIG. 1, in cells treated with 0 μM CCCP, the color blocks with Compound I-2 administered are all lighter in color, indicating that the administration of Compound I-2 in cells with undamaged mitochondria fails to induce mitophagy, i.e., Compound I-2 is unable to induce autophagy in non-damaged mitochondria.

As shown in FIG. 1, in cells without CCCP and cells with CCCP (10 μM), compound I-2 was added respectively. The color block of cells with CCCP was darker, indicating that in cells with mitochondrial damage, high levels of mitophagy were observed with the administration of Compound I-2, i.e., Compound I-2 selectively induces autophagy in damaged mitochondria.

Group 2: Human embryonic kidney transformed cells HEK293Tmtkeima cells were seeded in a 96-well black ELISA PLATE at 1.5*10 cells/ml, 100 μL per well; compounds I-1~I-44 and UMI-77 were added after 25 hours, set up 3 replicates; under 37° C., 5% $CO_2$ culture conditions, use biotek every few hours Cytation 5 was used to take photos, a total of 20 hours of shooting. In another group of cells under the same conditions, human embryonic kidney-transformed cells HEK293Tmtkeima cells were seeded in a 96-well black enzyme plate at 1.5*10$^5$ cells/ml, 100 μl per well; after 24 hours, 5 uM or 10 uM CCCP (Carbonyl cyanide) was first added 3-chlorophenylhydrazone) to induce mitochondrial damage, then add I-1~I-44, UMI-77 1 hour later, set up 3 repetitions; under 37° C., 5% $CO_2$ culture conditions, pictures were taken every few hours with biotek cytation 5, photographs were taken for 20 hours. Another group of human embryonic kidney transformed cells HEK293Tmtkeima cells was seeded at 1.5*10$^5$ cells/ml in 96-well black ELISA PLATE at 100 μl per well under the same conditions, 24 hours later 5 uM or 10 uM CCCP (Carbonyl cyanide 3-chlorophenylhydrazone) was first added to induce mitochondrial damage, after 1 hour then add I-1 to I-44, UMI-77 and set up 3 replicates. At 37° C., under 5% $CO_2$ incubation conditions, pictures were taken every few hours with biotek cytation 5, photographs were taken for 20 hours, with the bright field as the focusing channel for both groups, and 9 images were taken per hole, and the images were processed using the instrument software. Some of the resulting photographs are shown in FIG. 2.

Figure 2:
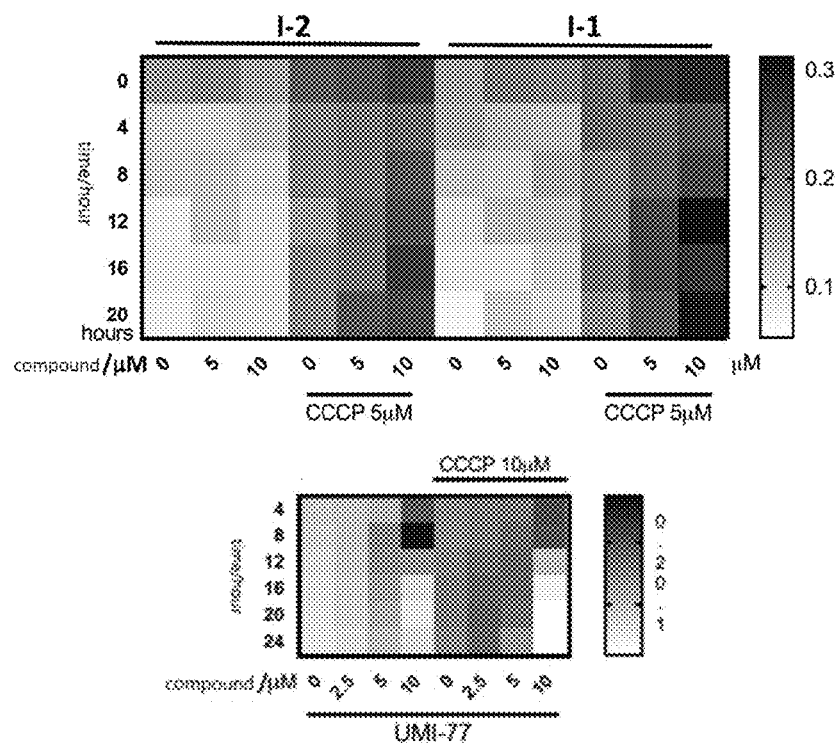
FIG. 2 is a graph showing the test results of the ability of UMI-77, I-2, and I-1 to selectively induce autophagy in damaged mitochondria in Test Example 1 of the present invention.

As shown in FIG. 2, in the human embryonic kidney transformed cell HEK293 Tmtkeima system, compounds I-1 and I-2 were added after treatment with 5 uM or 10 uM CCCP to induce mitochondrial damage. Compared with no treatment with CCCP, only the test compound was added, and the blocks are darker in color, it shows that compounds I-1 and I-2 are more likely to induce autophagy in damaged mitochondria. As for UMI-77, under the same conditions, the color blocks of damaged mitochondria and undamaged mitochondria are both darker, indicating that UMI-77 is unable to selectively induce autophagy in damaged mitochondria.

The results of the tests on the ability of other compounds to induce autophagy in damaged mitochondria are shown in Table 1:

TABLE 1

| Compound number | The ability of selection to induce autophagy in damaged mitochondria | Compound number | The ability of selection to induce autophagy in damaged mitochondria |
| --- | --- | --- | --- |
| I-1 | +++ | I-7-2 | + |
| I-2 | ++ | I-13-2 | ++ |
| I-3 | ++ | I-14-2 | ++ |
| I-4 | + | I-23-2 | ++ |
| I-5 | + | | |
| I-6 | + | | |
| I-7 | ++ | | |
| I-8 | +++ | | |
| I-13-1 | +++ | | |
| I-14-1 | ++ | | |
| I-15-1 | + | | |
| I-16-1 | ++ | | |
| I-17-1 | +++ | | |
| I-18-1 | + | | |
| I-19-1 | ++ | | |
| I-20-1 | ++ | | |
| I-21-1 | +++ | | |
| I-22-1 | + | | |
| I-23-1 | +++ | | |
| I-24-1 | + | | |
| I-25-1 | +++ | | |
| I-26 | ++ | | |
| I-27 | ++ | | |
| I-28 | + | | |
| I-29 | +++ | | |
| I-31 | + | | |
| I-33 | ++ | | |
| I-35-1 | + | | |
| I-36 | ++ | | |
| I-37 | ++ | | |
| I-42 | + | | |
| UMI-77 | NA | | |

"+++" indicates that the compound has a strong ability to selectively induce autophagy in damaged mitochondria (number of cells in which damaged mitophagy occurs/number of all cells >0.30), and "++" indicates that the compound has a moderate ability to selectively induce autophagy in damaged mitochondria (number of cells in which damaged mitophagy occurs/number of all cells in the range of 0.2 to 0.3), "+" indicates that the compound has a weak ability to selectively induce autophagy in damaged mitochondria (number of cells in which damaged mitophagy occurs/number of all cells in the range of 0.1 to 0.2), "NA" means that the compound was not detected with the ability to selectively induce autophagy in damaged mitochondria.
Note:
The HEK 293 Tmtkeima cells used in the experiment were based on the method in the literature [Cen, X. et al. Nat Commun11, 5731 (2020).], using lentiviral packaging technology to stably express mtkeima protein in HEK 293 T cells to obtain HEK 293 Tmtkeima cells. The CCCP used in the experiment was purchased from TargetMol (item number T7081).

Test Example 2, In Vitro Liver Microparticle Stability Test

Ketanserin was selected as the reference compound. The specific method is as follows:

Prepare 0.1M $K_3PO_4$ (pH 7.4) buffer and 3×NADPH stock solution (6 mM, 5 mg/mL), and preheat in a 37° C. water bath; configure the test compound and control compound spiking solution: 5 μL compound stock solution (10 nM) was added to 95 μL acetonitrile; Configuration of 1.5 μM spiking solution in microsomes (0.75 mg/mL): 1.5 μL of spiking solution and 18.75 μL of liver microparticles solution (20 mg/mL) were added to 479.75 μL of $K_3PO_4$ buffer; add 30 μL spiking solution in microsomes to the multi-well plate, and incubated at 37° C. for 5 minutes; add 15 µL NADPH stock solution to each well to start the reaction, and timing; the reaction was terminated by adding 150 µL of acetonitrile solution containing IS at 0 min, 5 min, 15 min, 30 min and 45 min, respectively; shake for 10 min and then centrifuge at 6000 rpm for 15 min; take 80 µL of the supernatant from each well for LC/MS detection and calculate T1/2. The test results are shown in FIG. 3.

Figure 3:
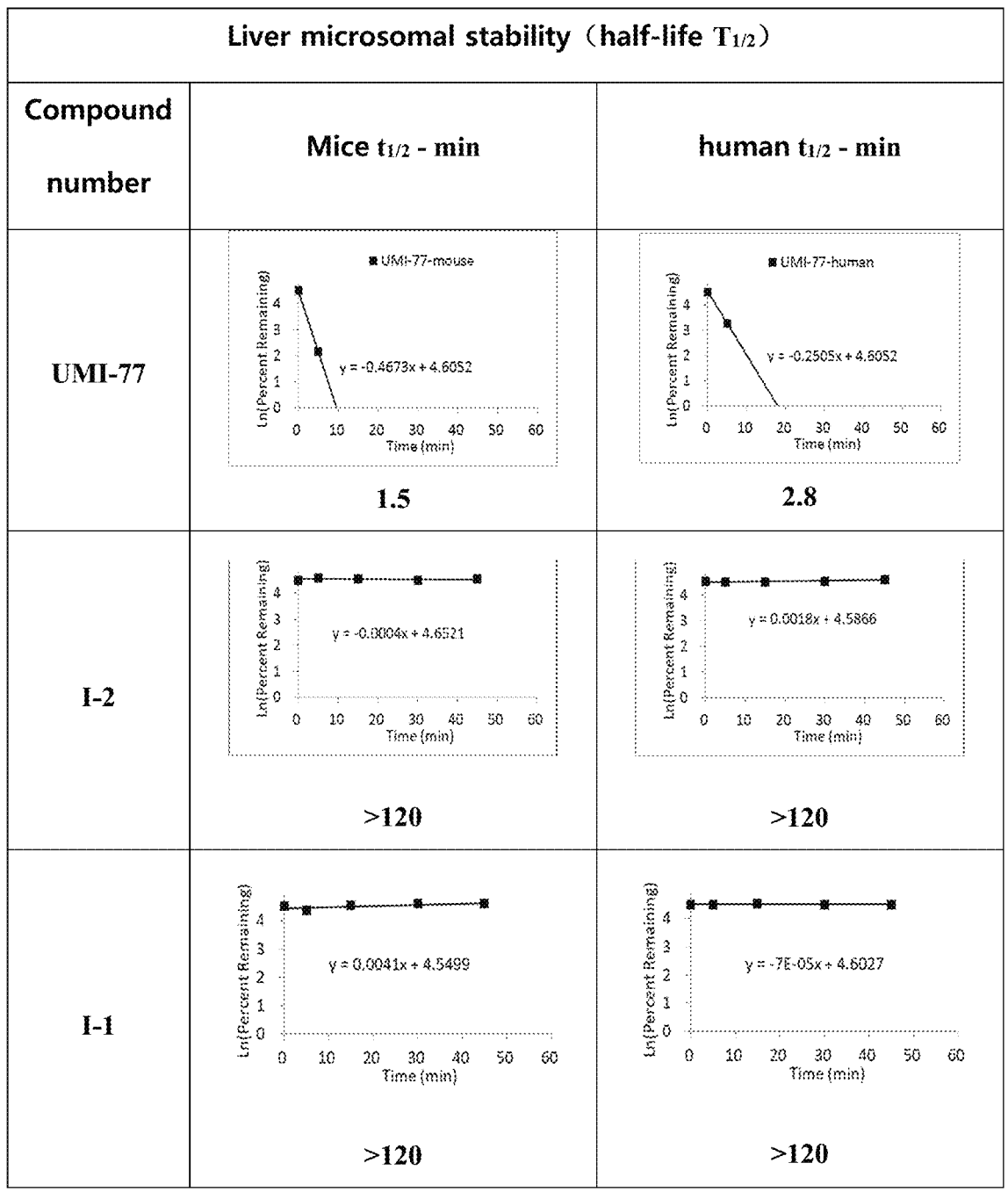
FIG. 3 is a graph showing the in vitro liver microsome stability test results of compounds UMI-77, I-2, and I-1 in Test Example 2 of the present invention.

FIG. 3 shows the elimination of compounds in the in vitro mouse or human liver microsomal environment, measured as the elimination half-life T 1/2. The in vitro liver microsomal stability experiment of UMI-77 shows that UMI-77 is unstable in the liver microsomal environment and will be rapidly eliminated; and compounds I-1 and I-2 show superior liver microsomal stability.

Note: The mouse and human liver microsomes used in the experiments were purchased from Xenotech.

Test Example 3. In Vitro Plasma Stability Test

Procaine was selected as the reference compound. The specific method is as follows:

Dissolve an appropriate amount of the DMSO stock solution of the test compound and the control compound in 4 mL of plasma so that the concentration is 200 g/mL and the DMSO content does not exceed 0.1%. Incubated in a water bath at 37° C. for 0, 5, 15 and 30 minutes and 1, 2, 4, 6, 10, 24 and 48 hours. Take 200 µL and add 3 times the volume of chromatography grade acetonitrile to precipitate the protein. Vortex shaking for 5 minutes, centrifuge, take 200 µL of the supernatant, HPLC injection and analysis. The liquid phase conditions are the same as before. The test results are shown in FIG. 4.

Figure 4:
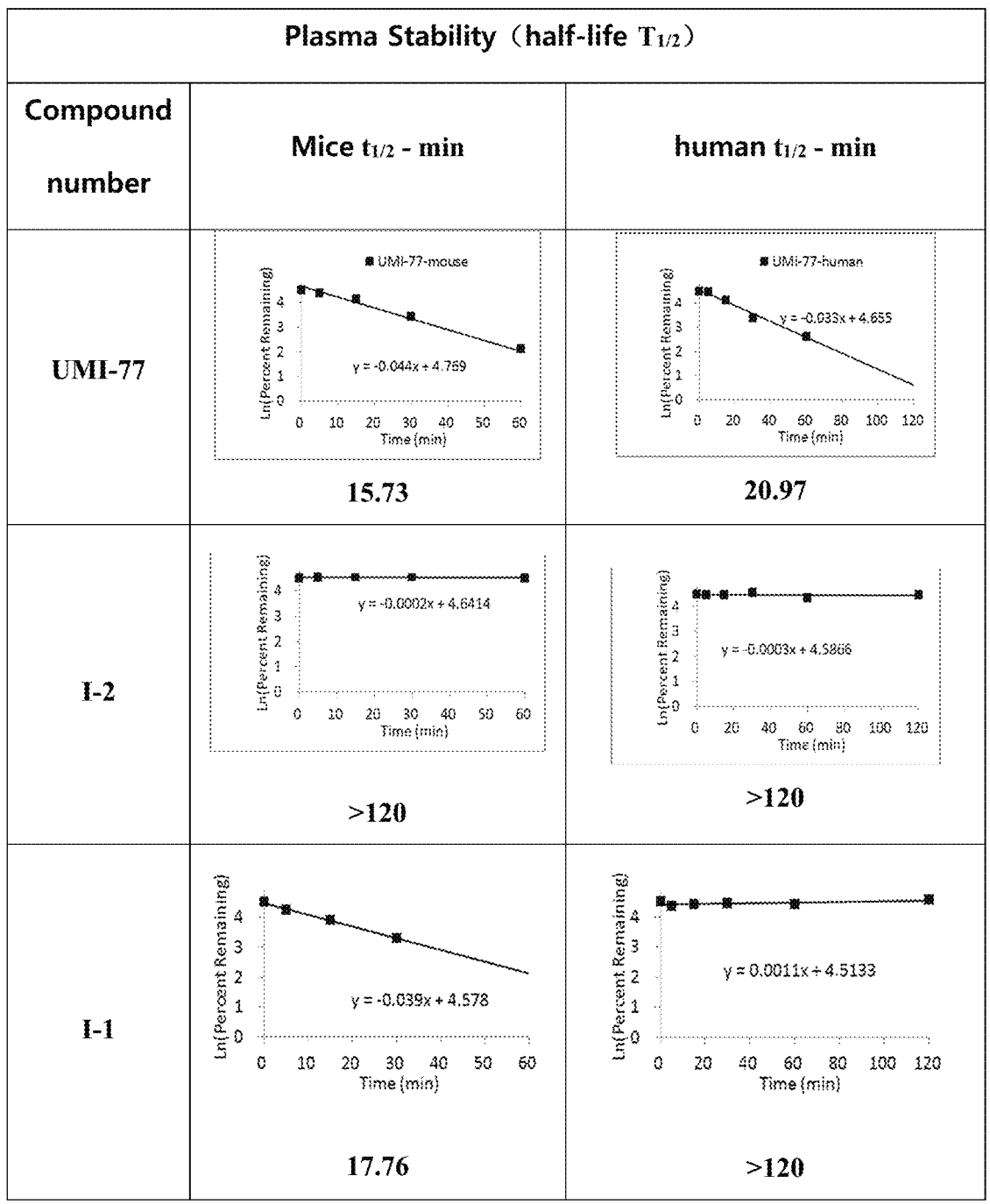
FIG. 4 is a graph showing the in vitro plasma stability test results of compounds UMI-77, I-2, and I-1 in Test Example 3 of the present invention.

In FIG. 4, the half-life of UMI-77 is short, indicating that UMI-77 is unstable in the plasma environment and will be rapidly eliminated, while compounds I-1 and I-2 show superior plasma stability.

Test Example 4, Mouse or Rat Pharmacokinetics (PK) Test

Take experimental mice and apply an appropriate amount of the test compound to them according to the dosage and administration route shown in the figure. Three experimental mice were selected for three parallel experiments for each compound and each administration method. Numbers 101, 102 and 103 were in the same group, 201, 202 and 203 were in one group, and 301, 302 and 303 were in one group.

At the corresponding time point, take 10 µL of rat plasma sample into a centrifuge tube, add 100 µL of methanol: acetonitrile (1:1, v/v), perform voltammetry for 1 min, centrifuged (14000 rpm) for 5 min, and take 50 µL of the supernatant, mixed with water in equal volumes, mixed uniformly by voltammetry and then analyzed.

The results of pharmacokinetic tests in mice are shown in Table 2.

TABLE 2

| | compound | UM I-77 | I-1 | I-2 |
|---|---|---|---|---|
| | PK dose-mg/kg | 1 for IV; 10 for PO; 3 for IP | | |
| IV intravenous injection | Half-life $t_{1/2}$ - hr | NA | 1.25 | 0.98 |
| | Eliminate Cl-mL/min/kg | 130.92 | 24.9 | 39.34 |
| | Peak blood concentration $C_{max}$ - ng/mL | 313.97 | 832.02 | 947.13 |

TABLE 2-continued

Figure 5:
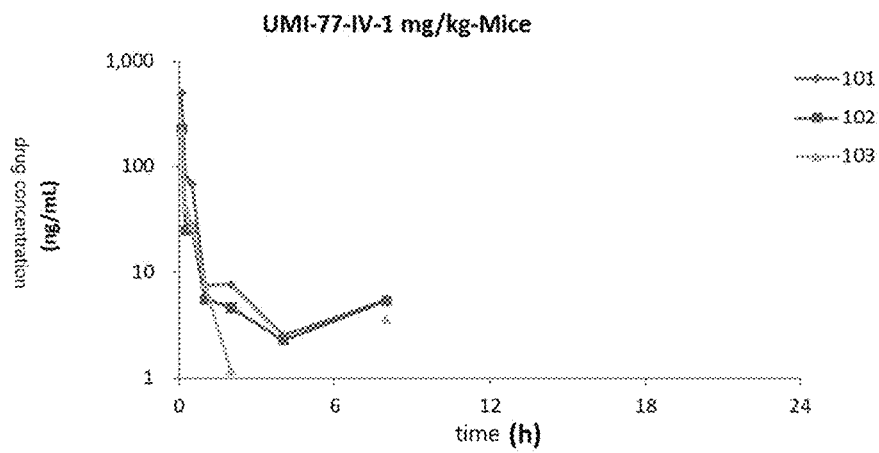
FIG. 5 is a drug-time curve chart of compound UMI-77 administered via IV in Test Example 4 of the present invention.
Figure 6:
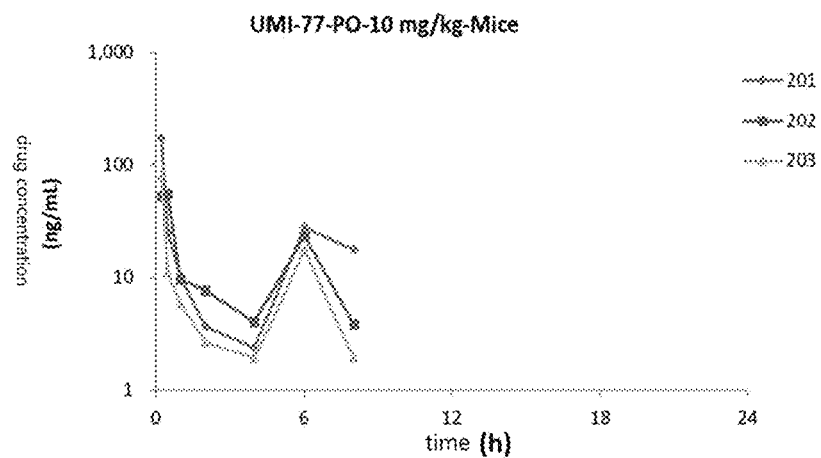
FIG. 6 is a drug-time curve chart of compound UMI-77 administered via PO in Test Example 4 of the present invention.
Figure 7:
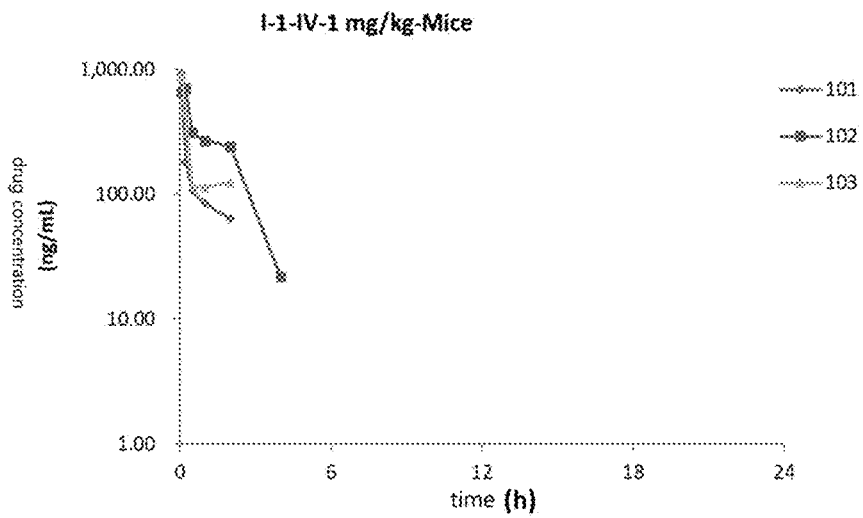
FIG. 7 is a drug-time curve chart of Compound I-1 administered to standard mice via IV in Test Example 4 of the present invention.
Figure 8:
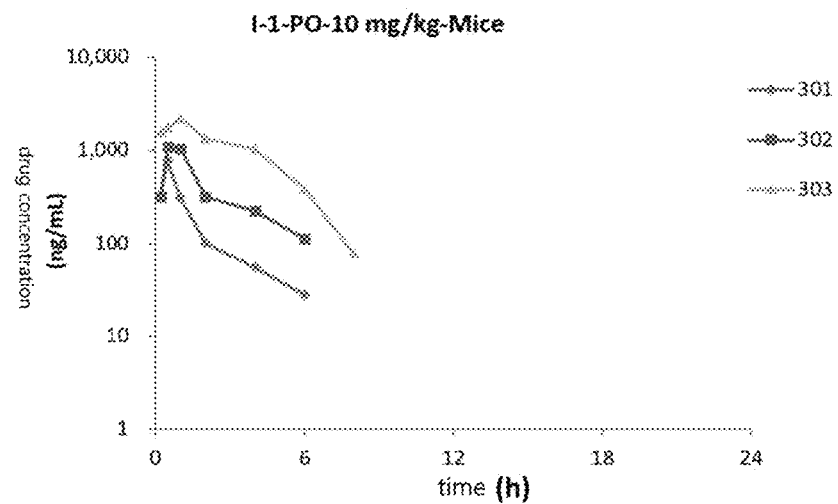
FIG. 8 is a drug-time curve chart of Compound I-1 administered to standard mice via PO in Test Example 4 of the present invention.
Figure 9:
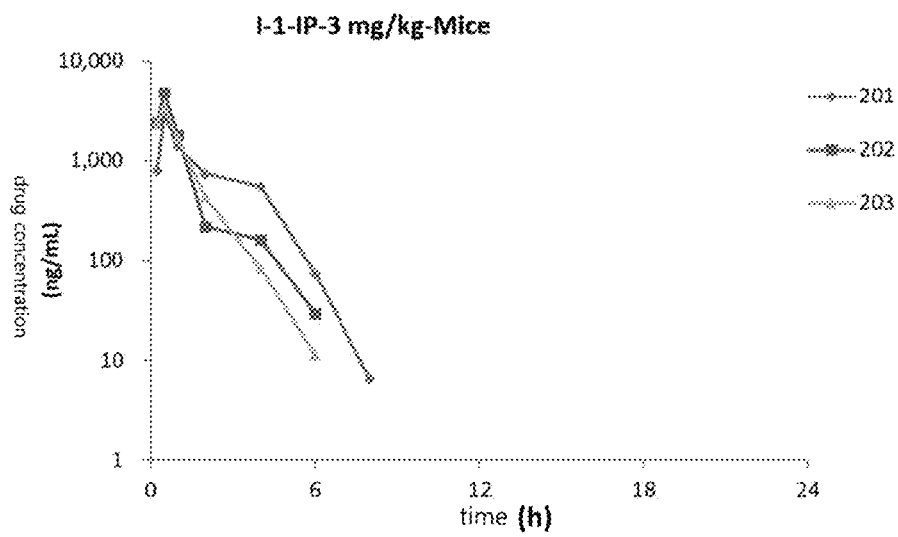
FIG. 9 is a drug-time curve chart of Compound I-1 administered to standard mice via IP in Test Example 4 of the present invention.
Figure 10:
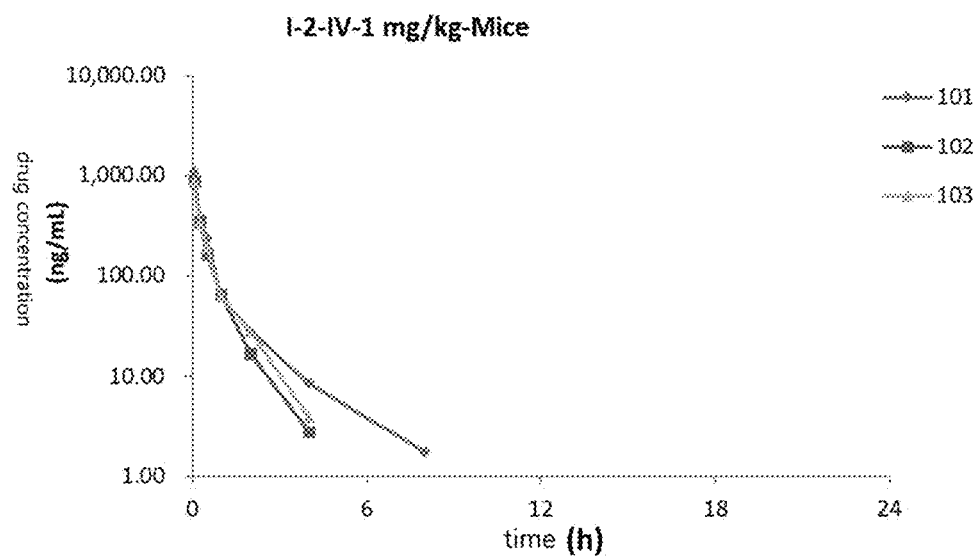
FIG. 10 is a drug-time curve chart of Compound I-2 administered to standard mice via IV in Test Example 4 of the present invention.
Figure 11:
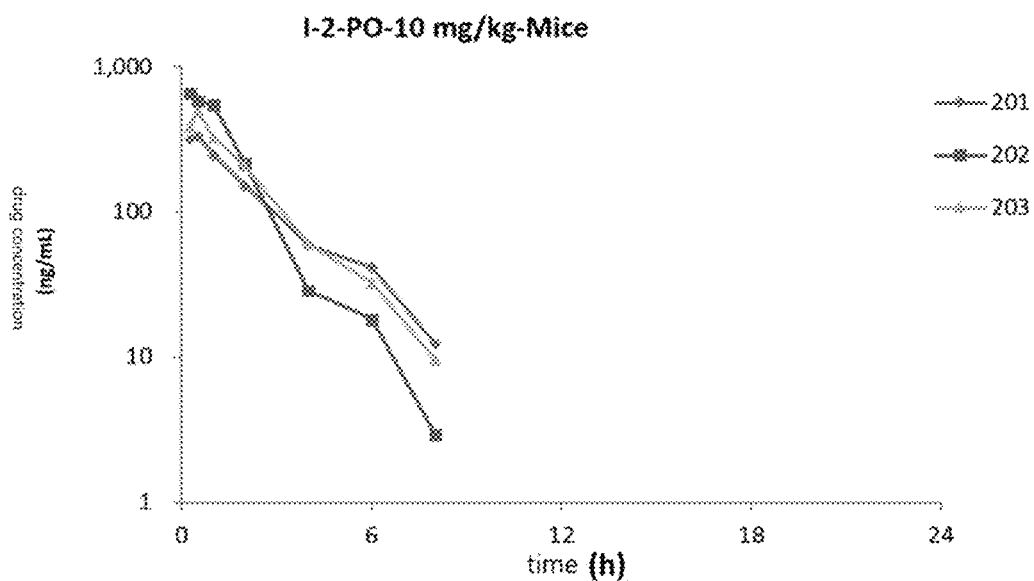
FIG. 11 is a drug-time curve chart of Compound I-2 administered to standard mice via PO in Test Example 4 of the present invention.

| | compound | UM I-77 | I-1 | I-2 |
|---|---|---|---|---|
| | $AUC_{inf}$ - hr *ng/mL | 140.34 | 714.41 | 429.41 |
| | Steady state apparent volume of distribution $V_{ss}$ - L/kg | 18.40 | 2.3 | 1.39 |
| | Drug-time curve | See FIG. 5 | See FIG. 7 | See FIG. 10 |
| PO Oral gavage | Half-life $t_{1/2}$ - hr | NA | 1.96 | 1.37 |
| | Eliminate Cl-mL/min/kg | / | / | / |
| | Peak blood concentration $C_{max}$ - ng/mL | 102.45 | 1345.78 | 494.74 |
| | $AUC_{inf}$ - hr *ng/mL | 162.29 | 3796.07 | 1045.05 |
| | Bioavailability F-% | 8.64 | 60.41 | 24.12 |
| | Drug-time curve | See FIG. 6 | See FIG. 8 | See FIG. 11 |
| IP intraperitoneal injection | Half-life $t_{1/2}$ - hr | / | 0.79 | / |
| | Eliminate Cl-mL/min/kg | / | / | / |
| | Peak blood concentration C max -ng/mL | / | 3744.89 | / |
| | $AUC_{inf}$ - hr *ng/mL | / | 4415.08 | / |
| | Bioavailability F-% | / | 247.06 | / |
| | Drug-time curve | / | See FIG. 9 | / |

The results of the pharmacokinetic test in rats (administration I-1) are shown in Table 3.

TABLE 3

Figure 12:
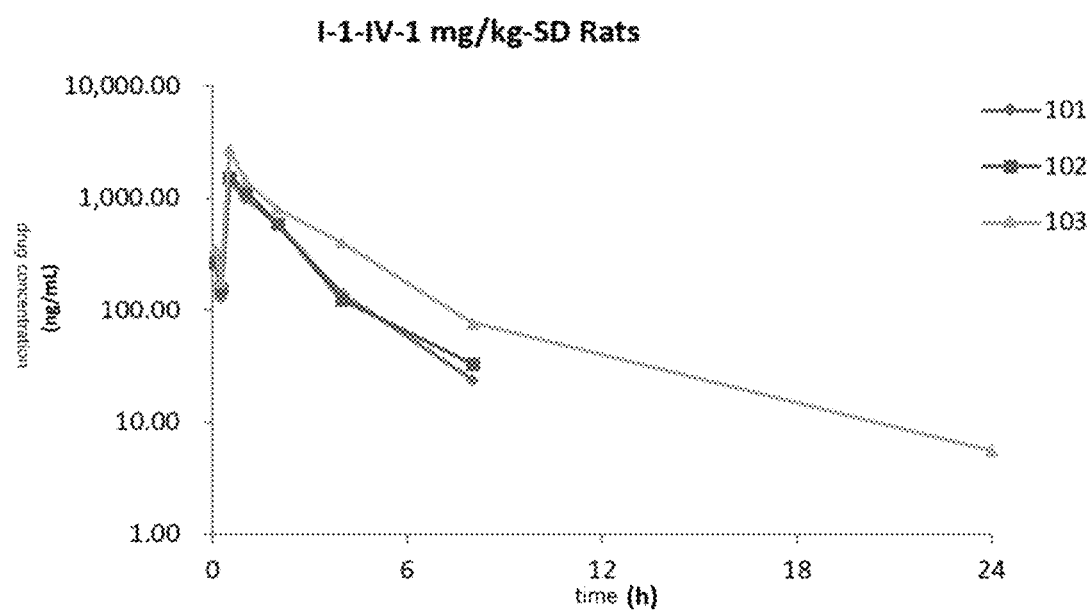
FIG. 12 is a drug-time curve chart of Compound I-1 administered to SD rats via IV in Test Example 4 of the present invention.
Figure 13:
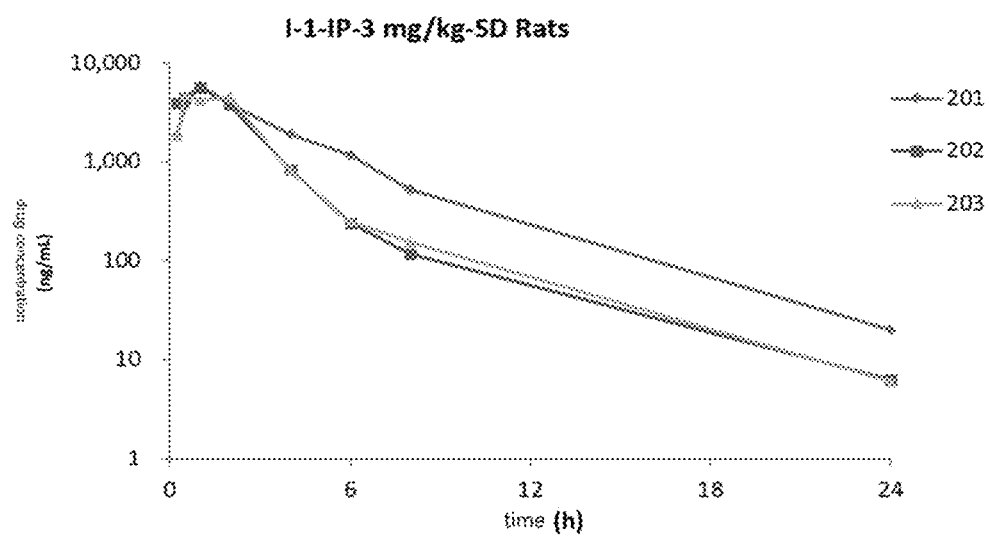
FIG. 13 is a drug-time curve chart of Compound I-1 administered to SD rats via IP in Test Example 4 of the present invention.
Figure 14:
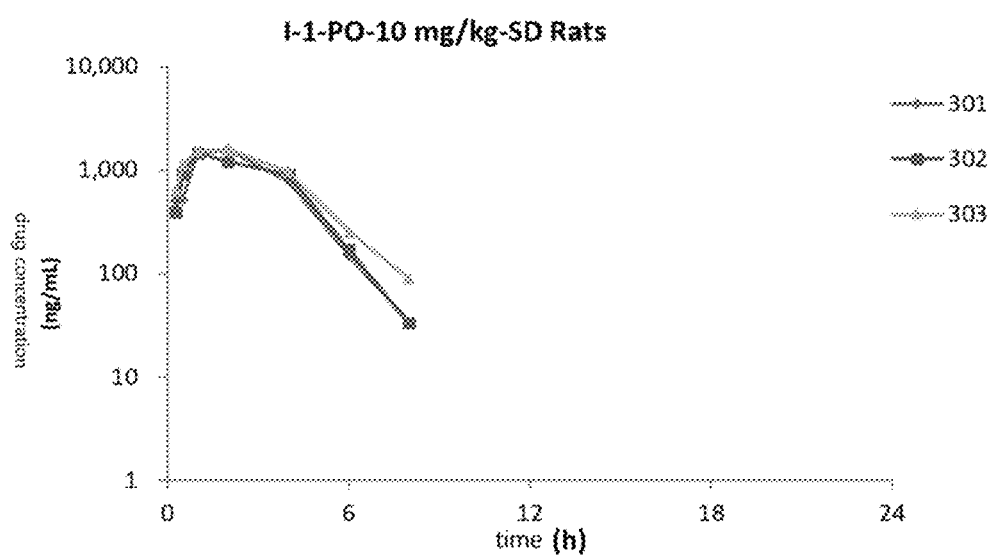
FIG. 14 is a drug-time curve chart of Compound I-1 administered to SD rats via PO in Test Example 4 of the present invention.

| | IV intravenous injection/ (1 mg/kg) | IP intraperitoneal injection (3 mg/kg) | PO oral gavage (10 mg/kg) |
|---|---|---|---|
| Half-life $t_{1/2}$ - hr | 1.93 | 3.34 | 0.96 |
| Eliminate Cl-mL/min/kg | 4.91 | / | / |
| Peak blood concentration $C_{max}$ - ng/mL | 1895.11 | 5439.27 | 1549.52 |
| $AUC_{inf}$ - hr *ng/mL | 3722.68 | 18275.52 | 6070.32 |
| Steady state apparent volume of distribution $V_{ss}$ - L/kg | 0.63 | / | / |
| Bioavailability F-% | / | 165.15 | 16.29 |
| Drug-time curve | See FIG. 12 | See FIG. 13 | See FIG. 14 |

In Table 2 above, "NA" means that it cannot be measured, and "/" means that the item has not been measured.

The test results shows that UMI-77 is rapidly cleared in the mouse PK experiment, and the blood concentration can no longer be measured soon; while compounds I-1 and I-2 show good PK properties, and I-1 also shows good PK properties in the rat PK experiment.

Note: The mice used in the PK experiment are ICR mice of SPF, purchased from Sino-British SIPPR Lab Animal Ltd, Shanghai, China. The rats used in the PK experiments were SD rats of SPF, purchased from Sino-British SIPPR Lab Animal Ltd, Shanghai, China.

Those of ordinary skill in the art can understand that the above-mentioned embodiments are specific examples for implementing the present invention, and in practical applications, various changes can be made in form and details without departing from the spirit and scope of the present invention.

The invention claimed is:

1. A compound having a structure represented by Formula (I) or a pharmaceutically acceptable salt, stereoisomer, solvate or prodrug thereof,

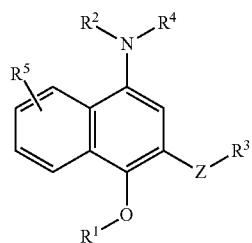

wherein:

Z is

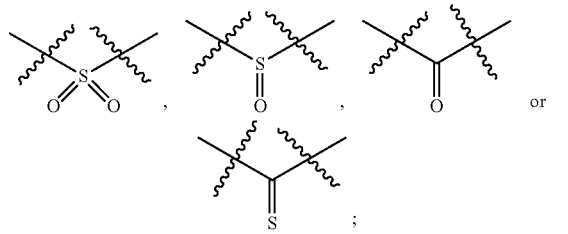

$R^1$ is hydrogen or $C_{1\sim6}$ alkyl;

$R^2$ is hydrogen, $C_{1\sim6}$ alkyl, three to six-membered cycloalkyl, three to six-membered epoxyalkyl, phenyl or $C_{1\sim6}$ alkyl substituted phenyl;

$R^3$ is

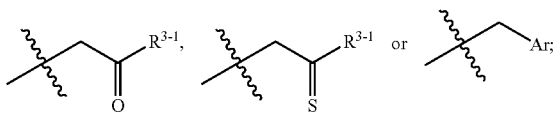

wherein $R^{3-1}$ is hydrogen, hydroxyl, $C_{1\sim6}$ alkyl, $C_{1\sim6}$ alkoxy, three to six-membered cycloalkyl, three to six-membered epoxyalkyl, amino, $C_{1\sim6}$ amido, —$CH_2C(O)R^{3-2}$, —$CH_2C(O)OR^{3-2}$ or —$CH_2C(O)N(R^{3-2}R^{3-2a})$, $R^{3-2}$ and $R^{3-2a}$ are each independently hydrogen, $C_{1\sim6}$ alkyl or three to six-membered cycloalkyl, Ar is phenyl, naphthyl, 5- or 6-membered monocyclic heteroaryl, 8 to 10-membered fused bicyclic heteroaryl, phenyl with at least one hydrogen atom substituted by $R^{3-3}$, naphthyl with at least one hydrogen atom substituted by $R^{3-3}$, 5- or 6-membered monocyclic heteroaryl with at least one hydrogen atom substituted by $R^{3-3}$ or 8 to 10-membered fused bicyclic heteroaryl with at least one hydrogen atom substituted by $R^{3-3}$, the $R^{3-3}$ is hydrogen, halogen, $C_{1\sim6}$ alkyl, three to six-membered cycloalkyl, hydroxyl, $C_{1\sim6}$ alkoxy, three to six-membered epoxyalkyl, $C_{1\sim6}$ haloalkyl, $C_{2\sim6}$ alkenyl, $C_{2\sim6}$ alkynyl, —$N(R^{3-3a}R^{3-3b})$ or phenyl, $R^{3-3a}$ and $R^{3-3b}$ are each independently hydrogen, $C_{1\sim6}$ alkyl or three to six-membered cycloalkyl;

$R^4$ is

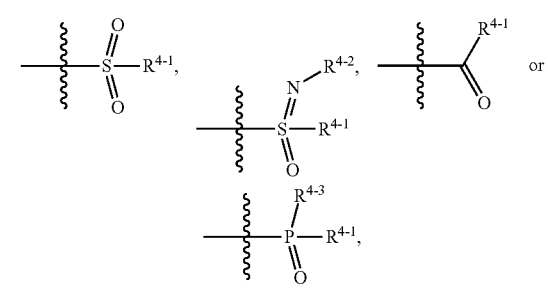

wherein $R^{4-1}$ is phenyl, naphthyl, phenyl with at least one hydrogen atom substituted by $R^{4-11}$, 5- or 6-membered monocyclic heteroaryl, 5- or 6-membered monocyclic heteroaryl with at least one hydrogen atom substituted by $R^{4-11}$ or 8 to 10-membered fused bicyclic heteroaryl, or 8- to 10-membered fused bicyclic heteroaryl with at least one hydrogen atom substituted by $R^{4-11}$, and the $R^{4-11}$ is hydrogen, halogen, nitro, nitrile group, hydroxyl, $C_{1\sim6}$ alkyl, three to six-membered cycloalkyl, $C_{1\sim6}$ alkoxy, —$N(R^{4-1a}R^{4-1b})$, phenyl, $C_{1\sim6}$ haloalkyl, $C_{1\sim6}$ haloalkoxy, —$C(O)OR^{4-12}$, —$C(O)R^{4-12}$, —$C(O)N(R^{4-1a}R^{4-1b})$, —$S(O)_2R^{4-12}$, —$S(O)R^{4-12}$, —$OC(O)R^{4-12}$, —$OC(O)OR^{4-12}$ or

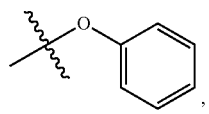 [SMILES: *Oc1ccccc1]

$R^{4-12}$, $R^{4-1a}$ and $R^{4-1b}$ are each independently hydrogen, $C_{1\sim6}$ alkyl, three to six-membered cycloalkyl, $C_{2\sim6}$ alkenyl, $C_{2\sim6}$ alkynyl, $C_{1\sim6}$ alkyl with at least one hydrogen substituted by halogen, $C_{2\sim6}$ alkenyl with at least one hydrogen substituted by halogen, three to six-membered cycloalkyl with at least one hydrogen substituted by halogen, or $C_{2\sim6}$ alkynyl with at least one hydrogen substituted by halogen, and $R^{4-1a}$ and $R^{4-1b}$ can be bonded to each other to form a ring, $R^{4-2}$ is hydrogen, $C_{1\sim6}$ alkyl or three to six-membered cycloalkyl, or when $R^2$ is $C_{1\sim6}$ alkyl, $R^{4-2}$ and $R^2$ are bonded to form a 4~8 membered ring, $R^{4-3}$ is hydrogen, $C_{1\sim6}$ alkyl or $C_{1\sim6}$ alkoxy; and the number of $R^5$ is 0~5, and when the number of $R^5$ is not 0, each $R^5$ is independently selected from halogen, nitro, nitrile group, —$N^+(R^{5-1})_3$, $C_{1\sim6}$ haloalkyl, —$C(O)OR^{5-1}$, —$C(O)R^{5-1}$, —$C(O)N(R^{5-1}R^{5-1a})$, —$S(O)_2R^{5-1}$, —$S(O)R^{5-1}$, —$S(O)_2N(R^{5-1}R^{5-1a})$, —$S(O)N(R^{5-1}R^{5-1a})$, —$N=C(R^{5-1}R^{5-1a})$, hydroxyl, $C_{1\sim6}$ alkyl, phenyl, phenyl with at least one hydrogen substituted by $R^{5-1}$, $C_{1\sim6}$ alkoxy, —$N(R^{5-1}R^{5-1a})$, —$N(R^{5-1})C(O)R^{5-1a}$, —$N(R^{5-1})C(O)OR^{5-1a}$, —$N(R^{5-1})C(O)N(R^{5-1a}R^{5-1b})$, —$OC(O)R^{5-1}$, —$OC(O)OR^{5-1}$, —$OC(O)N(R^{5-1}R^{5-1a})$ and —$SR^{5-1}$, wherein $R^{5-1}$, $R^{5-1a}$ and $R^{5-1b}$ are each independently hydrogen, $C_{1\sim 6}$ alkyl, $C_{2\sim 6}$ alkenyl, $C_{2\sim 6}$ alkynyl, $C_{1\sim 6}$ alkyl with at least one hydrogen substituted by halogen, $C_{2\sim 6}$ alkenyl with at least one hydrogen substituted by halogen, or $C_{2\sim 6}$ alkynyl with at least one hydrogen substituted by halogen, with the proviso that:

the compound of Formula (I) is not

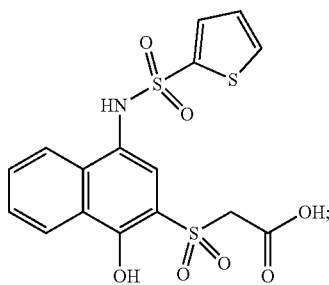 [SMILES: O=C(O)CS(=O)(=O)c1cc(NS(=O)(=O)c2cccs2)c2ccccc2c1O]

and when $R^1$ and $R^2$ are hydrogen, $R^4$ is

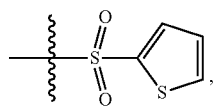 [SMILES: *S(=O)(=O)c1cccs1]

Z is

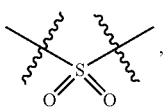 [SMILES: *S(*)(=O)=O]

and the number of $R^5$ is 0, then $R^3$ is not —CH$_2$COOCH$_2$CH$_3$.

2. The compound or a pharmaceutically acceptable salt, stereoisomer, solvate or prodrug thereof of claim 1, wherein Z is

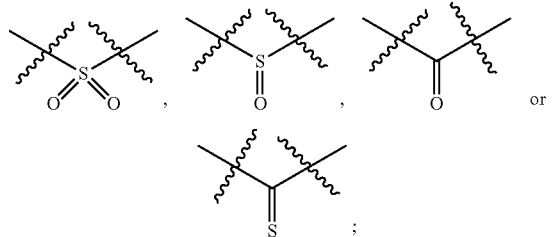

$R^1$ is hydrogen or $C_{1\sim 4}$ alkyl;

$R^2$ is hydrogen, $C_{1\sim 4}$ alkyl, three to six-membered cycloalkyl or four to six-membered epoxyalkyl;

$R^3$ is

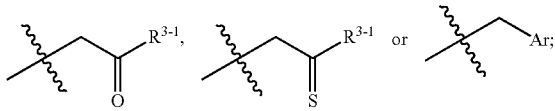

wherein, $R^{3-1}$ is hydrogen, hydroxyl, $C_{1\sim 4}$ alkyl, $C_{1\sim 4}$ alkoxy or —N($R^{3-2}R^{3-2a}$), $R^{3-2}$ and $R^{3-2a}$ are each independently hydrogen or $C_{1\sim 4}$ alkyl, Ar is phenyl, 5- or 6-membered monocyclic heteroaryl, or a 5- or 6-membered monocyclic heteroaryl with at least one hydrogen atom substituted by $R^{3-3}$, and the $R^{3-3}$ is hydrogen, halogen, $C_{1\sim 4}$ alkyl, hydroxyl, $C_{1\sim 4}$ alkoxy, $C_{1\sim 4}$ haloalkyl or —N($R^{3-3a}R^{3-3b}$), $R^{3-3a}$ and $R^{3-3b}$ are each independently hydrogen or $C_{1\sim 4}$ alkyl;

$R^4$ is

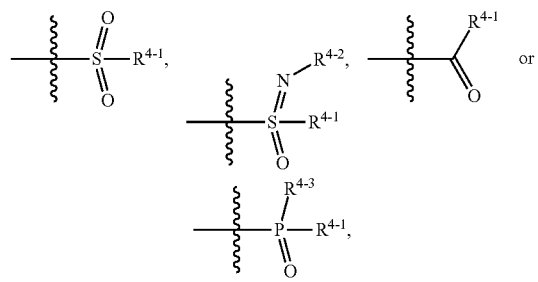

wherein, $R^{4-1}$ is phenyl, phenyl with at least one hydrogen atom substituted by $R^{4-11}$, 5- or 6-membered monocyclic heteroaryl, or 5- or 6-membered monocyclic heteroaryl with at least one hydrogen atom substituted by $R^{4-11}$, and the $R^{4-11}$ is hydrogen, halogen, nitro, $C_{1\sim 4}$ alkyl, three to six-membered cycloalkyl, $C_{1\sim 4}$ alkoxy, —N($R^{4-1a}R^{4-1b}$), phenyl, $C_{1\sim 4}$ haloalkyl, $C_{1\sim 4}$ haloalkoxy or

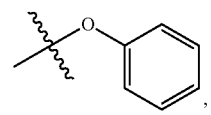

$R^{4-1a}$ and $R^{4-1b}$ are each independently hydrogen, $C_{1\sim 4}$ alkyl or three to six membered cycloalkyl, and $R^{4-1a}$ and $R^{4-1b}$ can be bonded to each other to form a ring, $R^{4-2}$ is $C_{1\sim 4}$ alkyl, three- to six-membered cycloalkyl, or when $R^2$ is $C_{1\sim 4}$ alkyl, $R^{4-2}$ and $R^2$ are bonded to form a 4~8 membered ring, $R^{4-3}$ is $C_{1\sim 4}$ alkyl or $C_{1\sim 4}$ alkoxy; and when the number of $R^5$ is not 0, each $R^5$ is independently selected from halogen, nitro, nitrile group, —N$^+$($R^{5-1}$)$_3$, $C_{1\sim 4}$ haloalkyl, —C(O)O$R^{5-1}$, —C(O)$R^{5-1}$, —C(O)N($R^{5-1}R^{5-1a}$), —S(O)$_2R^{5-1}$, —S(O)$R^{5-1}$, —N═C($R^{5-1}R^{5-1a}$), hydroxyl, $C_{1\sim 4}$ alkyl, phenyl, phenyl with at least one hydrogen substituted by $R^{5-1}$, $C_{1\sim 4}$ alkoxy, —N($R^{5-1}R^{5-1a}$), —N($R^{5-1}$) C(O)$R^{5-1a}$ and —OC(O)$R^{5-1}$, wherein $R^{5-1}$, $R^{5-1a}$ and $R^{5-1b}$ are each independently hydrogen, $C_{1-4}$ alkyl, and $C_{1-4}$ alkyl with at least one hydrogen substituted by halogen, with the proviso that:

the compound of Formula (I) is not

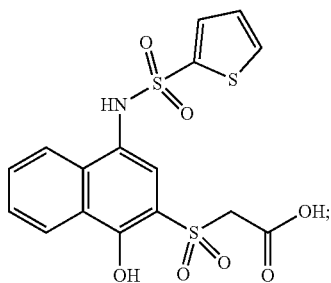 [SMILES: O=C(O)CS(=O)(=O)c1cc(NS(=O)(=O)c2cccs2)c2ccccc2c1O]

and when $R^1$ and $R^2$ are hydrogen, $R^4$ is

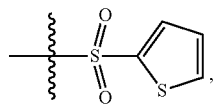 [SMILES: *S(=O)(=O)c1cccs1]

Z is

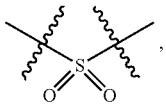

and the number of $R^5$ is 0, then $R^3$ is not —$CH_2COOCH_2CH_3$.

3. The compound or a pharmaceutically acceptable salt, stereoisomer, solvate or prodrug thereof of claim 1, wherein Z is

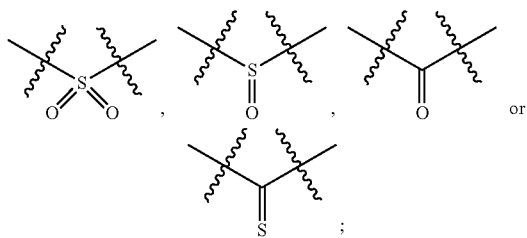

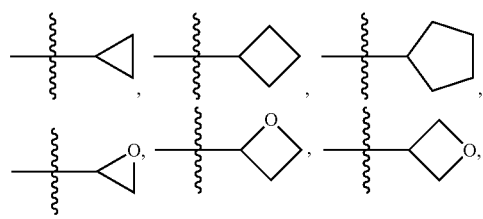

and/or, $R^1$ is hydrogen;

and/or, $R^2$ is hydrogen, methyl, ethyl, n-propyl, isopropyl,

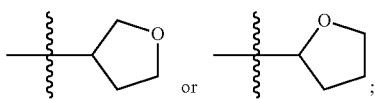

and/or, $R^3$ is

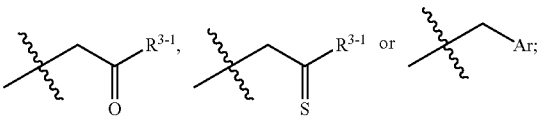

wherein $R^{3-1}$ is hydrogen, hydroxyl, methyl, ethyl, n-propyl, isopropyl, methoxy, ethoxy, n-propoxy, isopropoxy, n-butoxy, tert-butoxy, sec-butoxy or isobutoxy, Ar is phenyl, 5- or 6-membered nitrogen-containing monocyclic heteroaryl;

and/or, $R^4$ is

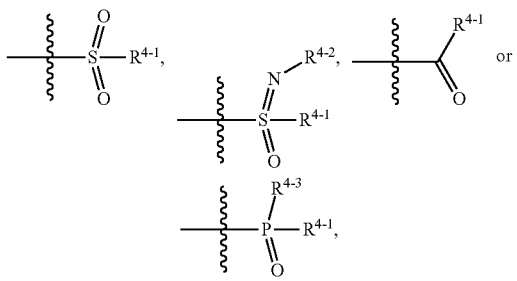

wherein $R^{4-1}$ is phenyl, phenyl with at least one hydrogen atom substituted by $R^{4-11}$, 5- or 6-membered monocyclic heteroaryl, and 5- or 6-membered monocyclic heteroaryl with at least one hydrogen atom substituted by $R^{4-11}$, 8 to 10-membered fused bicyclic heteroaryl, or 8 to 10-membered fused bicyclic heteroaryl with at least one hydrogen atom substituted by $R^{4-11}$, and the $R^{4-11}$ is hydrogen, halogen, nitrogen methyl, ethyl, n-propyl, isopropyl,

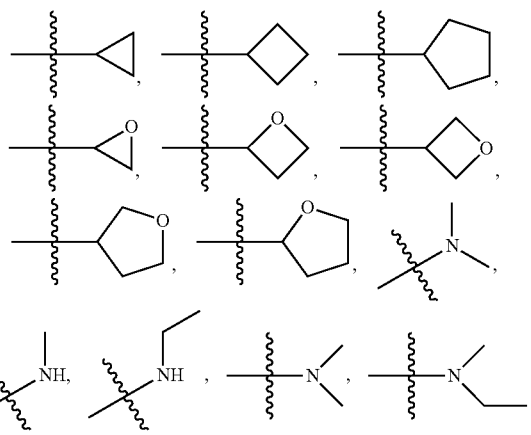

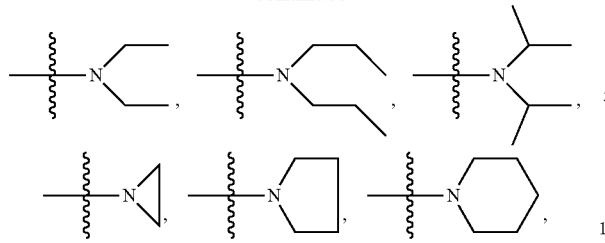

fluoromethyl, fluoroethyl, fluoro-n-propyl, fluoroisopropyl, chloromethyl, chloroethyl, chloro-n-propyl, chloroisopropyl, bromomethyl, bromoethyl, bromo-n-propyl, bromoisopropyl, iodomethyl, iodoethyl, iodo-n-propyl, iodoisopropyl, fluoromethoxy, fluoroethoxy, fluoro-n-propoxy, fluoroisopropoxy, chloromethoxy, chloroethoxy, chloro-n-propoxy, chloroisopropoxy, bromomethoxy, bromoethoxy, bromo-n-propoxy, bromoisopropoxy, iodooxymethyl, iodoethoxy, iodo-n-propoxy, iodoisopropoxy or

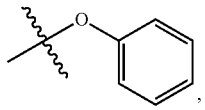

$R^{4-2}$ is methyl, ethyl, n-propyl or isopropyl, or when $R^2$ is methyl, ethyl or n-propyl, $R^{4-2}$ and $R^2$ are bonded to form a 4-8 membered ring, $R^{4-3}$ is methyl, ethyl, n-propyl, isopropyl, methoxy, ethoxy, n-propoxy or isopropoxy;

and/or, when the number of $R^5$ is not 0, each is independently selected from halogen, nitro, nitrile, —$N^+$($R^{5-1}$)$_3$, fluoromethyl, fluoroethyl, fluoro-n-propyl, fluoroisopropyl, chloromethyl, chloroethyl, chloron-n-propyl, chloroisopropyl, bromomethyl, bromoethyl, bromon-n-propyl, bromoisopropyl, —C(O)O$R^{5-1}$, —C(O)$R^{5-1}$, —C(O)N($R^{5-1}R^{5-1a}$), —S(O)$_2R^{5-1}$, —S(O)$R^{5-1}$, —N=C($R^{5-1}R^{5-1a}$), hydroxyl, methyl, ethyl, n-propyl, isopropyl, phenyl, phenyl with at least one hydrogen substituted by $R^{5-1}$, methoxy, ethoxy, n-propoxy, isopropoxy, —N($R^{5-1}R^{5-1a}$), —N($R^{5-1}$C(O)$R^{5-1a}$ and —OC(O)$R^{5-1}$, wherein $R^{5-1}$, $R^{5-1a}$ and $R^{5-1b}$ are each independently hydrogen, methyl, ethyl, n-propyl, isopropyl, fluoromethyl, fluoroethyl, fluoro-n-propyl, fluoroisopropyl, chloromethyl, chloroethyl, chloro-n-propyl, chloroisopropyl, bromomethyl, bromoethyl, bromo-n-propyl or bromoisopropyl, with the proviso that:
the compound of Formula (I) is not

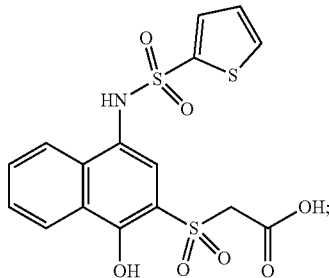 [SMILES: O=C(O)CS(=O)(=O)c1cc(NS(=O)(=O)c2cccs2)c2ccccc2c1O]

and
when $R^1$ and $R^2$ are hydrogen, $R^4$ is

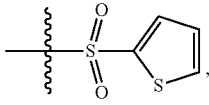 [SMILES: *S(=O)(=O)c1cccs1]

Z is

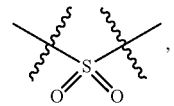

and the number of $R^5$ is 0, then $R^3$ is not —CH$_2$COOCH$_2$CH$_3$.

4. The compound or the pharmaceutically acceptable salt, stereoisomer, solvate or prodrug thereof of claim 1, wherein Z is

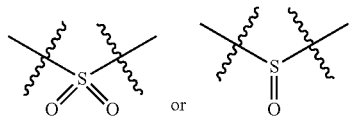

5. The compound or the pharmaceutically acceptable salt, stereoisomer, solvate or prodrug thereof of claim 1, wherein the compound has a structure represented by Formula (II);

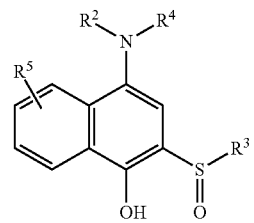

wherein $R^2$ is hydrogen, $C_{1-4}$ alkyl, three to six-membered cycloalkyl or four to six-membered epoxyalkyl; $R^3$ is

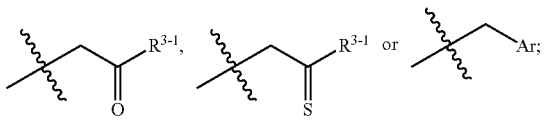

wherein $R^{3-1}$ is hydrogen, hydroxyl, $C_{1-4}$ alkyl, $C_{1-4}$ alkoxy, three to six-membered cycloalkyl, three to six-membered epoxyalkyl, —N($R^{3-2}R^{3-2a}$), —CH$_2$C(O)$R^{3-2}$, —CH$_2$C(O)O$R^{3-2}$ or —CH$_2$C(O)N$R^{3-2}R^{3-2a}$, $R^{3-2}$ and $R^{3-2a}$ are each independently hydrogen, $C_{1-4}$ alkyl or three to six-membered cycloalkyl, Ar is phenyl, 5- or 6-membered monocyclic heteroaryl, or 5- or 6-membered monocyclic heteroaryl with at least one hydrogen atom substituted by $R^{3-3}$, and the $R^{3-3}$ is hydrogen, halogen, $C_{1-4}$ alkyl, three to six-membered cycloalkyl, hydroxyl, $C_{1-4}$ alkoxy, three to six-membered epoxyalkyl, $C_{1-4}$ haloalkyl, $C_{2-4}$ alkenyl, $C_{2-4}$ alkynyl, —N($R^{3-3a}R^{3-3b}$) or phenyl, $R^{3-3a}$ and $R^{3-3b}$ are each independently hydrogen, $C_{1-4}$ alkyl or three to six-membered cycloalkyl;

$R^4$ is

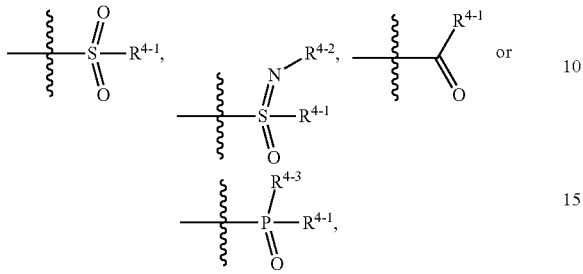

wherein $R^{4-1}$ is phenyl, phenyl with at least one hydrogen atom substituted by $R^{4-11}$, 5- or 6-membered monocyclic heteroaryl, and 5- or 6-membered monocyclic heteroaryl with at least one hydrogen atom substituted by $R^{4-11}$, 8 to 10-membered fused bicyclic heteroaryl, or 8 to 10-membered fused bicyclic heteroaryl with at least one hydrogen atom substituted by $R^{4-11}$, wherein $R^{4-11}$ is hydrogen, halogen, nitro, $C_{1-4}$ alkyl, three to six-membered cycloalkyl, $C_{1-4}$ alkoxy, —N($R^{4-1a}R^{4-1b}$), phenyl, $C_{1-4}$ haloalkyl, $C_{1-4}$ haloalkoxy or

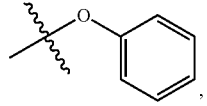

$R^{4-1a}$ and $R^{4-1b}$ are each independently hydrogen, $C_{1-4}$ alkyl or three to six-membered cycloalkyl, and $R^{4-1a}$ and $R^{4-1b}$ can be bonded to each other to form a ring, $R^{4-2}$ is a $C_{1-4}$ alkyl, a three- to six-membered cycloalkyl, or when $R^2$ is a $C_{1-4}$ alkyl, $R^{4-2}$ and $R^2$ are bonded to form a 4 to 8-membered ring, $R^{4-3}$ is $C_{1-4}$ alkyl or $C_{1-4}$ alkoxy; and when the number of $R^5$ is not 0, each is independently selected from halogen, nitro, nitrile, —N$^+$($R^{5-1}$)$_3$, $C_{1-4}$ haloalkyl, —C(O)O$R^{5-1}$, —C(O)$R^{5-1}$, —C(O)N($R^{5-1}R^{5-1a}$), —S(O)$_2R^{5-1}$, —S(O)$R^{5-1}$, —N=C($R^{5-1}R^{5-1a}$), hydroxyl, $C_{1-4}$ alkyl, phenyl, phenyl with at least one hydrogen substituted by $R^{5-1}$, $C_{1-4}$ alkoxy, —N($R^{5-1}R^{5-1a}$), —N($R^{5-1}$)C(O)$R^{5-1a}$, —OC(O)$R^{5-1}$, —OC(O)N($R^{5-1}R^{5-1a}$) and —S$R^{5-1}$, wherein $R^{5-1}$, $R^{5-1a}$ and $R^{5-1b}$ are each independently hydrogen, $C_{1-4}$ alkyl, $C_{2-4}$ alkenyl, $C_{2-4}$ alkynyl, $C_{1-4}$ alkyl with at least one hydrogen substituted by halogen, $C_{2-4}$ alkenyl with at least one hydrogen substituted by halogen, or $C_{2-4}$ alkynyl with at least one hydrogen substituted by halogen.

6. The compound or the pharmaceutically acceptable salt, stereoisomer, solvate or prodrug thereof of claim 5, wherein when the number of $R^5$ is not 0, each $R^5$ is independently selected from halogen, nitro, nitrile, —N$^+$($R^{5-1}$)$_3$, $C_{1-4}$ haloalkyl, —C(O)O$R^{5-1}$, —C(O)$R^{5-1}$, —C(O)N($R^{5-1}R^{5-1a}$), —S(O)$_2R^{5-1}$, —S(O)$R^{5-1}$ and —N=C($R^{5-1}R^{5-1a}$);

wherein $R^{5-1}$ and $R^{5-1a}$ are each independently hydrogen, $C_{1-4}$ alkyl, $C_{2-4}$ alkenyl, $C_{2-4}$ alkynyl, and $C_{1-4}$ alkyl with at least one hydrogen substituted by halogen, $C_{2-4}$ alkenyl with at least one hydrogen substituted by halogen or $C_{2-4}$ alkynyl group with at least one hydrogen substituted by halogen.

7. The compound or the pharmaceutically acceptable salt, stereoisomer, solvate or prodrug thereof of claim 1, wherein the compound has a structure represented by Formula (III);

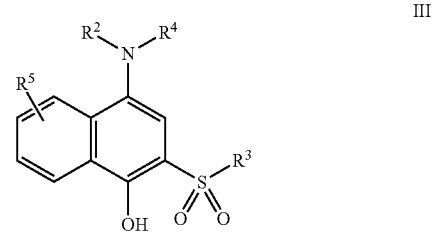

wherein, $R^2$ is hydrogen, $C_{1-4}$ alkyl, three to six-membered cycloalkyl or four to six-membered epoxyalkyl;

$R^3$ is

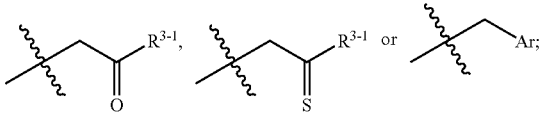

wherein $R^{3-1}$ is hydrogen, hydroxyl, $C_{1-4}$ alkyl, $C_{1-4}$ alkoxy, three to six-membered cycloalkyl, three to six-membered epoxyalkyl, —N($R^{3-2}R^{3-2a}$), —CH$_2$C(O)$R^{3-2}$, —CH$_2$C(O)O$R^{3-2}$ or —CH$_2$C(O)N$R^{3-2}R^{3-2a}$, $R^{3-2}$ and $R^{3-2a}$ are each independently hydrogen, $C_{1-4}$ alkyl or three to six-membered cycloalkyl, Ar is phenyl, 5- or 6-membered monocyclic heteroaryl, or 5- or 6-membered monocyclic heteroaryl with at least one hydrogen atom substituted by $R^{3-3}$, and the $R^{3-3}$ is hydrogen, halogen, $C_{1-4}$ alkyl, three to six-membered cycloalkyl, hydroxyl, $C_{1-4}$ alkoxy, three to six-membered epoxyalkyl, $C_{1-4}$ haloalkyl, $C_{2-4}$ alkenyl, $C_{2-4}$ alkyne, —N($R^{3-3a}R^{3-3b}$) or phenyl, $R^{3-3a}$ and $R^{3-3b}$ are each independently hydrogen, $C_{1-4}$ alkyl or three to six-membered cycloalkyl;

$R^4$ is

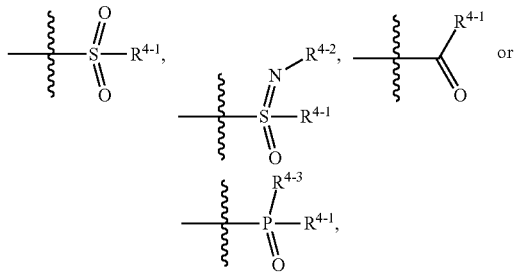

wherein $R^{4-1}$ is phenyl, phenyl with at least one hydrogen atom substituted by $R^{4-11}$, 5- or 6-membered monocyclic heteroaryl, and 5- or 6-membered monocyclic heteroaryl with at least one hydrogen atom substituted by $R^{4-11}$, 8 to 10-membered fused bicyclic heteroaryl, or 8 to 10-membered fused bicyclic heteroaryl with at least one hydrogen atom substituted by $R^{4-11}$, and the $R^{4-11}$ is hydrogen, halogen, nitro, $C_{1-4}$ alkyl, three to six-membered cycloalkyl, $C_{1-4}$ alkoxy, —N($R^{4-1a}$ $R^{4-1b}$), phenyl, $C_{1-4}$ haloalkyl, $C_{1-4}$ haloalkoxy or

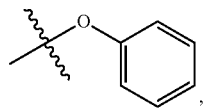

, $R^{4-1a}$ and $R^{4-1b}$ are each independently hydrogen, $C_{1-4}$ alkyl or three to six-membered cycloalkyl, and $R^{4-1a}$ and $R^{4-1b}$ can be bonded to each other to form a ring, $R^{4-2}$ is $C_{1-4}$ alkyl or three- to six-membered cycloalkyl, or when $R^2$ is $C_{1-4}$ alkyl, $R^{4-2}$ and $R^2$ are bonded to form a 4 to 8-membered ring, $R^{4-3}$ is $C_{1-4}$ alkyl or $C_{1-4}$ alkoxy; and when the number of $R^5$ is not 0, each $R^5$ is independently selected from halogen, nitro, nitrile group, —$N^+$($R^{5-1}$)$_3$, $C_{1-4}$ haloalkyl, —C(O)O$R^{5-1}$, —C(O)$R^{5-1}$, —C(O)N($R^{5-1}R^{5-1a}$), —S(O)$_2R^{5-1}$, —S(O)$R^{5-1}$, —N=C($R^{5-1}R^{5-1a}$), hydroxyl, $C_{1-4}$ alkyl, phenyl, phenyl with at least one hydrogen substituted by $R^{5-1}$, $C_{1-4}$ alkoxy, —N($R^{5-1}R^{5-1a}$), —N($R^{5-1}$) C(O)$R^{5-1a}$, —OC(O)$R^{5-1}$, —OC(O)N($R^{5-1}R^{5-1a}$) or —S$R^{5-1}$, wherein $R^{5-1}$, $R^{5-1a}$ and $R^{5-1b}$ are each independently hydrogen, $C_{1-4}$ alkyl, $C_{2-4}$ alkenyl, $C_{2-4}$ alkynyl, $C_{1-4}$ alkyl with at least one hydrogen substituted by halogen, $C_{2-4}$ alkenyl with at least one hydrogen substituted by halogen, and $C_{2-4}$ alkynyl with at least one hydrogen substituted by halogen, with the proviso that:

the compound of Formula (III) is not

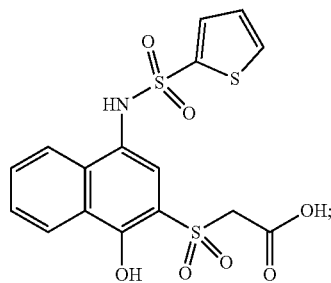 [SMILES: O=C(O)CS(=O)(=O)c1cc(NS(=O)(=O)c2cccs2)c2ccccc2c1O]

and when $R^2$ is hydrogen, $R^4$ is

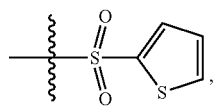

, and the number of $R^5$ is 0, then $R^3$ is not —$CH_2COOCH_2CH_3$.

8. The compound or the pharmaceutically acceptable salt, stereoisomer, solvate or prodrug thereof of claim 7, wherein when the number of $R^5$ is not 0, each $R^5$ is independently selected from hydroxyl, $C_{1-4}$ alkyl, phenyl, phenyl with at least one hydrogen substituted by $R^{5-1}$, $C_{1-4}$ alkoxy, —N($R^{5-1}R^{5-1a}$), —N($R^{5-1}$)C(O)$R^{5-1a}$, —OC(O)$R^{5-1}$, —OC(O)N($R^{5-1}R^{5-1a}$) or —S$R^{5-1}$, wherein $R^{5-1}$, $R^{5-1a}$ and $R^{5-1b}$ are each independently hydrogen, $C_{1-4}$ alkyl, $C_{2-4}$ alkenyl, $C_{2-4}$ alkynyl, $C_{1-4}$ alkyl with at least one hydrogen substituted by halogen, $C_{2-4}$ alkenyl with at least one hydrogen substituted by halogen and $C_{2-4}$ alkynyl with at least one hydrogen substituted by halogen.

9. The compound or the pharmaceutically acceptable salt, stereoisomer, solvate or prodrug thereof of claim 1, wherein the compound is selected from any one of the following compounds:

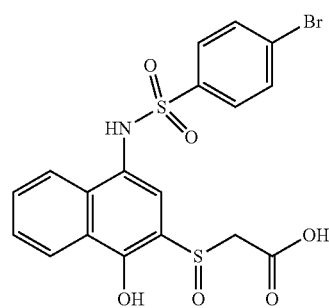

I-1

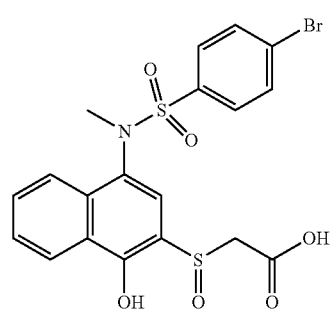

I-2

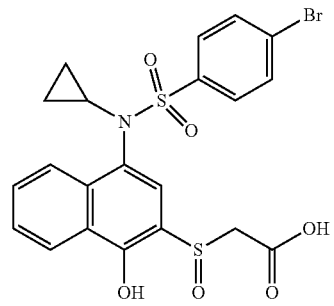

I-3

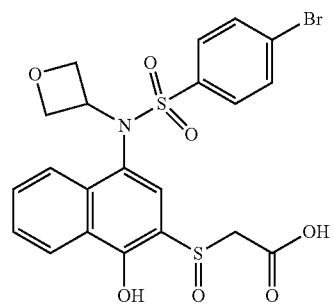

I-4

I-5
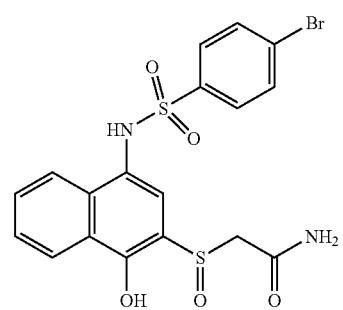
I-6
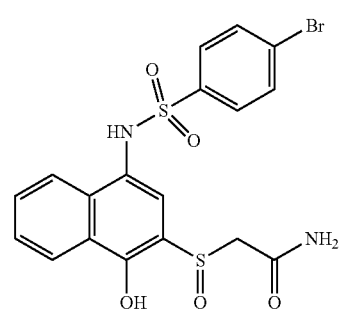
I-7-1
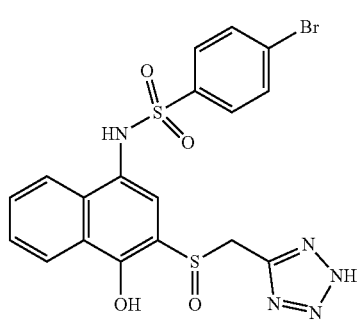
I-8
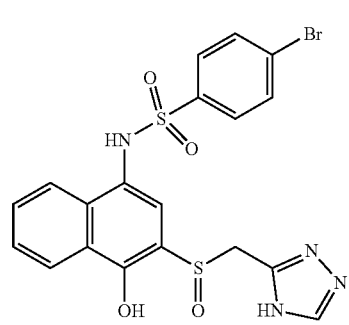
I-9-1
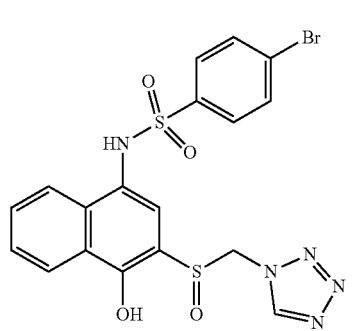
I-9-2
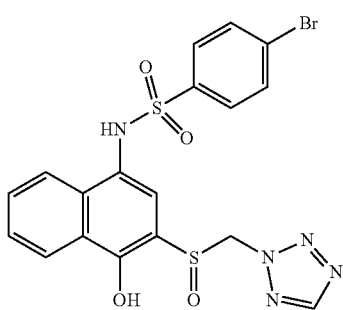
I-10
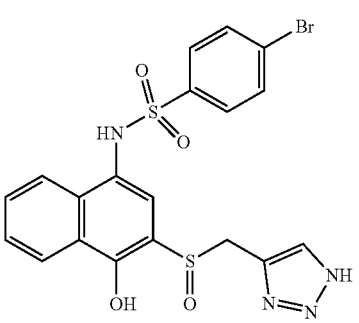
I-11-1
I-11-2
I-12

129
-continued
I-13-1
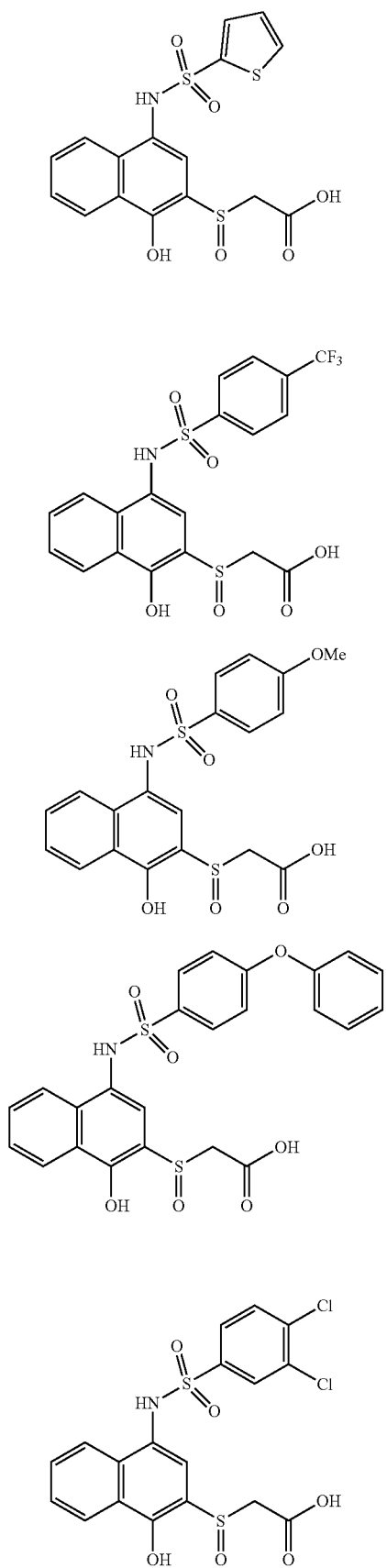
I-14-1
I-15-1
I-16-1
I-17-1
130
-continued
I-18-1
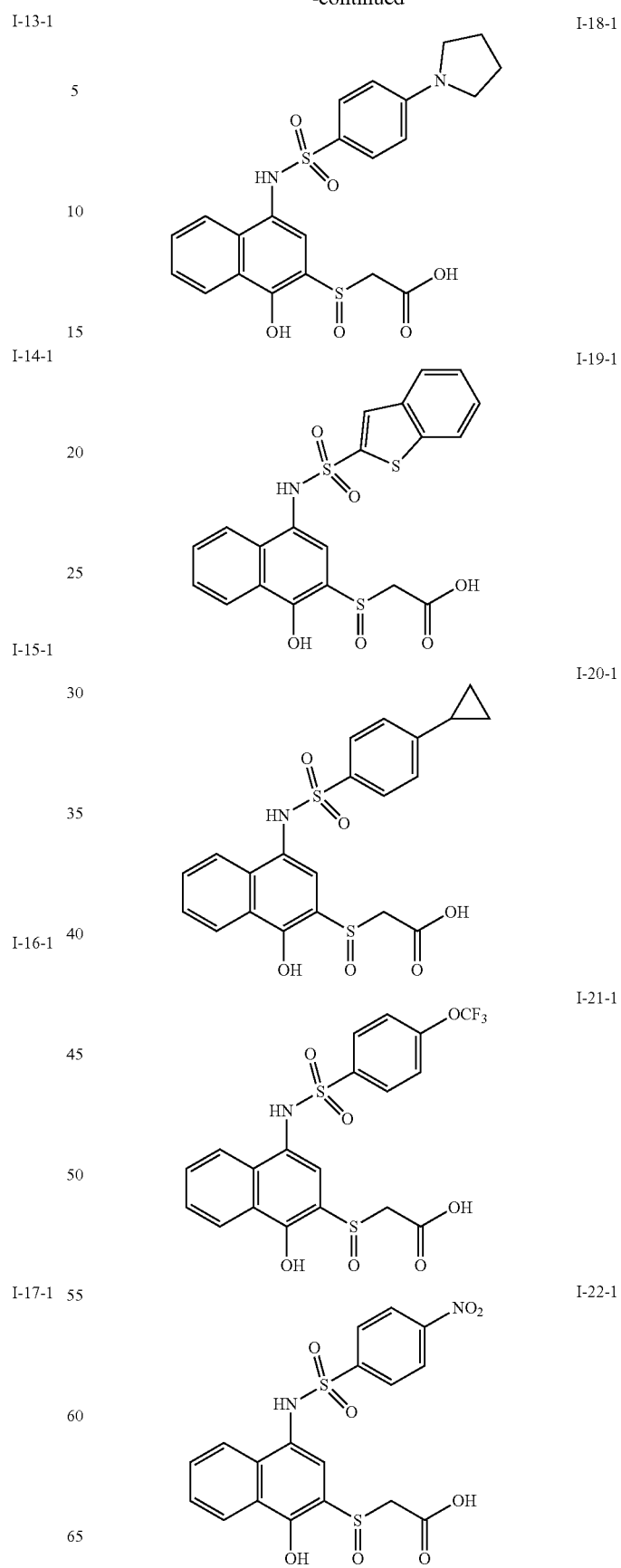
I-19-1
I-20-1
I-21-1
I-22-1

| | |
|---|---|
| I-23-1 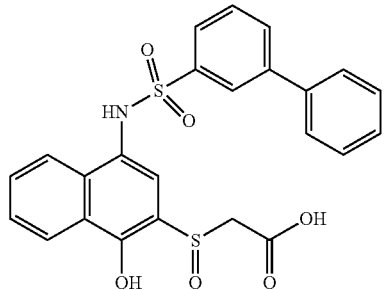 | I-28 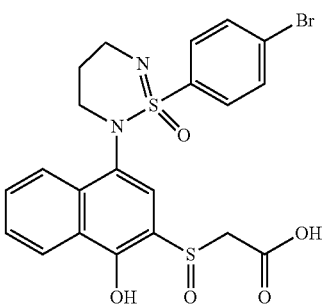 |
| I-24-1 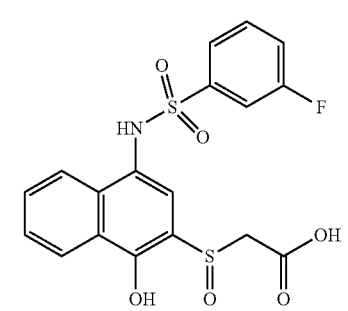 | I-29 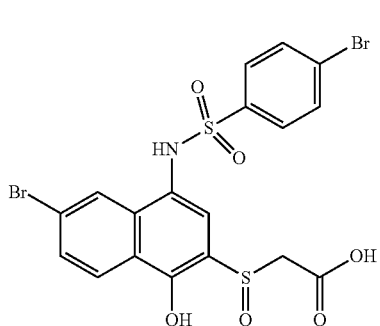 |
| I-25-1 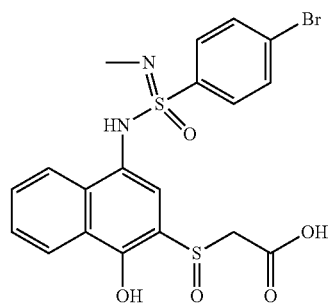 | I-30 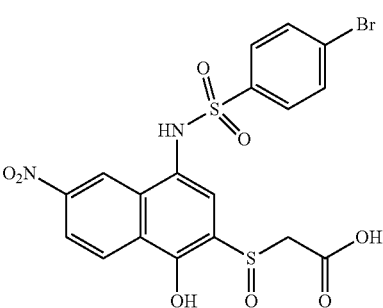 |
| I-26 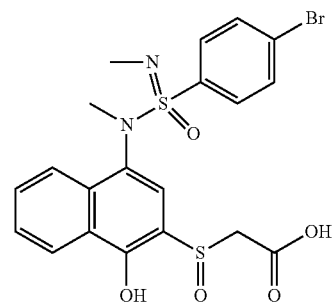 | I-31 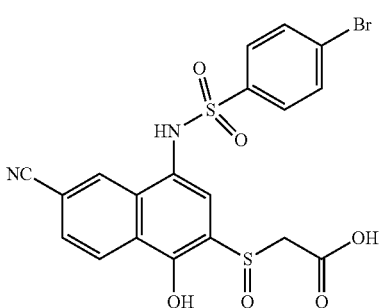 |
| I-27 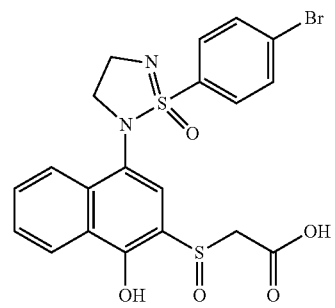 | I-32 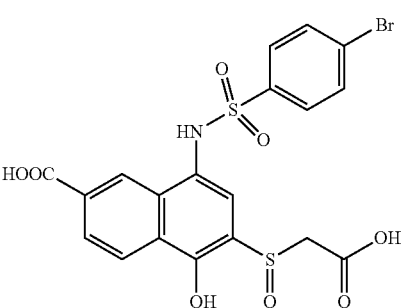 |

I-33
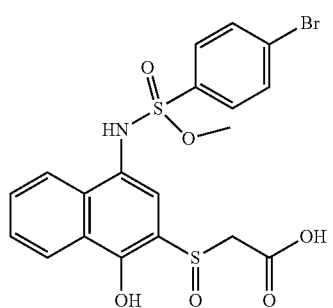
I-34
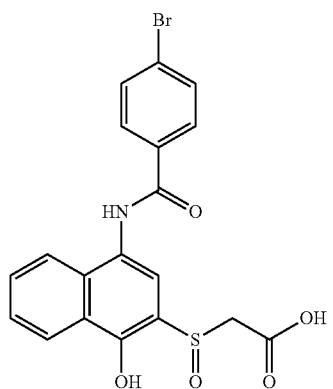
I-35-1
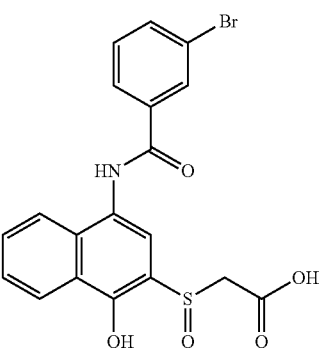
I-36
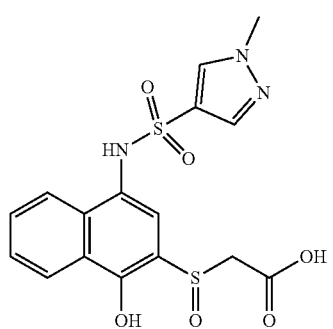
I-37
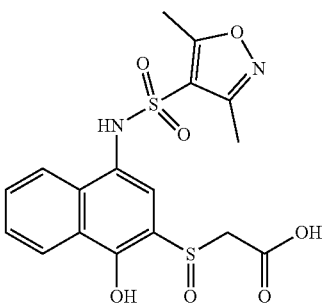
I-38
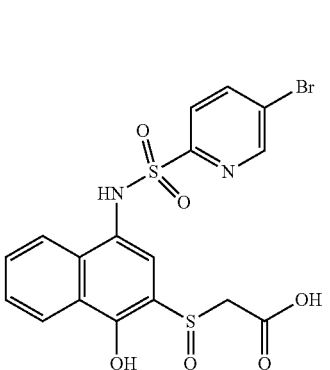
I-39
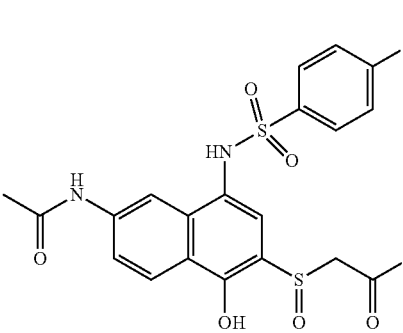
I-40-1
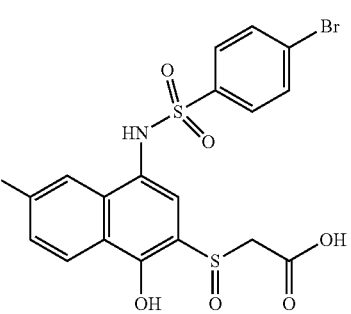
I-41-1
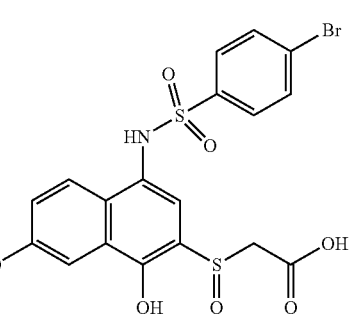

-continued
I-42
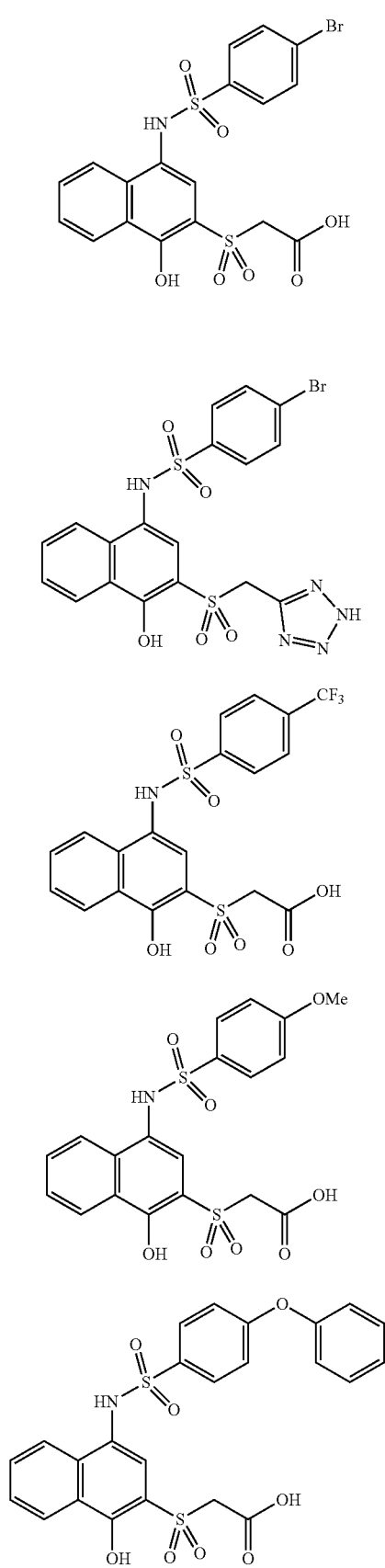
I-7-2
I-14-2
I-15-2
I-16-2
-continued
I-17-2
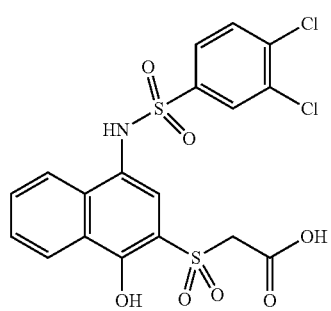
I-18-2
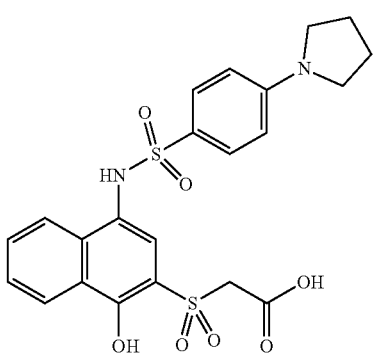
I-19-2
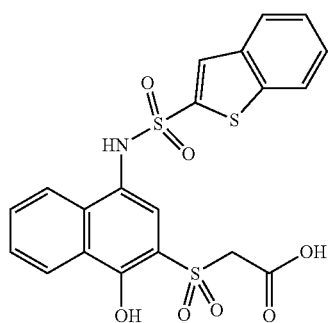
I-20-2
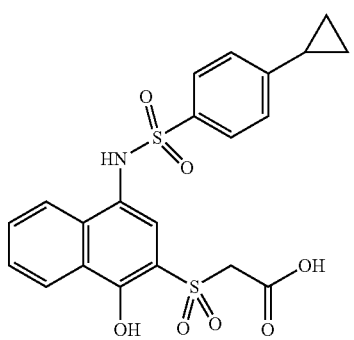
I-21-2
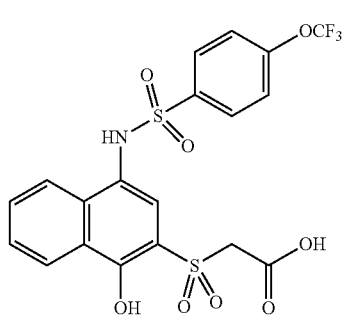

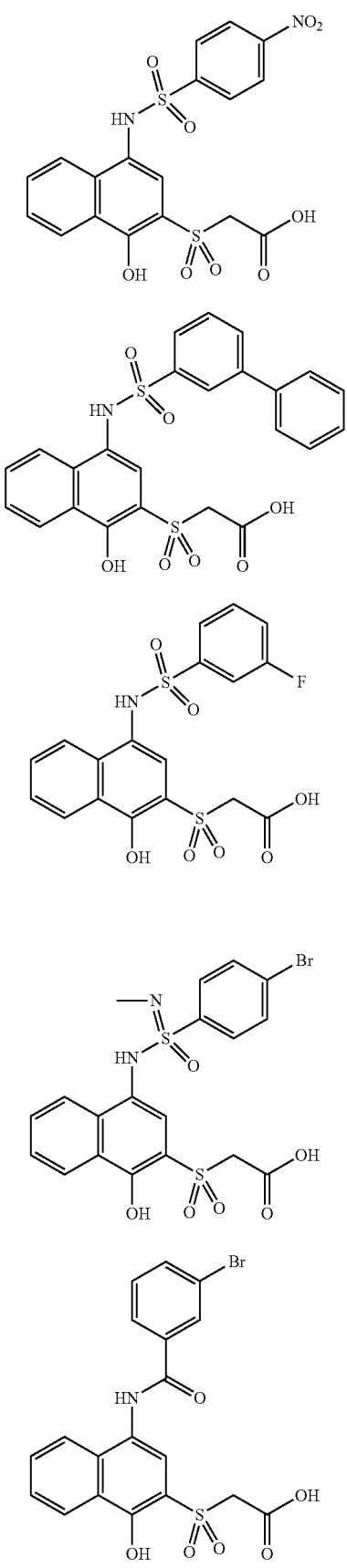
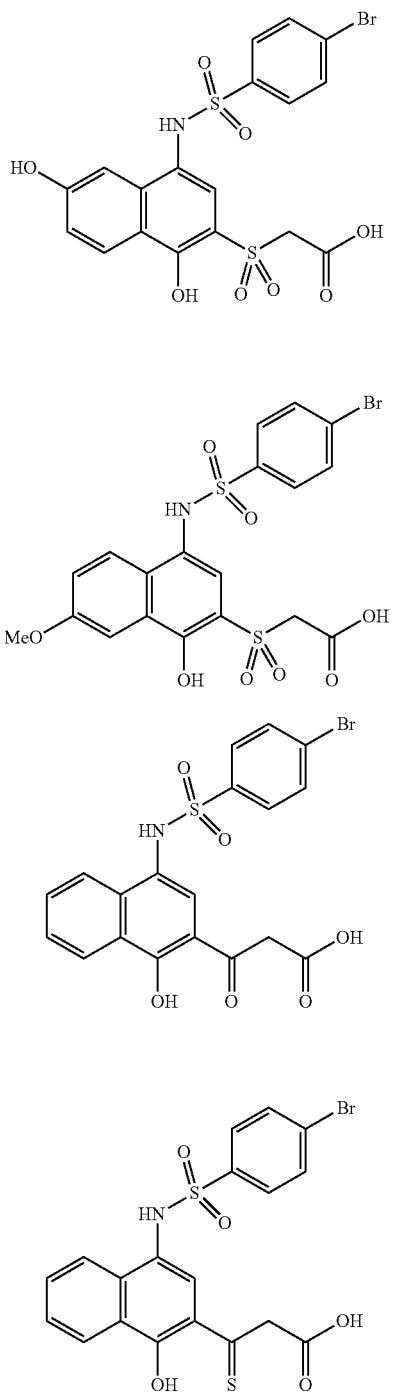

10. A pharmaceutical composition comprising the compound, or the pharmaceutically acceptable salt, stereoisomer, solvate or prodrug thereof of claim 1.

11. A method of inducing mitophagy in a subject, comprising administering to the subject the compound, or the pharmaceutically acceptable salt, stereoisomer, solvate or prodrug thereof of claim 1.

12. A method of inducing mitophagy in a subject, comprising administering to the subject the pharmaceutical composition of claim 10.

13. The compound or the pharmaceutically acceptable salt, stereoisomer, solvate or prodrug thereof of claim 1, wherein Z is not
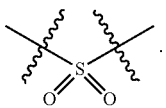 [SMILES: *S(*)(=O)=O]
* * * * *